US007390648B1

(12) United States Patent
Palacios-Boyce

(10) Patent No.: US 7,390,648 B1
(45) Date of Patent: Jun. 24, 2008

(54) MICROELECTROMECHANICAL DEVICES USEFUL FOR MANIPULATING CELLS OR EMBRYOS, KITS THEREOF, METHOD OF MAKING SAME, AND METHODS OF USE THEREOF

(76) Inventor: Monica Palacios-Boyce, 81 Haynes Hill Rd., Wales, MA (US) 01081

( * ) Notice: Subject to any disclaimer, the term of this patent is extended or adjusted under 35 U.S.C. 154(b) by 0 days.

(21) Appl. No.: 10/031,259

(22) PCT Filed: Apr. 24, 2000

(86) PCT No.: PCT/US00/11040

§ 371 (c)(1),
(2), (4) Date: Jun. 3, 2002

(87) PCT Pub. No.: WO00/65137

PCT Pub. Date: Nov. 2, 2000

Related U.S. Application Data

(60) Provisional application No. 60/149,269, filed on Aug. 17, 1999, provisional application No. 60/147,802, filed on Aug. 9, 1999, provisional application No. 60/130,802, filed on Apr. 23, 1999.

(51) Int. Cl.
*C12M 1/00* (2006.01)
(52) U.S. Cl. ............... 435/285.1; 435/288.4; 435/305.1; 435/440; 422/64
(58) Field of Classification Search ............. 422/64; 435/285.1, 285.2, 288.4, 305.1, 305.2, 440; *C12M 1/00*
See application file for complete search history.

(56) References Cited

U.S. PATENT DOCUMENTS

| 5,006,117 | A | | 4/1991 | Cassou |
|---|---|---|---|---|
| 5,114,854 | A | | 5/1992 | Bertholdt |
| 5,256,376 | A | * | 10/1993 | Callan et al. ................. 422/102 |
| 5,262,128 | A | | 11/1993 | Leighton et al. |
| 5,320,808 | A | * | 6/1994 | Holen et al. .................. 422/64 |
| 5,424,209 | A | | 6/1995 | Kearney |
| 5,635,358 | A | * | 6/1997 | Wilding et al. ............... 435/7.2 |
| 5,665,582 | A | | 9/1997 | Kausch et al. |
| 5,863,708 | A | | 1/1999 | Zanzucchi et al. |
| 5,961,923 | A | | 10/1999 | Nova et al. |
| 5,968,820 | A | | 10/1999 | Zborowski et al. |
| 6,050,935 | A | | 4/2000 | Ranoux et al. |

OTHER PUBLICATIONS

Senturia, S. et al., "A Computer-Aided Design System for Microelectromechanical Systems (MEMCAD)," Journal of Microelectromechanical Systems, 1(1):3, Mar. 1992.

(Continued)

*Primary Examiner*—David A Redding
(74) *Attorney, Agent, or Firm*—Mathews, Shepherd, McKay & Bruneau, P.A.

(57) ABSTRACT

The present invention relates generally to microelectromechanical systems (MEMS) devices for the manipulation of cells or groups of cells, such as oocytes, embryos, and sperm. In particular, the present invention relates to Cell Labeling MEMS devices (2F), Microinjection MEMS devices, Intra-Cytoplasmic Sperm Injection ("ICSI") MEMS devices, Zona Coring MEMS devices, Enucleation MEMS devices, Enucleation/Nuclear Transfer MEMS devices, and Cytoplasmic Transfer MEMS devices. The present invention also relates to kits containing the MEMS devices of the present invention.

34 Claims, 19 Drawing Sheets

OTHER PUBLICATIONS

Clerc, P-A, et al., "Advanced Deep Reactive Ion Etching: A Versatile Tool for Microelectromechanical Systems," J. Micromech. Microeng., 8(4):272-278, 1998.

Petersen, K. et al., "Toward Next Generation Clinical Diagnostic Instruments: Scaling and New Processing Paradigms," Biomedical Microdevices, 1(1):71-79, 1998.

Wagner, J. et al., "Transgenic Animals as Models for Human Disease," Clin. and Exper. Hypertension, 17(4):593-605, 1995.

Woychi, R. et al., "Insertional Mutagenesis in Transgenic Mice Generated by the Pronuclear Microinjection Procedure," Int. J. Dev. Biol., 42(7 Spec No.):1009-1017, 1998.

Ebert, K., "The Use of Transgenic Animals in Biotechnology," Int. J. Dev. Biol., 42(7 Spec No.):1003-1008, 1998.

Joris, H. et al., "Intracytoplasmic Sperm Injection: Laboratory Set-up and Injection Procedure," Human Reproduction, 13 Supplement 1:76-86, 1998.

Palermo, G. et al., "Intracytoplasmic Sperm Injection: A Powerful Tool to Overcome Fertilization Failure," Fertility and Sterility, 65(5):899-908, May 1996.

Meldrum, D. et al., "Assisted Hatching Reduces the Age-Related Decline in IVF Outcome in Women Younger than Age 43 Without Increasing Miscarriage or Monozygotic Twinning," Journal of Assisted Reproduction and Genetics, 15(7):418-421, 1998.

Magli, M. et al., "Rescue of Implantation Potential in Embryos with Poor Prognosis by Assisted Zona Hatching," Human Reproduction, 13(5):1331-1335, 1998.

Campbell, K. et al., "Sheep Cloned by Nuclear Transfer from a Cultured Cell Line," Nature 380, 64-66, Mar. 1996.

Heyman, Y. et al., "Cloning in Cattle: From Embryo Splitting to Somatic Nuclear Transfer," Reprod. Nutr. Dev., 38(6):595-603, 1998.

Loi, P. et al., "Embryo Transfer and Related Technologies in Sheep Reproduction," Reprod. Nutr. Dev., 38(6):615-628, 1998.

Lanzendorf, S. et al., "Pregnancy Following Transfer of Ooplasm from Cryopreserved-Thawed Donor Oocytes into Recipient Oocytes," Fertility and Sterility, 71(3):575-577, Mar. 1999.

Wheeler, M.B., Development of Microelectromechanical Systems to Analyze Individual Mammalian Embryos: Embryo Biocompatibility and Individual Embryo Transport on Silicon A Chip, Arquivos da faculdade de Veterinaria UFRGS, Sociedade Brasileira de Transferencia de Embraoes, vol. 26, No. 1, 1998 (Supl), p. 391.

* cited by examiner

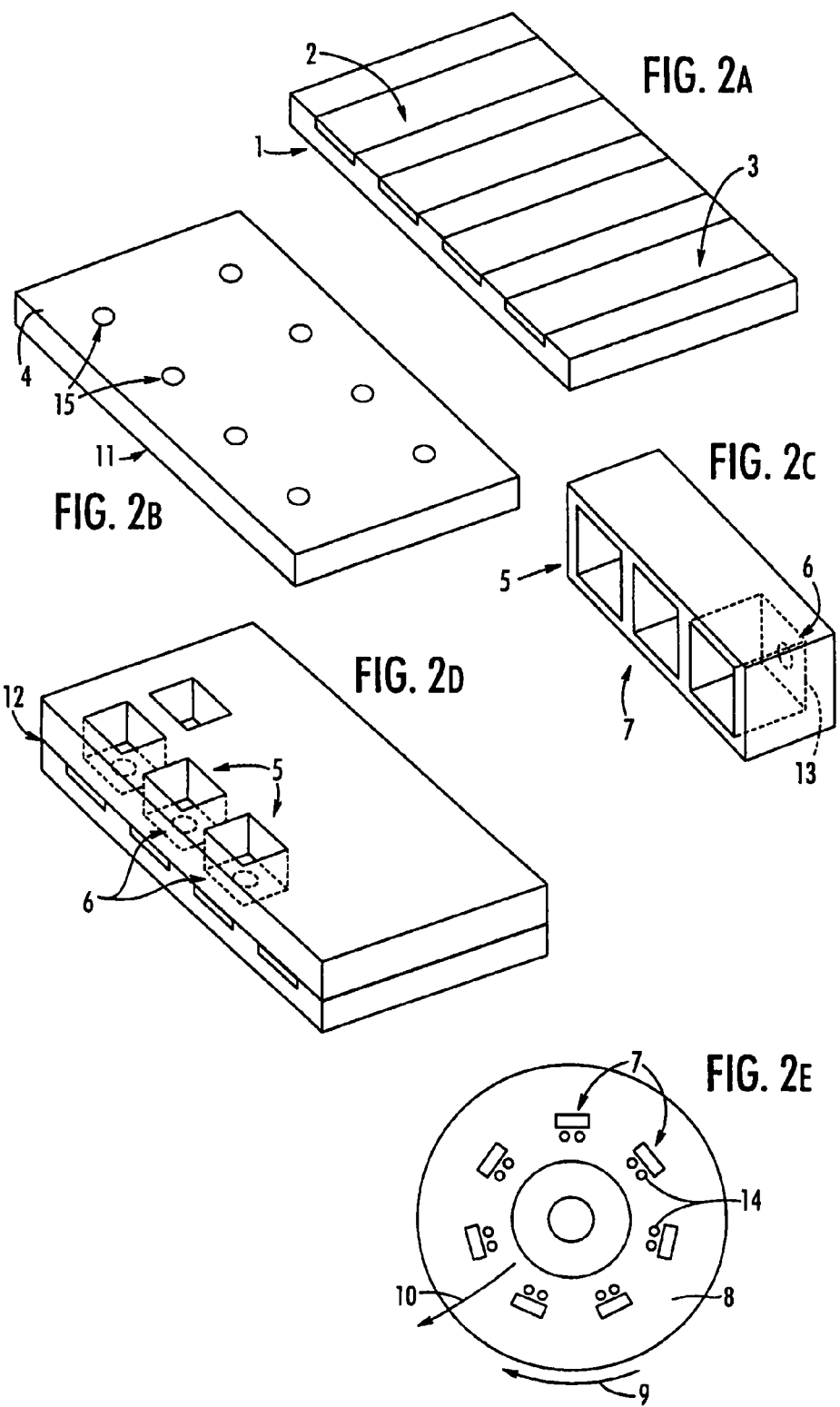

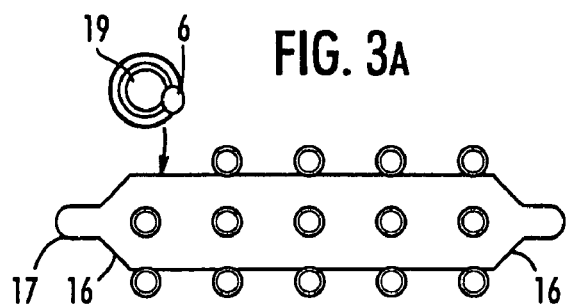 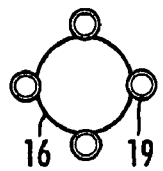
FIG. 3A  FIG. 3B
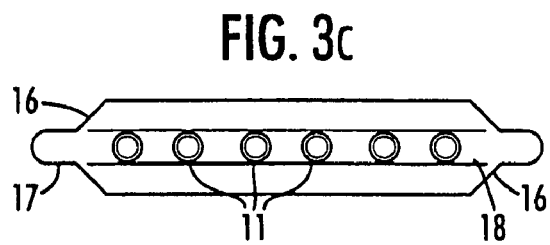 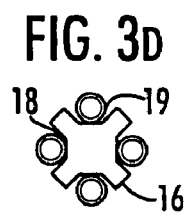
FIG. 3C  FIG. 3D
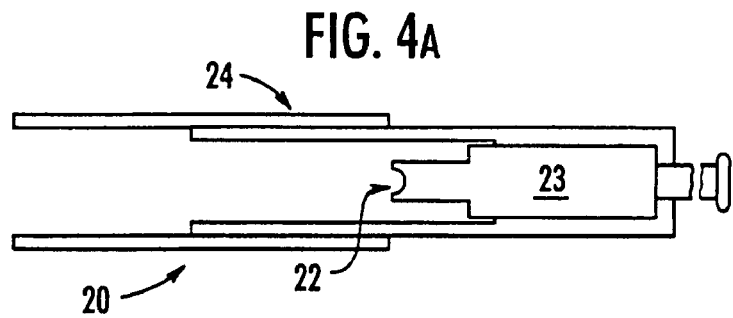
FIG. 4A
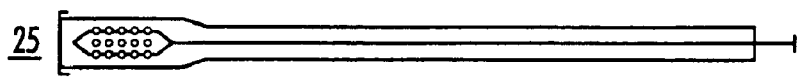
FIG. 4B
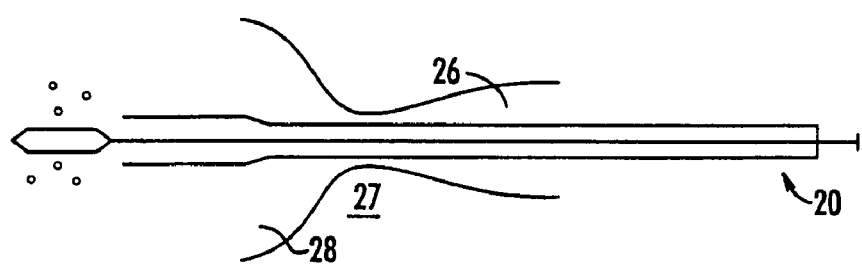
FIG. 4C

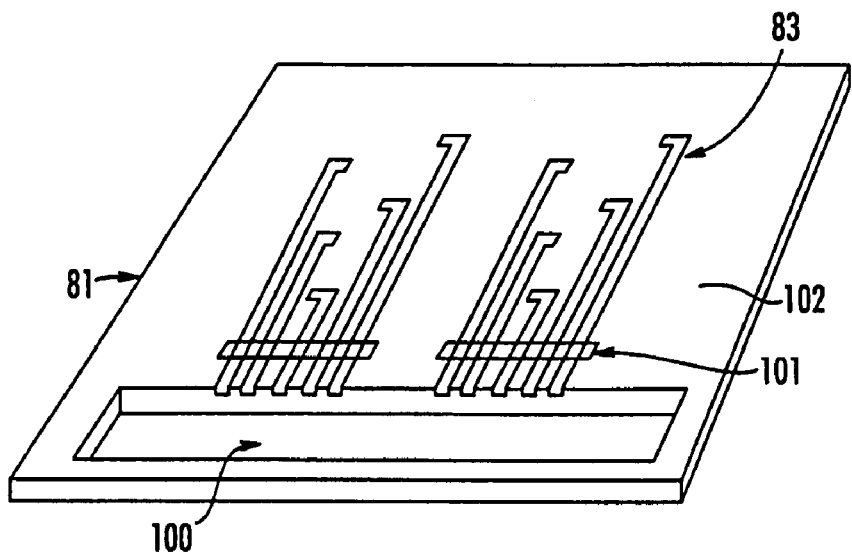
FIG. 15
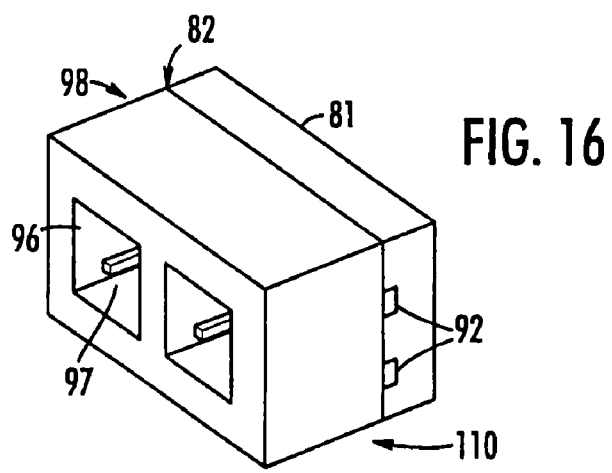
FIG. 16
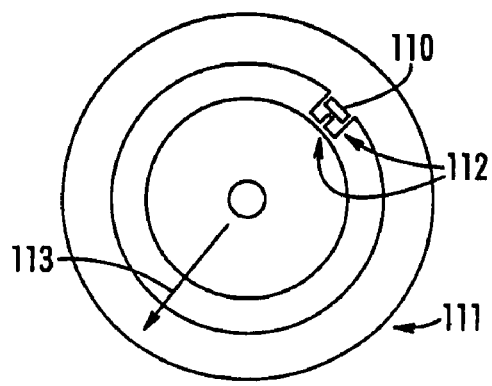

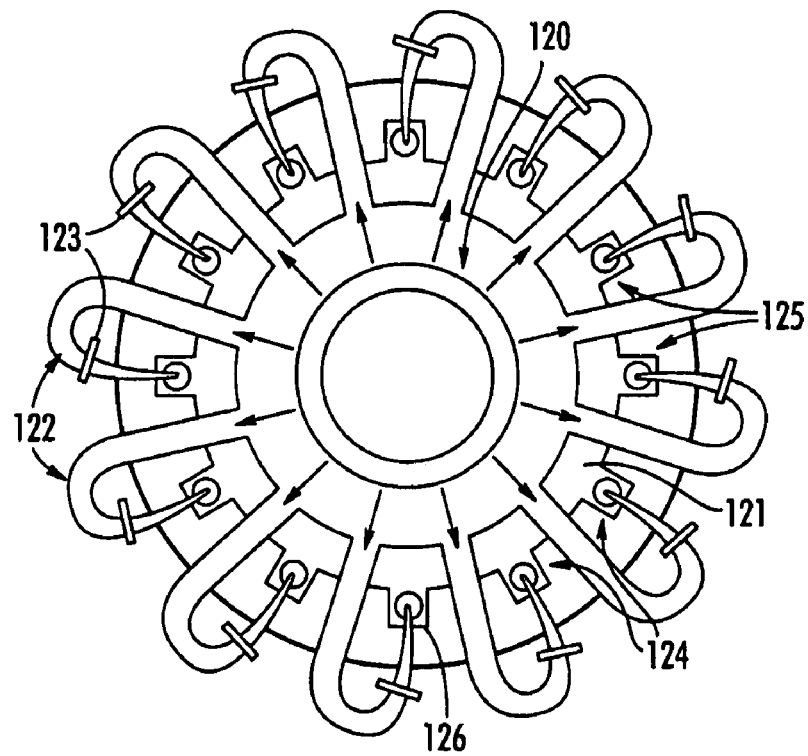
FIG. 17
FIG. 18
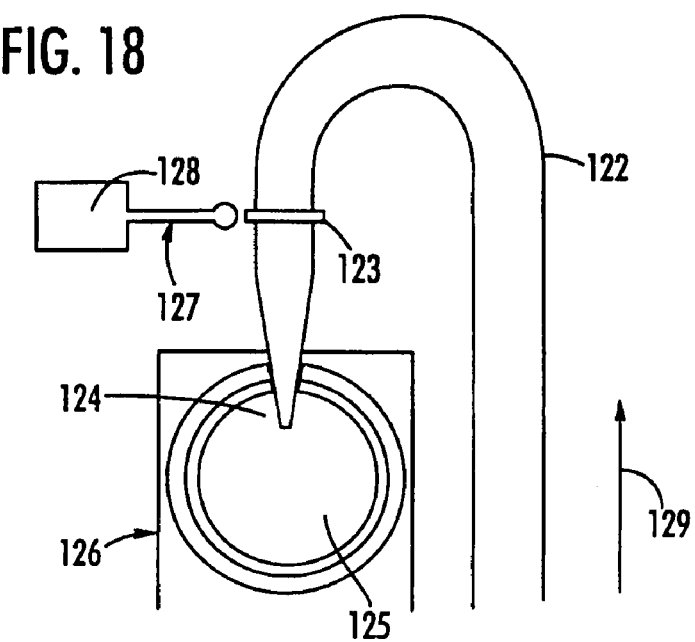

MICROELECTROMECHANICAL DEVICES USEFUL FOR MANIPULATING CELLS OR EMBRYOS, KITS THEREOF, METHOD OF MAKING SAME, AND METHODS OF USE THEREOF

This application is a national stage application, filed under 35 U.S.C. 371, of PCT/US00/11040, filed Apr. 24, 2000, which claims the benefit of U.S. Provisional Application No. 60/130,802 filed Apr. 23, 1999, U.S. Provisional Application No. 60/147,802 filed Aug. 9, 1999, and U.S. Provisional Application No. 60/149,269 filed Aug. 17, 1999, the disclosures of which are incorporated by reference herein in their entirety.

FIELD OF THE INVENTION

The present invention relates generally to microelectromechanical systems (MEMS) devices for the manipulation of cells or groups of cells, such as oocytes, embryos, and sperm. In particular, the present invention relates to Cell Labeling MEMS devices, Labelable Zona Anchor MEMS devices, Microinjection MEMS devices, IntraCytoplasmic Sperm Injection ("ICSI") MEMS devices, Zona Coring MEMS devices, Enucleation MEMS devices, Enucleation/Nuclear Transfer MEMS devices, and cytoplasmic transfer MEMS devices. The present invention also relates to kits containing the MEMS devices of the present invention.

The present invention also relates to devices and articles of manufacture for manipulating and using MEMS devices of the invention. More particularly, the present invention further relates to a centrifugal platter, labelable zona anchor MEMS device platforms and labelable zona anchor MEMS device platform holders.

The present invention also relates to microelectromechanical system arrays and devices useful for cell culture. In particular, the present invention relates to single layer culture arrays, multi-layer culture arrays, multi-layer culture array environmental controllers, multi-compartment, multi-modal incubators, and environmental control instruments.

The present invention also relates to methods of using the MEMS devices and kits of the present invention.

The present invention further relates to methods of making the MEMS devices of the present invention.

BACKGROUND OF THE INVENTION

Microelectromechanical Systems (MEMS) are machines fabricated on a microscopic scale using surface micromachining or LIGA processes. MEMS devices can include moveable members (e.g., gears, rotors, linkages, levers, hinges and mirrors) for applications including sensing (e.g., acceleration or chemicals), switching (electrical or optical signals) and optical display (e.g., moveable mirrors) functions. MEMS devices can further include actuators or motors for driving gear trains to perform various functions including coded locks and self-assembling structures.

In recent years, the design possibilities of microelectromechanical systems (MEMS) have expanded as the field has further matured. Recent advances in single crystal silicon wafer manipulation, the addition of integrated circuits as a practical modality for controlling these microstructures as well as other associated technologies has widened the horizon of possible uses (Senturia, S. D., et al., (1992) "A Computer-Aided Design System for Microelectromechanical Systems (MEMCAD)" *Journal of Microelectromechanical Systems* 1(1):3; Clerc, P-A., et al., (1998) "Advanced deep reactive ion etching: a versatile tool for microelectromechanical systems" *J. Micromech. Microeng.* 8(4):272-278; Petersen, K. E., (1998) "Toward Next Generation Clinical Diagnostic Instruments Scaling and New Processing Paradigms" *Biomedical Microdevices* 1 (1):71-79). One of the most promising novel aspects of this field is the design of MEMS which modulate and manipulate the small scale world of individual cells, thus facilitating, for the first time, an actual hands-on method for addressing biological issues at the level of the most basic unit of order in multicellular organisms.

Whereas many cells in the body are of a size on the order of a few microns, there is a special class of cells, the female gamete called the oocyte, which is far larger, on the order of 100 microns. Further, these cells, in many animals from sea urchins to mammals, are surrounded by a five to twenty micron thick selectively permeable glycoprotein coat called the Zona Pellucida.

The modification of the surface of the glycoprotein coating of oocytes and embryos is a desirable operation in endeavors such as the labeling of a great many of oocytes and embryos in the animal husbandry industry.

Further, the delivery of and removal of materials into and out of the cytoplasm of oocytes is a desirable operation in endeavors such as the generation of transgenic animals, intracytoplasmic sperm injection, assisted hatching, enucleation, nuclear transfer, and cytoplasmic transfer. At present the outcome of these procedures, being technically demanding and relatively novel and as such, not optimized, is very poor. The generation of transgenic animals born by way of microinjection of pronuclei offers very low percentages of actual transgenic animals but the applications for transgenic animals offers great promise (Wagner J, et al., (1995) "Transgenic animals as models for human disease" *Clin Exp Hypertens* 1995 May; 17(4):593-605; Woychik R P, and Alagramam K, (1998) "Insertional mutagenesis in transgenic mice generated by the pronuclear microinjection procedure" *Int J Dev Biol* 42(7 Spec No): 1009-17; Ebert K. M., (1998) "The use of transgenic animals in biotechnology" *Int J Dev Biol* 1998; 42(7 Spec No):1003-8). The use of intracytoplasmic sperm injection (ICSI), the placement of a sperm into the cytoplasm of an oocyte using a microinjection pipette, can be found in both animal husbandry as well as in human assisted reproduction (Joris H, et al. (1998) "Intracytoplasmic sperm injection: laboratory set-up and injection procedure" *Hum Reprod* 13 Suppl 1:76-86). Being a relatively new procedure, not all human assisted reproduction clinics offer ICSI as an option but studies have shown that it can offer significant advantages to those couples suffering from male factor infertility (Palermo G. D., et al. (1996) "Intracytoplasmic sperm injection: a powerful tool to overcome fertilization failure" *Fertil Steril* 65(5):899-908).

Additionally, many assisted reproduction clinics have found that the use of assisted hatching, the removal of a portion of the glycoprotein coating to facilitate embryo escape from the glycoprotein coat, offers the chance of a positive reproductive outcome to those women who produce embryos with impaired zona pellucidas (Meldrum D R, et al. (1998) "Assisted hatching reduces the age-related decline in IVF outcome in women younger than age 43 without increasing miscarriage or monozygotic twinning." *J Assist Reprod Genet.* 15(7):418-21; Magli M C, et al. (1998) "Rescue of implantation potential in embryos with poor prognosis by assisted zona hatching" *Hum Reprod* 13(5):1331-5).

More recent developments in the animal husbandry field report that somatic cell nuclei can be used as nuclear donors in nuclear transfer (Campbell, K. H. S. et al. (1996) "Sheep cloned by nuclear transfer from a cultured cell line" *Nature*

380, 64-66; Heyman Y, et al. (1998) "Cloning in cattle: from embryo splitting to somatic nuclear transfer." *Reprod Nutr Dev* 38(6):595-603; Loi P, et al. (1998) "Embryo transfer and related technologies in sheep reproduction." *Reprod Nutr Dev* 38(6):615-28). The technique of nuclear transfer includes several demanding aspects, two of which are the enucleation, or removal, of the genetic material from the recipient oocyte and the deposition of a donor nucleus in the enucleated oocyte.

Recent early stage research has shown that infertility for some women can be ameliorated by the transfer of a small quantity of cytoplasm taken from a donor oocyte from another woman, presumably one without any cytoplasmic deficiencies (Lanzendorfise; Mayer J F; Toner J, Oehningers, Saffan D S, Muashers (1999) "Pregnancy following transfer of ooplasm from cryopreserved-thawed donor oocytes into receipient oocytes" *Fertility and Sterility* 74(3):575-7).

The rigors of the physical manipulation of these cells during the generation of transgenic animals, intracytoplasmic sperm injection, assisted hatching, enucleation, nuclear transfers and cytoplasmic transfer as well as the sheer enormity of the demand that these procedures place on technical staff represents two of the main reasons for failure. Thus, any improvements to these procedures which result in higher rates of success as well as increased capacity for processing is of great value.

SUMMARY OF THE INVENTION

The present invention provides for MEMS devices useful in the labeling and manipulation of oocytes or embryos including: (1) Cell Labeling MEMS Devices, (2) Labelable Zona Anchor MEMS Devices, (3) Microinjection MEMS Devices; (4) ICSI MEMS Devices; (5) Zona Coring MEMS Devices; (6) Enucleation MEMS Devices; (7) Enucleation/Nuclear Transfer MEMS Devices; and (8) Cytoplasmic Transfer MEMS Devices. The present invention also provides for kits comprising the above devices.

The present invention also relates to devices or articles of manufacture to be used for the manipulation and use of the MEMS devices including centrifugal platters, Labelable Zona Anchor MEMS device platforms, Labelable Zona Anchor MEMS device platform holders; Automated Multi-Compartment, Multi-Modal Incubators; Single Layer Culture MEMS Arrays, Multi-layer Culture MEMS Arrays; Multi-layer Culture Array Environmental Controllers, and Automated Environmental Instruments.

Also, the present invention provides for methods of using the above-identified devices, arrays, controllers and instruments.

Further, the present invention provides for methods of making the above-identified MEMS devices and kits.

The present invention is based, at least in part, on the novel application of microelectromechanical systems to the modification, immobilization, translocation, and modulation of cells or groups of cells such as culture cells, oocytes, embryos, and sperm.

Whereas many cells in the body are of a size on the order of a few microns, there is a special class of cells, the female gamete called the oocyte, which is far larger, on the order of 100 microns. Further, these cells, in many animals from sea urchins to mammals, are surrounded by a five to twenty micron thick selectively permeable glycoprotein coat called the "Zona Pellucida" or "Zona". The modification of the surface of the glycoprotein coating of oocytes and embryos is a desirable operation in endeavors such as the labeling of a great many of oocytes and embryos in the animal husbandry industry.

Further, the ability to manipulate and confine oocytes and embryos to a specific location for the culture before, during, and after assisted reproduction procedures is necessary and quite time consuming as well as requiring dedicated and highly trained technical staff.

The rigors of the physical manipulation of these cells during assisted reproduction procedures as well as the sheer enormity of the demand that these procedures place on technical staff represents two of the main reasons for failure. Any improvements in terms of efficiencies to these procedures which result in higher rates of success as well as increased capacity for processing is of great value.

Methodologies for the tracking of oocytes and embryos during isolation and manipulation for purposes such as animal husbandry, embryo tagging, and tracking of manipulated or treated oocytes over time and through space are rudimentary at present. Current protocols utilize the segregation of oocytes and embryos into individual wells or drops of culture medium entrapped under inert oil layers. The viablility of cultured oocytes and embryos is enhanced by the co-culture of several oocytes or embryos within a relatively small volume. A device which would facilitate the identification of an individual oocyte or embryo distinctly from other oocytes or embryos would allow the co-culture of many differently treated or coded oocytes or embryos in one volume of media. Further, the ability to permanently label a particular oocyte or embryo in such a way as to allow coding of the treatment of each oocyte or embryo into the label is desirable.

It is an object of the invention to provide MEMS devices, kits, and methods of uses thereof, to enable rapid and easy manipulation of cells or groups of cells including but not limited to culture cells, oocytes, embryos, or sperm. More specifically, the present invention allows for an automated method of manipulating cells which does not rely heavily upon the ability of the person performing the manipulation. Further, the present invention allows for the manipulation of many cells simultaneously.

More particularly, it is an object of the invention to provide MEMS devices, and kits, for labeling cells or groups of cells, in particular oocytes and embryos for easy identification and ease of manipulation. It is another object of this invention to provide MEMS devices, kits and methods of use for the following:

1. microinjection of material such as a nucleus or cytoplasm into a donor cell or group of cells;
2. intracytoplasmic sperm injection to introduce sperm into an oocyte to facilitate fertilization;
3. enucleation of a cell or group of cells to create a recipient cell for nuclear transfer to enable "cloning";
4. nuclear transfer to facilitate insertion of a nucleus from a donor cell into a recipient cell to enable "cloning";
5. cytoplasmic transfer for the transfer of cytoplasmic material from one cell to another to reduce infertility of oocytes or embryos;
6. zona coring for introducing holes or taking cores of the zona pellucida to improve fertility; and
7. cell culture of cells or groups of cells especially in the field of in vitro fertility methods and implantation.

It is another object of the invention to provide methods of making the MEMS devices and kits.

BRIEF DESCRIPTION OF THE DRAWINGS

The various figures are schematic and not drawn to scale.

FIG. 2A is a perspective view of a base silicon wafer to be used in a Cell Labeling MEMS Device showing the channels in the wafer.

FIG. 2B is a perspective view of second silicon wafer showing the regions etched/deposited or otherwise modified.

FIG. 2C is a side view and partial see-through view of a Cell Labeling MEMS device showing the cell wells and the labelable zona anchor MEMS device at the base of the well.

FIG. 2D is a perspective view and partial cross-sectional view of the Cell Labeling MEMS device showing the cell wells and labelable zona anchor MEMS device within.

FIG. 2E is a top view of a number of MEMS devices attached to a centrifugal platter next to Cell Labeling MEMS devices with oocytes or embryos loaded thereto.

FIG. 3A is a side edge view of a docking MEMS for docking labeled cells having a labelable zona anchor MEMS device.

FIG. 3B is an end view of a docking MEMS device with cells having labelable zona anchor MEMS devices attached to the platform of the docking MEMS device.

FIG. 3C is a side edge view of a male docking MEMS device showing cells with labelable zona anchor MEMS devices attached thereto positioned in a platform channel.

FIG. 3D is an end view of a male docking MEMS device with labeled cells attached in platform channels.

FIG. 4A is a side cross-sectional view of a MEMS platform holder.

FIG. 4B is a side view of the plunger during transport of the cells.

FIG. 4C is a side view of the plunger of the platform holder during intrauterine deposit of oocytes/embryos.

FIG. 15 is a top schematic view of a channel etched base plate with peizoelectric pump manifold array MEMS.

FIG. 16 is perspective view of a centrifugal platter for receiving a MEMS device.

FIG. 17 is a top cross-sectional view of a microinjection MEMS device.

FIG. 18 is a side cross-sectional view of the dynamic hydropressure column of a microinjection MEMS device.

DETAILED DESCRIPTION OF THE INVENTION

Figure 1:
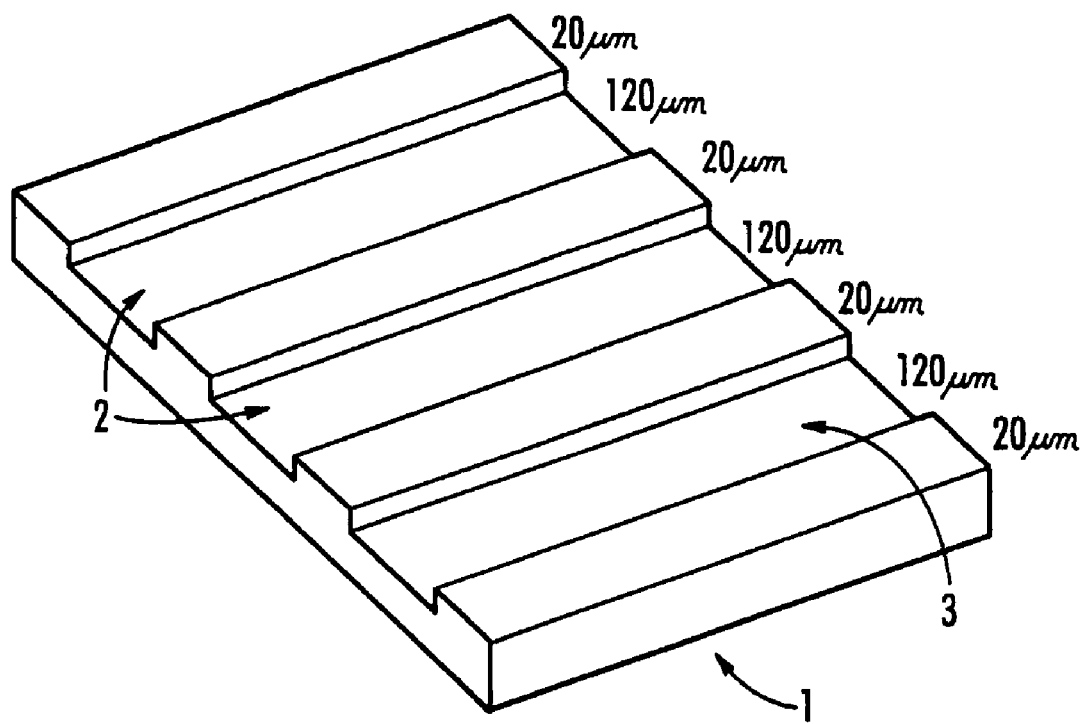
FIG. 1 is a perspective view of a first silicon wafer to be used in a Cell Labeling MEMS Device.

The present invention provides microelectromechanical systems (MEMS) devices and kits for the manipulation of a cell or groups of cells, including but not limited to, primary cells, culture cells, oocytes, embryos or sperm. The cells can be from any organism. In a preferred embodiment, the cells are from animals. In a most preferred embodiment, the cells are from humans. The present invention also provides for methods of using the devices and kits for manipulation of a cell or group of cells. Further, the present invention provides methods of making the MEMS devices described herein.

The present invention provides cell labeling MEMS devices and kits useful for labeling individual cells or groups of cells. The cell labeling MEMS device enables one to label a cell or group of cells, including but not limited to oocytes or embryos, with a labelable zona anchor MEMS device. The labeled cells allow one to easily identify the cells and facilitates further manipulations. For example, the labeled cells allow for the tracking of oocytes to prevent in vitro fertilization with the wrong sperm or to prevent the implantation of the wrong embryos into a patient.

The labelable zona anchor MEMS devices are attached or anchored to the cell or group of cells. For example, the labelable zona anchor MEMS device can be attached or anchored to the zona pellucida of oocytes or embryos.

In another aspect, the present invention provides for arrays and incubation devices useful for cell culture and handling. In particular, the present invention provides for automated multi-compartment, multi-modal incubators, single layer and multi-layer culture arrays, multi-layer culture array environmental controllers, and environmental control instrument.

In yet another aspect, the present invention provides for labelable zona anchor MEMS device platforms and labelable zona anchor MEMS device platform holders useful for the manipulation and implantation of labeled cells or groups of cells into an animal.

The present invention also provides microinjection MEMS devices and kits, methods of their use and methods of making the devices and kits. The microinjection MEMS devices are useful for the microinjection of material or nuclei into a cell or group of cells.

The present invention provides for intracytoplasmic sperm injection ("ICSI") MEMS devices and kits, methods of their use, and methods of making the same. The ICSI MEMS devices are useful for the injection of a sperm into an oocyte.

The present invention provides for zona coring MEMS devices and kits, methods of their use, and methods of making the devices. The zona coring MEMS devices are useful for the creation of "holes" or "cores" in the zona pellucida of oocytes and embryos to improve the ability of the embryo to escape the confines of the zona and implant in the uterine lining.

The present invention provides for enucleation MEMS devices and kits, methods of their use and methods of making the devices. The enucleation MEMS devices are useful for removing the nucleus from a recipient cell so that genetic material, a nucleus from another cell, or a cell may be inserted. Additionally, the enucleation devices are used to obtain genetic material or nuclei.

The present invention provides for an enucleation/nuclear transfer MEMS device and kits, methods of using, and methods of making the device. The enucleation/nuclear transfer MEMS devices are useful for performing enucleation of a recipient cell and the subsequent transfer of a cell or nucleus into the recipient cell.

The present invention provides for a cytoplasmic transfer MEMS device and kits, methods of using same, and methods of making. Cytoplasmic transfer MEMS devices are useful for the transfer of cytoplasmic material from a donor oocyte or embryo into a host oocyte or embryo.

Lastly, the present invention provides for cell culture MEMS devices, kits, methods of using same, and methods of making same, for culturing cells especially in conjunction with the other MEMS devices and methods described herein.

Solely for ease of explanation, the description of the invention is divided into the following sections: (A) Making MEMS; (B) Cell Labeling MEMS; (C) Labelable Zona Anchor MEMS; (D) Labelable Zona Anchor MEMS Device Platforms; (E) Labelable Zona Anchor MEMS Device Platform Holders; (F) Automated Multi-Compartment, Multi-Modal Incubator; (G) Single Layer Culture Arrays; (H) Multi-Layer Culture Arrays; (I) Multi-Layer Culture Array Environmental Controllers and Environmental Controlled Instruments; (J) Microinjection MEMS; (K) ICSI MEMS; (L) Zona Coring MEMS; (M) Enucleation MEMS; (N) Enucleation/Nuclear Transfer MEMS; and (O) Cytoplasmic Transfer MEMS.

A. Making MEMS

The MEMS devices described herein can be manufactured using a variety of methods known and used in the art. For example, MEMS can be made using methods such as silicon bulk micromachining, LIGA, silicon surface machining, deep silicon reactive ion etching, dry etching, advanced deep reactive ion etching (ADRIE), or bulk anisotropic silicon etching. Micromachining methods are described in a number of references listed in the Background Section supra and incorporated herein by reference. Also, methods of micromachining are described in "Micromechanics and MEMS: classic and seminal papers to 1990," ed. William F. Trimmer (1997) (IEEE Press, New York), which is incorporated herein in its entirety.

Basically, MEMS devices are made by micromachining the components of the device to build, for example, sensors, micropumps, wells, micromotors, x-y stages and other "smart" devices. Additionally, components can be deposited on the MEMS substrate, such as, circuits, and controllers.

Devices ranging in size from a dozen millimeters to a dozen microns can be manufactured by using silicon bulk micromachining. This process uses either etches that stop on the crystallographic planes of a silicon wafer or etches that act isotropically to generate mechanical parts.

As used herein, the word "wafer" refers to a silicon disc slice from a crystal on which structures are manufactured, and a "wafer" is also called a "substrate" or "starting material." These techniques combined with wafer bonding and boron diffusion allows complex mechanical devices to be fabricated. The LIGA technology makes miniature parts with spectacular accuracy. Electro Discharge Machining, EDM, extends conventional machine shop technology to make sub-millimeter sized parts.

As used herein, "LIGA" or "Lithographie, Galvanoformung, Abformung" refers to the process by which polymethyl methacrylate (PMMA) plastic is exposed to synchrotron radiation through a mask. Exposed PMMA is then washed away, leaving vertical wall structures with great accuracy. Structures a third of a millimeter high and many millimeters on a side are accurate to a few tenths of a micron. Metal is then plated into the structure, replacing the PMMA that was washed away. This metal piece can become the final part, or can be used as an injection mold for parts made out of a variety of plastics.

"Silicon surface micromachining" refers to the process by which layers of sacrificial and structural material are deposited on the surface of a silicon wafer. Further, as each layer is deposited on the wafer, it is patterned, leaving material only where the designer wishes. When the sacrificial material is removed, completely formed and assembled mechanical devices remain.

"Deep silicon reactive ion etching" or "Deep Si RIE" or "DRIE" is an art-recognized term and refers to the process by which highly anisotropic, randomly shaped and located features are patterned and etched into a single crystal silicon wafer, with only photoresist as an etch mask. As used herein, "mask" is an art known term and includes the fabrication process whereby each layer of the process is photographically transposed onto the wafer so that a deposition can be accurately placed within selected areas of the wafer. Deep Si RIE can be used to etch both shallow and deep features into the front side and back side of a wafer, and can also be used to etch completely through the wafer, to produce holes, diaphragms, or suspended structures. Deep Si RIE can also produce high aspect ratio features.

Dry etching technology is useful for fabricating three-dimensional building blocks for MEMS applications. The fabrication technique of these blocks demand etching processes with high etch rate and selectivity, both for bulk- and surface micromachining. Low ion energy prevents substrate damage to electronics, mask erosion (the selectivity to metal masks is practically infinite), and makes it easy to change the profile of the trench.

Some silicon bulk micromachined devices require backside-to-frontside photolithographic alignment fabrication processes. This process is typically used to align cavities etched from the backside of the wafer to structures located on the front side of the wafer. Substrates are rendered ultra-flat prior to bonding. After bonding, chemical/mechanical grinding and polishing, chemical etching, and plasma assisted chemical etching are used, as appropriate, for thinning to final dimension.

The application of ultraviolet sources in photo-assisted processing affords the ability to use the chemical effects induced by high energy photons, as opposed to the thermal effects of high intensity beams, for high specification lithography and microfabrication processes with minimal damage. The ability of the deep ultraviolet 193 nm wavelength of the ArF excimer laser to ablate glass without damage due to thermal stresses below the surface of the material is well known.

B. Cell Labeling MEMS

The present invention encompasses cell labeling MEMS devices comprising a substrate (i.e., silicon wafer, plastic, metal oxides) which have been manufactured to comprise at least one well or a plurality of wells for receiving at least one cell or group of cells, such as but not limited to, an oocyte or embryo, and a labelable zona anchor MEMS device. The cell labeling MEMS devices provides a device for attaching or anchoring labelable zona anchor MEMS devices (labels) into cells or groups of cells.

In one embodiment, the cell labeling MEMS device comprises:

(a) a first composite silicon wafer comprising:
a plurality of channels along the length of the wafer; and
(b) a second silicon wafer bonded to the first composite silicon wafer comprising a plurality of wells wherein the wells comprise a labelable zona anchor MEMS device. The channels provide for a non-bonded or empty space behind the labelable zona anchor MEMS devices to allow for easy detachment from the device so they will anchor into the cell or group of cells to be labeled.

In a specific embodiment, the cell labeling MEMS devices of the present invention comprises a labelable zona anchor MEMS device attached to the well by a break-away means. The break-away means includes any material that is continuous with the label and the rest of the MEMS device that will fail from mechanical stress as cell cell moves out of the MEMS device cell well, allowing the label to remain embedded in the zona.

In other specific embodiments, the channels of the cell labeling MEMS devices are from about 2 to about 5 microns deep (more particularly, about 2 μm, about 3 μm, about 4 μm, or about 5 μm) and range from about 90 to about 150 microns long (more particularly, about 90 μm, about 100 μm, about 110 μm, about 120 μm, or about 150 μm).

In yet another specific embodiment, the cell labeling MEMS device comprises channels separated by from about 5 to about 50 microns (i.e., 5 μm, 10 μm, 15 μm, 20 μm, 50 μm).

In a more specific embodiment, the wells of the cell labeling MEMS devices are from about 50 to about 150 microns wide (more particularly about 50 μm, about 75 μm, about 90 μm, about 100 μm, about 120 μm, or about 150 μm).

In yet another specific embodiment, the cell labeling MEMS device further comprises an incomplete circle inscribed about the labelable zona anchor MEMS device ranging from about 0.5 to about 5 microns in width (more specifically, about 0.5 μm, about 1 μm, about 1.5 μm, about 2 μm, or about 5 μm).

The present invention also pertains to a method of making a cell labeling MEMS device comprising at least one labelable zona anchor MEMS device per well.

In a preferred embodiment, the method of making a cell labeling MEMS device is a method wherein a wafer base or substrate is modified in a way such that a plurality of cell wells are formed that contain a structure within them that consists of a barb or a plurality of barbs attached to a planar element. In another embodiment, said planar element is located within said plurality of cell walls and attached to a barb or a plurality of barbs, is not permanently attached to the structure of said cell wells. In another embodiment, a means is provided within said cell wells for a controlled burst of gas or fluid to be produced thus facilitating the evacuation of cells resident in said cell wells.

The wafer base substrate of the all labeling device can be made of a variety of materials known in the art.

In particular preferred embodiments, the wafer or base substrate of the cell labeling MEMS device is composed silicon, sapphire, polymer, metallic compounds, or a multi-laminate material.

Referring to FIG. 1, there is shown a wafer or base substrate 1 of a cell labeling MEMS device. Channels 2 of uniform dimensions and varying from about 0.01 μm to about 5 μm in depth and varying from about 1 μm to about 200 μm in width are etched across the length of said base wafer 1. Further, in referring to FIG. 1, a layer of sacrificial material 3 is deposited in the channels 2. Sacrificial materials are known in the art and can be, for example, but not limited to silicon dioxide, deposited oxide, photoresist, amorphous silicon, polysilicon, or aluminum.

Figure 2F:
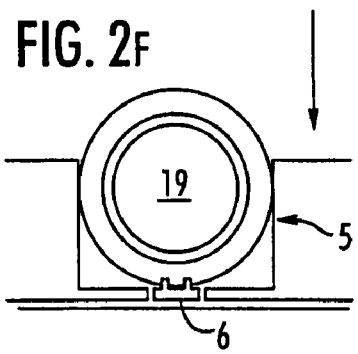
FIG. 2F is a side cross-sectional view of a cell well of a labelable zona anchor MEMS device showing a label being attached to a cell.
Figure 2K:
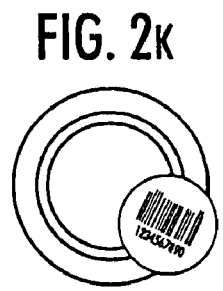
FIGS. 2G-2K are schematic drawings of labeled cells with Labelable Zona Anchor MEMS devices attached thereto.
Figure 2G:
Figure 2L:
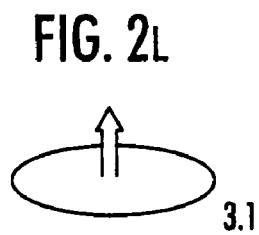
FIGS. 2L-2O are drawings of labelable zona anchor MEMS devices having a variety of types of anchors.
Figure 2H:
Figure 2M:
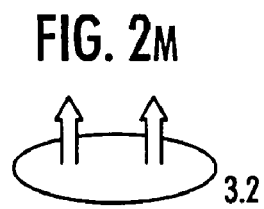
Figure 2I:
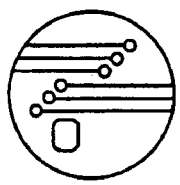
Figure 2N:
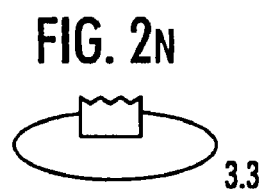
Figure 2J:
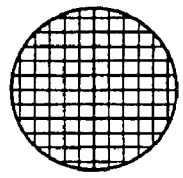
Figure 2O:
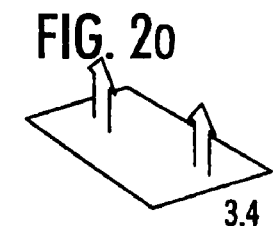

Referring to FIGS. 2A-E, there is shown in FIG. 2-A a first silicon wafer or base substrate 1 (same as in FIG. 1): FIG. 2B shows a second wafer 11 regions 15 etched/deposited or otherwise modified (e.g., polymerized), FIG. 2C shows a slice of a cell labeling MEMS device; FIG. 2D shows a first wafer 1 fused to a second silicon wafer 11 forming megalaminate 16; and cell labeling MEMS device 7 mounted on a centrifugal platter 8. The second silicon wafer 11, being modified on one surface with etching or deposition of materials or other modifications, is bonded, (i.e., silicon fusion bonded) to the first silicon wafer 1 such that the modified second silicon wafer 11 top surface 4 is in contact with the sacrificial material 3 in the channels in the base wafer 1. This bonding forms a boundary, (i.e., a silicon fusion bonding interface) 12. After adhesion of the first silicon wafer 1 and the second silicon wafer 4, wells 5 are etched to an intermediate depth whereupon masks and etches create a labelable zona anchor MEMS device 6 within the wells 5. Alternatively the labelable zona anchor MEMS devices can be made separately and deposited in the wells. The multi-welled mega-laminate structure so formed is cut such that a single well or row of wells 7 occurs. This single row unit 7 is mounted onto a centrifugal platter 8 such that the opening of the wells 5 face the center of the centrifugal platter 8. As shown in FIG. 2E, upon rotation 9 of the centrifugal platter 8 a centripetal force 10 is exerted perpendicularly from the center of the centrifugal platter 8 outward. This force 10 exerts perpendicularly against the far wall 13 of the wells 5. As shown in FIG. 2F, cells 14 present near the wells 5, upon rotation 9 of the centrifugal platter 8, are thrust into the well 5 onto the far wall 13 such that the labelable zona anchor MEMS device 6 penetrates the cell 14 or group of cells.

In one embodiment, a plurality of cell labeling MEMS devices are permanently attached to a centrifugal platter for providing force along the long axis of the wells of the cell labeling MEMS devices.

As used herein, the term "centrifugal platter" refers to a structure which is mainly planar and which has a securing means for securely attaching to a driver means.

A centrifugal platter may be composed of a material that is sufficiently rigid that it will support the affixing of a MEMS device of the present invention, is non-corrosive, is non-toxic to cells (e.g., culture cells, oocytes, embryos) and can be sterilized (e.g., gamma irradiation, autoclaving). Such materials may be silicon and plastic. A centrifugal platter may also be so constructed such that there is no material at it's center of rotation (e.g., analogous to an optical media disk commonly known as a compact disk).

A securing means would be an element resident on a spinner apparatus that momentarily (e.g., not permanently) attaches to the centrifugal platter (e.g., gripping the inner edge of the center opening or on the outer edges of the disk) so that the centrifugal platter is held firmly to the rotating member of the spinner.

In one embodiment, a centrifugal platter for applying a centripetal force to a cell or group of cells contained within a MEMS device comprises a circular disk having a plurality of ports for holding the MEMS device.

In another embodiment, the cell labeling MEMS devices are permanently attached to a centrifugal platter for providing force along the long axis of the wells present on the wafer or base substrate and wherein said operating means comprises a centrifugal platter that is attachable to a driver means. The term "driver means" or "spinner" includes a platform that serves to securely hold a centrifugal platter of the present invention and that is operably attached to an instrument that provides for the rotation of the driver means (i.e., a centrifuge, a rotating sputterer instrument as used in semi conductor fabrication).

In another embodiment, a driver means exerts a force on the centrifugal platter such that the centrifugal platter revolves and thereby providing an outward centripetal force to the attached cell labeling MEMS device and/or the labelable zona anchor MEMS devices. In yet another embodiment, a centrifugal platter comprises a plurality of depressions in direct contact with the cell labeling anchor MEMS devices. In particular, a centrifugal platter comprises one or more depressions or wells in the immediate vicinity of one or more affixed MEMS devices of the present invention wherein each depression or well is in fluid communication with exactly one affixed MEMS device. These depressions or wells provide for the placement of only on oocyte or embryo next to each MEMS device. Further, these depressions or wells restrict the movement of the oocytes or embryos from one MEMS device to another, avoiding multiple manipulations to a single oocyte or embryo.

In a more specific embodiment, the centrifugal platter comprises a conductive material which serves as a circuit between the cell labeling MEMS devices and the driver means. The conductive material of the centrifugal platter enables the rotation of the platter by the driver means to be controlled. In particular, the conductive materials (e.g., circuit lead or a strip of conductive material resident on the centrifugal platter and in communication with the circuit leads resident on the MEMS devices) are in contact with a portion of the spinner (driving means) that provides data transmission and current, thus providing this data transmission and current, by way of the circuit leads, to the MEMS devices.

In the present invention, upon application of centripetal force to the cell labeling MEMS devices, the labelable zona anchor MEMS device contacts and anchors into the cells or groups of cells. In a specific embodiment, the labelable zona anchor MEMS device anchors into and modifies the surface of the zona pellucida surrounding oocytes and embryos.

In the preferred embodiment, upon application of centripetal force, the labelable zona anchor MEMS device penetrates the zona pellucida but does not pass through the zona pellucida.

The present invention also encompasses a cell labeling MEMS device kit comprising:
  a) a centrifugal platter for applying a centripetal force to a cell or group of cells contained within a MEMS device wherein the centrifugal platter comprises a circular disk, a plurality of ports for affixing the MEMS devices, and a securing means for securing the centrifugal disk to a spinner or driving means; and
  b) at least one cell labeling MEMS device.

In another preferred embodiment, a cell labeling MEMS kit for applying a labelable zona anchor MEMS device to a cell or group of cells comprising:
  (a) a centrifugal platter having an outer edge and a plurality of grooves, the grooves having an inner and outer surface, arranged in a concentric pattern on the surface of the centrifugal platter; and
  (b) at least one cell labeling MEMS device of claim 1 or 19; wherein the cell labeling MEMS device is attached to the outer edge of the compact centrifugal platter in an orientation such that the long axis of each of the wells of the cell labeling MEMS device is horizontal to plane of the centrifugal platter and the inner surface of the grooves forming divided chambers, the chamber containing a single well, which restrict the movement of materials from chamber to another such chamber.

The present invention also provide for a method of using a cell labeling MEMS kit above comprising:
  (a) filling the grooves of the centrifugal platter with a fluid;
  (b) loading the fluid within the grooves of the centrifugal platter with at least one cell or group of cells; and
  (c) applying centripetal forces to the centrifugal platter by rotation such that the cell or group of cells is thrust against the wall of well such that the embedding means of the labelable zona anchor MEMS device penetrates the surface of the cell.

In a preferred embodiment, the cell labeling MEMS kit comprising:
  (a) at least one cell labeling MEMS device; and
  (b) a centrifugal platter having an outer edge and a plurality of grooves, the grooves having an inner and outer surface, arranged in a concentric pattern on the surface of the centrifugal platter; wherein the cell labeling MEMS device is attached to the outer edge of the centrifugal platter in an orientation such that the long axis of each of the wells of the cell labeling MEMS device is horizontal to plane of the centrifugal platter and the inner surface of the grooves forming divided chambers, the chamber containing a single well, which restrict the movement of materials from chamber to another such chamber.

The present invention further encompasses a method of using a cell labeling MEMS kit comprising:

(a) filling the grooves of the centrifugal platter with a fluid;

(b) loading the fluid within the grooves of the centrifugal platter with at least one cell wherein the cell has a zona pellucida; and (c) rotating the kit using a driver means such that centripetal forces are applied to the centrifugal platter such that the cell is thrust against the wall of the well such that the embedding means of the labelable zona anchor MEMS device penetrates the surface of the zona pellucida of the cell.

In a more specific embodiment, the cell labeling MEMS device is permanently affixed to a centrifugal platter.

The present invention further provides for methods of using the cell labeling MEMS devices and kits wherein a plurality of cell labeling MEMS devices have been attached temporarily or permanently to a centrifugal platter forming a cell labeling MEMS device kit, and comprising the steps of securing the centrifugal platter to a driving means and further whereby liquid is placed in the depressions present in said centrifugal platter directly next to said labelable zona anchor MEMS devices such that said liquid is in contact with the wells of the labelable zona anchor MEMS devices and further cells (e.g., oocytes, embryos) are placed in said liquid and subsequently said driver means provides a centripetal force to said centrifugal platter, cell labeling MEMS devices, and cells such that the liquid and cells migrate towards the outer margin of the centrifugal platter and, as such, into the wells of the cell labeling MEMS devices. In a specific embodiment, the anchor or anchors is a barb or a plurality of barbs.

In another embodiment, the zona pellucidas of the cells, upon migration into the cell labeling MEMS devices, are penetrated by the anchor or anchors of the labelable zona anchor MEMS devices such that the anchor or anchors of the labelable zona anchor MEMS devices are embedded in the zona pellucidae of said cells.

Upon completion of using the cell labeling MEMS device, the labelable zona anchor MEMS devices remain embedded in the zona pellucidae of said cells upon the cessation of the centripetal force as applied by the driver means.

In another embodiment, the kit further comprises a release means by which a controlled burst of gas or fluid is released within the wells of the cell labeling MEMS devices such that the cells with labelable zona anchor MEMS devices embedded within the zona pellucidae are ejected from cell labeling MEMS devices. The controlled burst of gas or fluid can be provided through a separate microfluidics channel in the kit and can be actuated by a pump to a fluid or gas into the well in order to assist in the release of the cell or group of cells from the well after the centripetal force has been applied.

C. Labelable Zona Anchor MEMS

The present invention also provides labelable zona anchor MEMS devices, and kits, methods of using same, and methods of making same.

In one embodiment, a labelable zona anchor MEMS device comprises at least one anchor and a labelable surface. As used herein, the term "labelable zona anchor MEMS device" refers to a micromechanical device which is so constructed as to provide at least one anchor which attaches to or anchors in the zona pellucida of a cell or group of cells, such as an oocyte or embryo and a labelable surface.

As used herein, the term "zona pellucida" refers to the glycoprotein matrix which encases the oocyte and embryo of a wide range of animal species.

In particular embodiments, the anchor or anchors of the labelable zona anchor MEMS are from about 5 to about 15 μm tall. In more specific embodiments, the anchors are about 5 μm tall, about 10 μm tall or about 15 μm tall.

In another embodiment, the labelable surface of the labelable zona anchor MEMS device is planar and attached to the anchors. In a preferred embodiment, the labelable surface is any geometric shape including but not limited to a circle, square, rectangle, polygon, etc. and can be from about 0.5 to about 30 μm in diameter. More particularly, the labelable surface is about 0.5, about 1, about 5, about 10, about 20 or about 30 μm in diameter.

In the present invention, the labelable zona anchor MEMS device further comprises on the labelable surface, which is not directly opposed to the zona pellucida, a label. In yet another embodiment, the labelable surface further comprises a distinctive modification that serves as a label. A label can be any item that serves to identify one labeled cell or group of cells from another. In a preferred embodiment, there is at least one label on the labelable surface.

In one embodiment, the distinctive modification or label on the labelable surface of the labelable zona anchor MEMS device comprises a plurality of etched grooves forming a unique etched grooved pattern, by which a code may be assigned to each unique etched grooved pattern.

In another embodiment, the label comprises a plurality of deposited grooves, forming a unique deposited pattern, by which a code may be assigned to each unique deposited grooved pattern.

In yet another embodiment, the label comprises comprised of a circuit. In a more specific embodiment, the circuit facilitates the storage of information (i.e., physical parameters, changes in physical parameters over time, movement through time, movement through space, origin of cell, ownership of material, certification of status of the cell or group of cells). In another embodiment, the circuit functions as a transponder.

In another embodiment, the surface of the labelable zona anchor MEMS device comprises of a magnetically-attractive surface including, but not limited to a metallic coating.

In another embodiment, the label comprises a fluorescent material or fluorophore. For example, the fluorescent material includes but is not limited to rhodamine, fluorescein, Cy3, Cy5, or other such fluorophores known to those in the art. Examples of such fluorescent materials or fluorophores include, but are not limited to, fluorescein, BODIPY®, TRITC, Lissamine™, rhodamine, Texas Red®, Cy-3.18™, Cy-5.18™, Lucifer Yellow, Lucifer Yellow, Ethidium bromide, Propidium iodide, Di-I, Calcium Green™, Calcium Orange™, Calcium Crimson™, SNARF®-1, AND SNAFL®-1. Additional examples of fluorescent materials are Dabcyl, Cy2 Green, Fluorescein (FITC) Green, FAM (Carboxyfluorescein) Green, TET (Tetrachlorofluorescein) Orange, HEX (Hexachlorofluorescein) Pink, TAMRA (Carboxytetramethyl rhodamine) Rose, Cy3.5 Scarlet, ROX (carboxy--x-rhodamine) Red, Malachite Green, Far Red, Near-IR (max. abs. 675 or 743), Fluor X Green, AMCA-S, Cascade Blue, BODIPY FL, CODIPY 530/550, BODIPY 493/503, BODIPY 558/569, BODIPY 654/570, BODIPY 576/589, BODIPY 581/591, BODIPY FL X, BODIPY R6Gx, BODIPY 630/650 X, Marine Blue, Pregon Green 500 Green, Oregon Green 514 green, Oregon Green 488 green and Pacific Blue.

In another embodiment, the labelable zona anchor MEMS device comprises at least two labels in any combination of an etched bar code, a deposited bar code, an integrated circuit, a magnetically attractive substance, and a fluorescent marker.

FIGS. 2G-2K show several embodiments of labelable zona anchor MEMS devices. Labelable zona anchor MEMS can be variably labeled, for example, but not limited to, a universal product code deposited or etched on it's labelable surface 2G, a logo deposited or etched on it's labelable surface 2H, a circuit 2I deposited or etched on it's surface, a surface coating 2J applied to it's labeleable surface. An oocyte or embryo with a labeleable zona anchor MEMS anchored in it's zona is also shown 2K.

FIGS. 2L-2O show how labelable zona anchor MEMS devices can have a variety of anchors including but not limited to, one barbed protuberance, two or more barbed protuberances, a serrated blade, a non-circular labelable zona anchor MEMS with one or more barbed protuberances.

The labelable zona anchor MEMS devices are made using standard manufacturing methods known in the art of MEMS. Methods used in making MEMS devices are described above in Section A. In one embodiment, the labelable zona anchor MEMS device is manufactured at the same time as the cell labeling MEMS device is produced. Alternatively, labelable zona anchor MEMS devices can be made independently and inserted into the wells of a cell labeling MEMS device, or some other cell handling means. For example, another cell handling means is an enclosed channel comprising labelable zona anchor MEMS devices attached to the walls of the enclosed channel, whereby cells or groups of cells are labeled by passing through the enclosed channel and coming into contact with the labelable zona anchor MEMS devices.

In one embodiment, the labelable zona anchor MEMS devices are made during the same process of making the cell labeling MEMS devices as described above in section B. In another embodiment, the labelable zona anchor MEMS device is made independently and deposited into the well of a cell labeling MEMS device. Methods of making MEMS devices are discussed in Section A supra.

In one embodiment, a method of making a labelable zona anchor MEMS device comprises the steps of:
1. orienting a substrate wherein the substrate has a bottom surface and a top labelable surface;
2. applying a mask to the bottom surface of the substrate;
3. etching the mask to form at least one anchor; and
4. applying a label to the top labelable surface of the substrate.

In another embodiment, the method of making a labelable zona anchor MEMS device further comprises the fusion of a channel-etched plate to the labelable surface.

D. Labelable Zona Anchor MEMS Device Platform

The present invention encompasses labelable zona anchor MEMS device platforms for the holding and transporting of labeled cells or groups of cells, such as oocytes or embryos.

As used herein, the term "labelable zona anchor MEMS device platform" (also referred to herein as a "platform") refers to a structure which is so constructed as to provide support and a variably attractive attachment substrate for a labelable zona anchor MEMS device. For example, the platform can be instructed or induced to cease attraction to the labelable zona anchor MEMS devices, facilitating the removal of labeled cells from the platform. Basically, this means that the platform is an inducible electromagnet. When you want the cells to stick you apply current to the platform, to remove you shut off the current.

In one embodiment, the labelable zona anchor MEMS device platform comprises at least one attaching element for attaching to a plurality of labelable zona anchor MEMS devices.

In particular, the attaching element may be a strip of magentized material (e.g., a metallic strip) that lies along the length of the platform that is an inducible magnet. In one embodiment, that attaching element (e.g., a metallic strip), if corrosive, is coated with a non-insulating non-corrosive material (e.g., a plastic coating). Also, the entire platform may have embedded within it a electromagnetic coil.

The platforms can be made from a variety of materials known and available to those in the art. In a specific embodiment, the labelable zona anchor MEMS device platform is composed of rigid material. In another specific embodiment, the labelable zona anchor MEMS device platform is composed of a non-corrosive material. In yet another specific embodiment, the labelable zona anchor MEMS device platform is composed of a material which is opaque to ultrasonographic detection to mediate localization internal to a recipient uterus during transfer of oocytes and/or embryos.

In a preferred embodiment, the labelable zona anchor MEMS device platform is a cylindrical or a rectangular object that can be made of plastic, metal or other non-corrosive, ultrasound-opaque material. The platform is preferably about 1 mm to about 20 mm in length and about 1 mm to about 10 mm wide. In more particular embodiments, the length of the platform is about 1 mm, about 5 mm, about 10 mm, about 15 mm or about 20 mm in length. In other particular embodiments, the platform is about 1 mm, about 5 mm or about 10 mm in width.

In a particular embodiment, the labelable zona anchor MEMS device platform comprises a docking domain on each end which facilitates the attachment of the platform to a external movable plunger. More particularly, an "external plunger" may include a structural element that forms one end of the platform holder that holds a platform internal to the container and that can be pushed further into the container thus pushing the docked platform partially out of the container. This functionality facilitates the extension of the platform out of the container (e.g., while the holder is inside the uterus) allowing the cells, when released from magnetic attraction to the platform, to float free into the environment surrounding the platform.

In other embodiments, the platform has two ends that are tapered for docking into a labelable zona anchor MEMS device platform holding device. In preferred embodiments, the docking domains protrude outwards or are "male" docking domains. In another preferred embodiment, the docking domains recede inwards or are "female" docking domains.

FIGS. 3A-3D, show a labeled cell and two different embodiments of a labelable zona anchor MEMS platform. In FIG. 3A, a labeled cell 19, being embedded with a labelable zona anchor MEMS 6, is selectively attracted to a labelable zona anchor MEMS platform 16 (shown here with multiple labeled cells). FIG. 3A shows the side view of a platform 16 having a male docking domain on each end. FIG. 3B shows the end view of a platform 16 illustrating the manner that a labeled cell 19 sits on platform 16. FIG. 3C edge view of platform 16 illustrating the manner that labeled cells 19 sit in the platform channel 18. FIG. 3C shows the edge view of platform 16 illustrating that each end of platform 16 has a male docking domain 17. FIG. 3D shows the end view of a platform 16 illustrating the manner that the labeled cells 19 sit in the platform channel 17.

In another preferred specific embodiment, the labeled cells or groups of cells are reversibly attached to the platform so that they may be released for further manipulation or for implantation into an animal.

The labelable zona anchor MEMS device platform is used by attaching labeled cells or groups of cells, such as oocytes or embryos.

The platform is made attractive by the induction of magnetism in the selectively magnetic securing means. This induction can be mediated by providing an electrical current (e.g., extremely low current) to the securing element. The securing element may include an electromagnetic coil.

The platform is then inserted into a labelable zona anchor MEMS device platform holder which allows for transporting the labeled cells without contamination. Then, either the cap is placed onto the open end of the platform for long term storage. The platform can be docked in a compartment of an automated multi-compartment multi-modal incubator (described in Section F infra) using the plunger to facilitate the engagement of the male or female docking domain at the platform with the reciprocal female or male docking domain of the incubator.

In particular, the plunger, being attached to the platform, pushes the platform out of the container and pushes the male or female docking domain into the reciprocal docking domain resident in the base of the compartment.

In yet another preferred embodiment, a labelable zona anchor MEMS device platform for holding cells or groups of cells labeled with labelable zona anchor MEMS devices comprises a supporting platform wherein the platform comprises a structural attaching element to which a plurality of labelable zona anchor MEMS devices attached to cells may be attached.

E. Labelable Zona Anchor MEMS Device Platform Holder

The present invention encompasses a labelable zona anchor MEMS device platform holder for transporting the labeled cells or groups of cells that are attached to the platform.

As used herein, the term "labelable zona anchor MEMS device platform holder" (also referred to herein as a "holder") refers to a structure that provides support for a labelable zona anchor MEMS device platform so that the platform can be transported and that such transport may include the co-transport of liquid surrounding the labelable zona anchor MEMS device platform and the labeled oocytes or embryos.

In a preferred embodiment, a labelable zona anchor MEMS device platform holder for holding a labelable zona anchor MEMS device platform comprises:
  a) an inner cylinder comprising a securing means for securing a labelable zona anchor MEMS device platform to the holder;
  b) a retractable outer cylinder for containing the inner cylinder; and
  c) a plunger mechanism for moving the inner cylinder and platform.

In one embodiment, the labelable zona anchor MEMS device platform holder comprises a docking domain for securely attaching a labelable zona anchor MEMS device platform. In preferred embodiments, the docking domains are a male or female docking domain.

In another embodiment, the labelable zona anchor MEMS device platform holder further comprises a container for containing a volume of liquid surrounding said labelable zona anchor MEMS device platform.

In one specific embodiment, the labelable zona anchor MEMS device platform holder further comprises a material which is disposable. In another specific embodiment, the holder comprises a material which is a polymer or a plastic. In yet another specific embodiment, the holder comprises a material that can be sterilized.

In another embodiment, the labelable zona anchor MEMS device platform holder further comprises a plunger by which the entire holder is manipulated either by hand or robotic device.

FIGS. 4A-4C show a labelable zona anchor MEMS platform holder in a partial side cross-sectional view, a side cross-sectional view, and schematic drawing of the device in-use, respectively. The labelable zona anchor MEMS platform holder 20 has an inner cylinder 21 with a female platform docking domain 22 that is attached to a plunger mechanism 23. This assembly is contained within a retractable outer cylinder or container 24. As seen in FIG. 4B, the labelable zona anchor MEMS platform holder has a cap 25 and is used during transporting in order to retain a fluid or culture media around a mounted platform within it. FIG. 4C, illustrates how the labelable zona anchor MEMS platform holder 20 is inserted into the vaginal vault 26, through the cervix 27, into the interior of the uterus 28, where the reversibly attached oocytes or embryos are released.

Figure 5A:
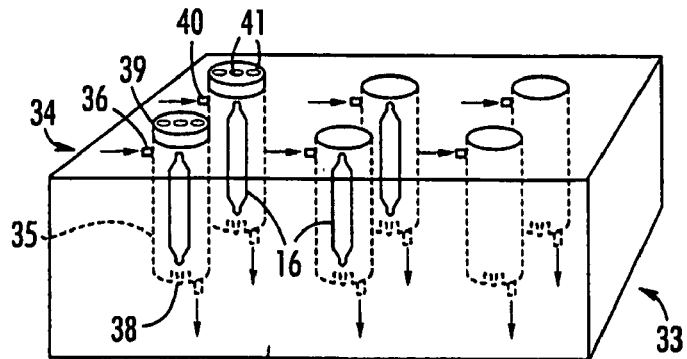
FIG. 5A is a side cross-sectional view of the automated multi-compartment multi-modal incubation device.
Figure 5B:
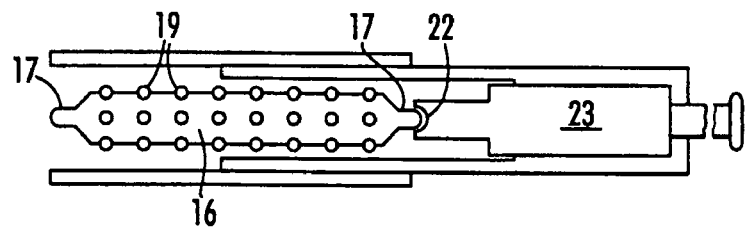
FIG. 5B is a side cross-sectional view of the platform holding device holding a platform.
Figure 5C:
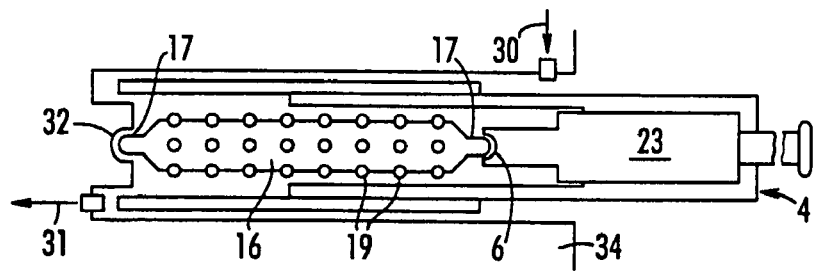
FIG. 5C is a side cross-sectional view of a platform holding device holding a platform.

FIGS. 5B and C show preferred embodiments of the platform and holder. FIG. 5B shows the labelable zona anchor MEMS platform holder during transport and has a female docking domain 22 resident on plunger 23 that receives and docks with the male docking domain 17 of the platform 16 which has a plurality of labeled cells attached thereto. FIG. 5C shows a platform 16 with labeled cells 19 within a compartment 29, its second male docking domain 17 being docked with the female docking domain 22 of the incubator compartment 29, wherein the compartment 29 has an input port 30 and an output port 31.

F. Automated Multi-Compartment, Multi-Modal Incubator

The present invention also pertains to an automated multi-compartment, multi-modal incubator. As used herein, the term "automated multi-compartment, multi-modal incubator" (also referred to herein as an "incubator") refers to a device that regulates and modulates the environment within a plurality of compartments which may contain a labelable zona anchor MEMS device platform which can contain at least one or a plurality of labeled cells or groups of cells such as oocytes and/or embryos that are attached to the labelable zona anchor MEMS device platform by way of zona-embedded labelable zona anchor MEMS devices.

In one embodiment, the automated multi-compartment, multi-modal incubator comprises a block comprising a plurality of compartments and a controlling means for regulating the environment within said compartments. In another embodiment, the automated multi-compartment, multi-modal incubator further comprises an incubator docking domain for attaching a labelable zona anchor MEMS device within each compartment. In specific embodiments, the incubator docking domains can be male or female docking domains.

In another specific embodiment, the controlling means of the automated multi-compartment, multi-modal incubator regulates conditions such as, but not limited to, compartment temperature, pH, the flow rate of input fluids or the flow rate of compartment output fluids. In more specific embodiments, the input or output fluids are culture media, a cell suspension, or a sperm suspension.

FIG. 5A shows an automated multi-compartment, multi-modal incubator 33, containing a labelable zona anchor MEMS platform holder during transport, which has a block 34 comprising one or more compartments 25. Each compartment 25 has an input port 36 and an output port 37, a female docking domain 38, and a cap 39 with input 40 and output ports 41.

FIG. 5C shows a multi-modal incubator 33 and a cross-sectional view of a labelable zona anchor MEMS platform holder 16 within an automated multi-compartment, multi-modal incubator 33.

Figure 5D:
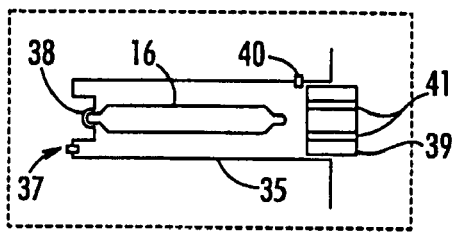
FIG. 5D is a cross sectional view of a compartment of an automated multi-compartment multi-modal incubator device containing a docking MEMS.

FIG. 5D shows a side cross-sectional view of a compartment 29 with a cap 32 showing a platform 16 docked and the compartment sealed with the cap 32.

In one embodiment, an automated multi-compartment, multi-modal incubator comprises:
(a) a block comprising a plurality of compartments;
(b) reagent reservoirs for containing a fluid reagent;
(c) fluid handling means communicating between compartments and reagent reservoirs;
(d) at least one environmental controlling means for regulating the environment within said compartments;
(e) a reagent input controlling means for regulating input of the fluid reagent from the reagent reservoirs into the compartments; and
(f) a fluid output controlling means for regulating output of fluids from compartments.

In yet another embodiment, an automated multi-compartment, multi-modal incubator for incubating cells or groups of cells that are attached to a labelable zona anchor MEMS device platform comprises:
1. a block comprising a plurality of compartments wherein each compartment receives a labelable zona anchor MEMS device platform;
2. a plurality of eagent reservoirs for containing a fluid reagent;
3. a fluid handling means communicating between the compartments and the reagent reservoirs;
4. at least one environmental controlling means for regulating the environment within said compartments;
5. a reagent input controlling means for regulating input of the fluid reagent from the reagent reservoirs into the compartments; and
6. a fluid output controlling means for regulating output of fluids from compartments.

The automated multi-compartment, multi-modal incubator is used as follows: the incubator is filled with appropriate fluids (i.e. culture media) and the incubator controller CPU (Central Processing Unit) is coded with desirable environmental parameters (i.e., temperature, pH, flow rate of fluids, in and out of compartments) and the system is allowed to reach the desired environmental parameters. At this point platforms (with labeled cells) are introduced into the incubator compartments by way of the platform holders described above. Once platforms are docked within the compartments, the compartments are sealed with caps. The incubator controller CPU is provided with desirable culture conditions and rates of change in those conditions over time. The incubator of the present invention allows for the culture and manipulation of labeled cells.

G. Single Layer Culture MEMS Array

The present invention also encompasses single layer culture MEMS arrays for culturing cells or groups of cells.

As used herein, the term "single layer culture MEMS arrays" (also referred to herein as "single layer arrays") refers to a layer wherein materials within the single layer array moves in an x-y axis. Such single layer arrays are constructed to allow the communication of culture materials between a plurality of single layer arrays such that materials move in an x-y-z axis. Further, the single layer arrays comprise a substrate or wafer (e.g., made of plastic, silicon, ceramic) on which is resident one or more enclosed channels that, in turn, each contains one or more movement tracks.

A single layer culture array of the present invention further comprises one or more collecting domains, one or more router elements resident on one or more movement tracks, and one or more main culture compartments. In another embodiment, the main culture compartment of the single layer culture array of the present invention comprises one or more movement tracks, and one or more router elements being resident on one or more movement tracks. In a more specific embodiment, the singe layer culture array of the present invention further comprises one or more enclosed input channels in fluid communication between a main culture compartment and an input fluid handling means of a controller unit.

As used herein, the term "enclosed channels" refers to a completely or partially enclosed open spaces within a single layer array through which materials such as oocytes, embryos and culture media may travel.

As used herein, the term "movement tracks" refers to a strip of material which is selectively attractive to labelable zona anchor MEMS devices and which is deposited onto a surface within an enclosed channel, collecting manifold or other surface. The movement tracks allow for the guided movement of the labeled cells through the array. As used herein, the term "routing elements" refers to a portion of a movement track which is selectively attractive to labelable zona anchor MEMS devices and which can mediate a change in the heading of a labelable zona anchor MEMS device, e.g., move the labelable zona anchor MEMS device onto another track.

As used herein, the term "collecting manifolds" refers to a region of a single layer array which is larger than an enclosed channel. Further, collecting manifolds may include a region of a single layer array which is larger than an enclosed channel and which is open on one side. The collecting manifold is for the introduction or removal of cells from the MEMS devices The culture manifold is an enclosed area or widened channel or channel that provides a location where a number of cells or groups of cells can be cultured together. More particularly, oocytes and embryos often survive or perform better when cultured together rather than individually. The culture manifold allows for such co-culture.

According to the present invention, a culture manifold comprises:
(a) an enclosed channel or a plurality of enclosed channels for receiving fluids or cells; and
at least one movement track traversing through the culture manifold for allowing movement of cells into the culture manifold. In a specific embodiment, a culture manifold comprises a plurality of movement tracks for transporting or allowing movement of a plurality of cells through the manifold.

In another specific embodiment, a culture manifold further comprises at least one input enclosed channel for introducing cells into the culture manifold.

In another embodiment, a culture manifold further comprises at least one output enclosed channel for removing cells from the culture manifold.

In yet another embodiment, the culture manifold further comprises at least one router element resides on a movement track.

As used herein, the term "externally communicating input and export channels" refers to a plurality of enclosed channels which lie above the plane of the single layer array, communicate with collecting manifolds and/or enclosed channels, may not contain movement tracks and which facilitate the movement of fluid into and out of the collecting manifolds or enclosed channels.

Figure 6A:
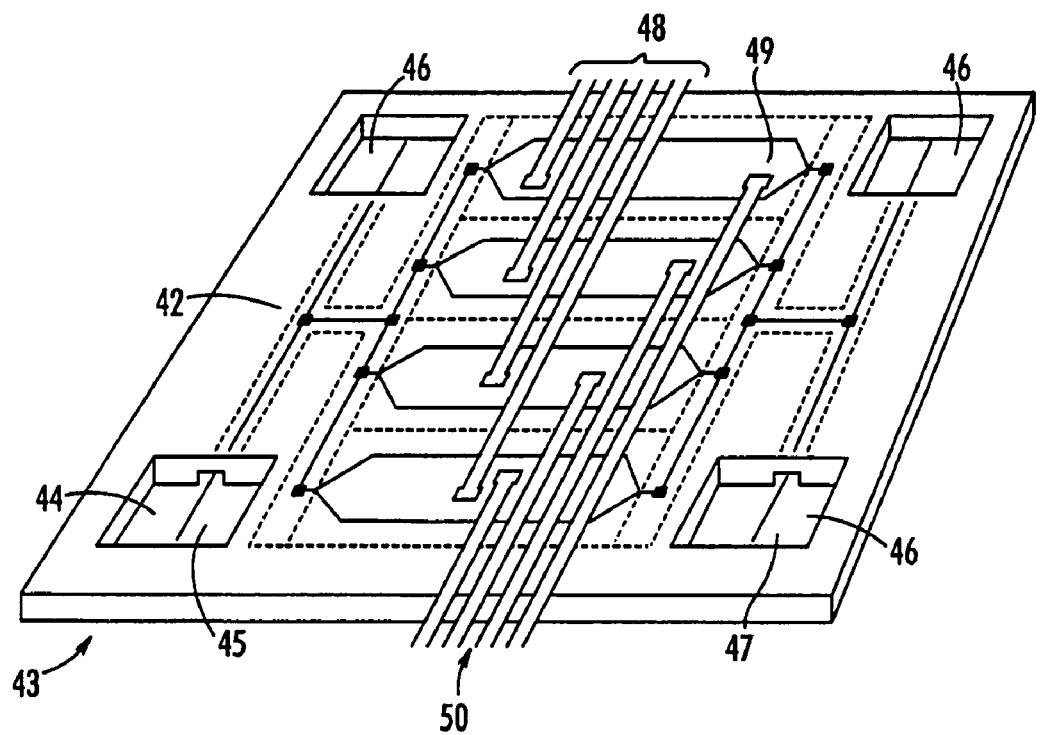
FIG. 6A is a top view of a single layer culture MEMS array.
Figure 6B:
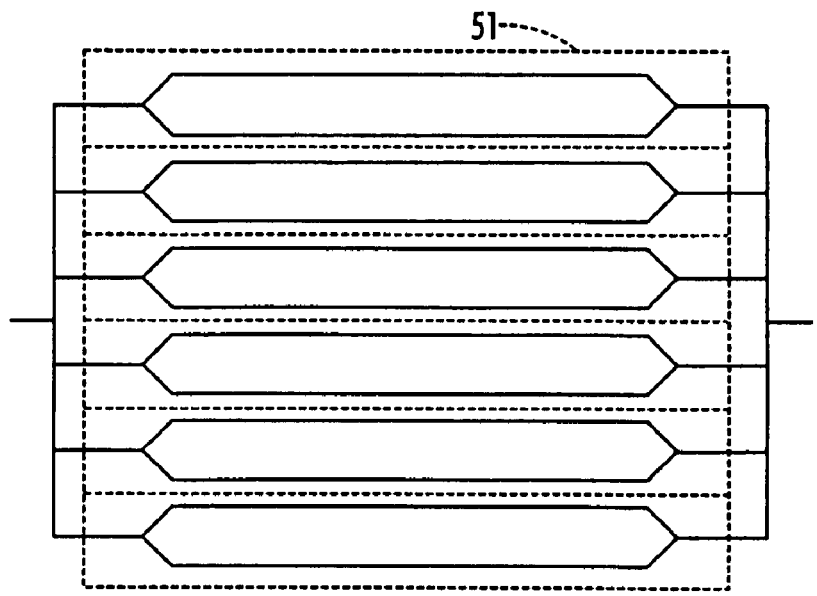
FIG. 6B is a close-up top view of main culture manifold units of a multi-layer culture MEMS array useful for in vitro maturation (IVM), in vitro fertilization (IVF) and in vitro culture (IVC).

FIGS. 6A and B show a single layer culture array and a close-up cross-sectional view of the main culture manifold. The drawing of the single layer culture array 43 shows a loading compartment 44 for receiving oocytes or embryos with embedded labelable zona anchor MEMS that are attracted to the movement tracks 45 of the single layer culture array. Enclosed channels 42 with movement tracks 45 are in communication with the loading compartment 44 as well as removal compartment 46 and a main culture collecting manifold 47 wherein enclosed input 48 and export channels 49 provide for the introduction and removal of fluids. On the movement tracks 45 can be found router elements 50. Enclosed channels 42 are in communication with the main culture manifold 47 and removal compartments 46. FIG. 6B shows the main culture manifold being made up of a plurality of enclosed channels 42 each having its own input 48 and export 49 channels.

1. In one embodiment, a single layer culture array comprises: a multi-laminate planar layer comprising;
   b) at least one loading compartment; c) at least one enclosed channel; d)
   a movement track attractive to a labelable zona anchor MEMS on the floor of enclosed channel; at least one removal compartment; and e) at least one circuit lead communicating between the movement track and the controller unit In a preferred embodiment, a single-layer MEMS culture array for culturing cells or a group of cells comprises:
   (a) at least one loading compartment for loading cells or groups of cells or fluids into the device;
   (b) at least one enclosed channel in fluid communication with the loading compartment and wherein the enclosed channel allows for the passage of cells;
   (c) at least one movement track attractive to labelable zona anchor MEMS attached to the enclosed channel;
   (d) at least one removal compartment for the removal of cells or groups of cells; and
   (e) at least one circuit lead providing communication between at least one movement track and a controller unit.

In a specific embodiment, a single layer cell culture MEMS array further comprises at least one router element which resides on a movement track In yet another specific embodiment, the single layer cell culture MEMS array has at least one enclosed channel with movement track is in fluid communication with a culture manifold for the transport a cell or group of cells and fluid through the cell culture device.

In a specific embodiment, the single layer array has at least one router element resident on a movement track.

In another specific embodiment, the single layer array has at least one enclosed channel with movement track is in communication with a main culture compartment.

For example, the single layer array is used for the culture of oocytes and/or embryos. Further, the single layer culture array is used such that the enclosed channels and other interior cavities are filled with an appropriate culture medium (i.e. Hams-F10, Dearles, M199, DMEM) with appropriate amendments (i.e., hormones, serum, chemicals, nutrients). The filled array is placed into the controller unit and the controller, having been stocked with desired reagents and other fluids in its holding tanks, is provided desired culture and environmental conditions as well as any active process needed over time (i.e., addition and removal of fluids from the array, introduction of sperm, determination of conditions in the interior of the array, i.e. pH, temperature). Oocytes and/or embryos, with labelable zona anchor MEMS devices that are attractive to magnetic media embedded in their zonas, are placed into a loading compartment either by mouth pipette, by a robotic means or other automated manner. The labelable zona anchor MEMS device, being a large object in relation to the oocyte or embryo will orient itself to the bottom of the compartment and, in doing so, come in contact with and attach to the movement track resident in the loading compartment. The movement track provides a forward heading for an attached cell, moving it into the enclosed channel. When the cell reaches a router sitting at the union between two differently oriented movement tracks, the cell is switched (shunted) to the desired track (that switch being mediated by the controller CPU). Upon reaching the main culture collecting compartment the movement tracks cease providing a forward movement and cells are retained in the main culture compartment for a period consistent with the culture needs (i.e. minutes, hours, days) desired as provided by the controller CPU. Upon instruction from the controller CPU (mediated by circuit leads communicating between the movement tracks and the controller CPU) the movement tracks provide forward movement to move the cells out of the main culture compartment to another main culture compartment or to a removal compartment by way of the enclosed channels.

The present invention also provides for a single layer culture array with a plurality of main culture compartments. For example, a single layer culture array of the present invention may have two or more main culture compartments laying in tandem such that cells will move sequentially from a first main culture compartment to a subsequent main culture compartment.

In another embodiment, the present invention provides for a visual image capture device to be resident on the single layer culture array. This a visual image capture device captures an image of cells within the single layer culture array and communicates it (e.g., fiber optic transmission) to an image collection and modification device that is not resident on the single layer culture array. The capture of images in this situation is important for the real-time assessment of the quality of oocytes and embryos over time. This assessment provides the ability to cull out non-viable oocytes or embryos from the array so that resources may be focused only on the highest quality oocytes or embryos as wells as conferring the ability to detect problems that may cause a loss of all ooctes or embryos during culture (e.g., contamination, pH instability).

As used herein, the term "visual image capture devices" refers to a means by which an image may be collected of material within an enclosed channel, collecting manifold, or any other portion of the single layer culture array, e.g., fiber optic video camera leads.

In a specific embodiment, the single layer culture arrays described above further comprises a visual image capture device for visualizing the cells within the array.

The present invention provides for methods of making single layer culture arrays. In one embodiment, the method of making a single layer culture array comprises the modification of a substrate material (i.e. silicon wafer, plastic, metallic oxide, other etchable and depositable material) using etching and depositing modifications (i.e. LIGA, DRIE, silicon fusion bonding, laser etching, laser-mediated and directed substrate polymerization) such that channels and collection compartments are made in the substrate. The movement tracks, circuit leads in communication with the movement tracks, the router elements, and circuit leads in communication with the router elements are deposited onto the previously modified substrate. A second substrate with channels similarly created is bonded on top of the first substrate such that the channels of the second substrate are in communication with the main culture compartment of the first substrate, forming the input and output channels as well as enclosing the open domain or compartment of the first substrate.

H. Multi-Layer Culture Array

Further, the present invention provides for a multi-layer culture MEMS arrays into which said labelable zona anchor MEMS device is attracted and controllably actuated. The multi-layer culture MEMS arrays serve to facilitate the wholesale movement of a plurality of labeled oocytes and/or embryos throughout a variably determinable array of precisely regulated variable culture and treatment environments.

As used herein, the term "multi-layer culture MEMS array" (herein also referred to as a "multi-layer array") refers to a collection of two or more single layer culture arrays in fluid communication by way of one or more enclosed channel bridging elements and provide variably controlled environments for a labelable zona anchor MEMS device. A multi-layer culture array provide different single layer arrays for performing different purposes and activities in each single layer array. For example, a multi-layer array can be made comprising an in vitro maturation array, an in vitro fertilization array and an in vitro culture array.

As used herein, the term "enclosed channel bridging element" refers to a portion of an enclosed channel in one single layer array which is continuous with another section of another single layer array (e.g., two or more single layer culture arrays in a multi-layer culture array). The enclosed channel bridging element "bridges" or connects between separate single layer arrays of a multi-layer array.

In one embodiment, the multi-layer array comprises two or more single layer culture arrays in which the environment (e.g., culture media, pH, temperature, perfusion rates, input ports for non-fluidic culture components, such as, but not limited to, sperm) are precisely and individually controlled.

Figure 7A:
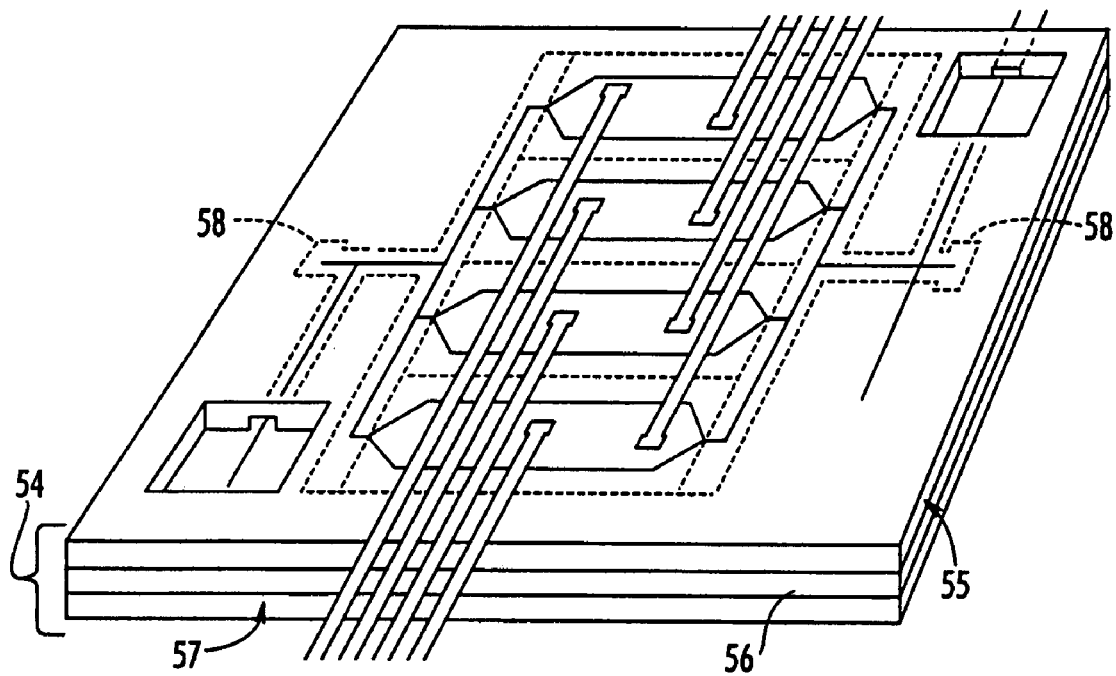
FIGS. 7A-B are a cut-away view of a multi-layer culture array environmental controller and a detailed side cross-sectional view.
Figure 7B:
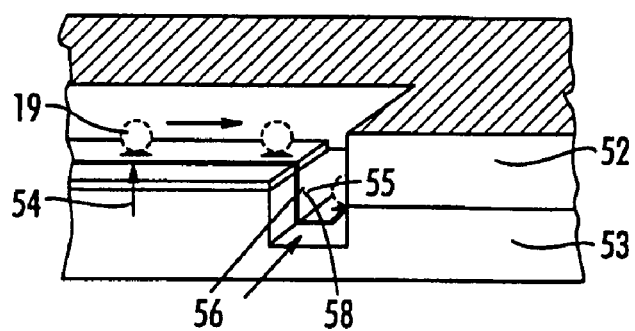

FIGS. 7A-B show a multi-layer culture MEMS array and a detailed side cross-sectional view. FIG. 7A shows three different layers manufactured in a single unit 54 for providing differing functions (i.e., in vitro maturation 55, in vitro fertilization 56, and is in vitro culture 57) and enclosed channel bridging element 58. FIG. 7B shows an enclosed channel bridging element 58. The channel bridging element is the portion of the channel between two layers of a multi-layer culture array that permits fluid communication and cell movement between the layers. The channel bridging element further comprises one or more movement tracks permitting cells to be transported between the layers of the array.

There is shown a first level 6 and a second level 7, the second level 7 being open 11 to the first level. A movement track 8 on the first level 6 with a cell 12 is continuous with a movement track on the side wall of the first layer 9 and a side wall of the second layer 10 that is then continuous with a movement track in the second level 7. In another embodiment, the present invention provides for a visual image capture device to be resident on the multi-layer culture array. This a visual image capture device captures an image of cells within the multi-layer culture array and communicates it (e.g., fiber optic transmission) to an image collection and modification device that is not resident on the single layer culture array. The capture of images in this situation is important for the real-time assessment of the quality of oocytes and embryos over time. This assessment provides the ability to cull out non-viable oocytes or embryos from the array so that resources may be focused only on the highest quality oocytes or embryos as wells as conferring the ability to detect problems that may cause a loss of all ooctes or embryos during culture (e.g., contamination, pH instability).

As used herein, the term "visual image capture devices" refers to a means by which an image may be collected of material within an enclosed channel, collecting manifold, or any other portion of the multi-layer array, e.g., fiber optic video camera leads. In another specific embodiment, the multi-layer array further comprises a visual image capture device for visualizing the cells within the array.

In another embodiment, the multi-layer culture MEMS array comprises a plurality of single layer MEMS arrays wherein the single layer arrays comprise a plurality of enclosed channels reside wherein the channels comprise movement track which are selectively attractive to labelable zona anchor MEMS devices on labeled cells or groups of cells and which provide forward movement to the cells. The enclosed channels of the multi-layer culture MEMS array are capable of containing fluids (i.e., culture media).

In another embodiment, the movement tracks of the single layer MEMS arrays contain routing elements that provide for a change in movement direction (i.e., on to another movement track) of a particular cell or group of cells at a particular portion of the single layer MEMS array.

In another embodiment, circuit elements provide signal transmission from the culture array environmental controller CPU to the routing elements.

In a yet another embodiment, the multi-layer culture array further comprises collecting compartments, communicating with said enclosed channels, into which oocytes and/or embryos may be tracked and held at specified physical parameters for a specified time period, (i.e., in vitro culture).

In yet another embodiment, the multi-layer culture array comprises removal compartments, communicating with said enclosed channels, into which oocytes and/or embryos may be tracked and then become available for removal from the multi-layer culture array.

In one embodiment, one or more single layer culture arrays of a multi-layer culture array comprise at least one enclosed channel bridging element. In another embodiment, the enclosed channel bridging element of the multi-layer culture array forms a continuity between the enclosed channels of one single layer culture array and the enclosed channels of another single layer culture array.

In one embodiment, the multi-layer culture array comprises a plurality of externally communicating input and export channels that lead into said main culture compartments. In another embodiment, the multi-layer culture array comprises a plurality of single layer culture arrays which contain enclosed channels that are continuous and that facilitate the movement of oocytes and/or embryos from one single layer culture array to another. In yet another embodiment, the multi-layer culture array has attached to it, at specific enclosed channels, visual image collection devices, (i.e., fiber optic video camera leads). In another embodiment, the multi-layer culture array is composed of clear plastic. In yet another embodiment, the multi-layer culture array is composed of a microelectromechanical device. In another embodiment, the multi-layer culture array is composed of silicon. In another embodiment, the multi-layer culture array is composed of sapphire. In another embodiment, the multi-layer culture array is composed of metalize oxide. In yet another embodiment, the multi-layer culture array is composed of plastic.

For example, the multi-layer culture array of the present invention is used in a substantially similar manner as that described for the single layer culture array. Further, the enclosed channel bridging elements are actuated by the controller CPU, providing the movement of oocytes and/or embryos from are layer to another layer.

In particular, the multi-layer culture array is placed into an environmental controller, the environmental controller is provided with the desired culture parameters (e.g., length of culture time, temperature), culture fluids are loaded into the multi-layer culture array and any bubbles are purged by way of pressure exerted at any opening to the culture array (e.g., input and output channels). The labeled oocyte or embryos are placed into the loading compartment by mouth pipette, robotic pipette or other automated fluid handling means. Upon the attachment of the label to the movement track in the loading compartment, the cells are moved into the culture compartment and provided with the desired culture conditions (e.g., input and output fluids, temperature) as provided by the environmental controller.

In a preferred embodiment, a multi-layer cell culture MEMS array for culturing a cell or groups of cells, comprising a multi-laminate planar layer comprises:
 (a) at least one loading compartment for loading cells or groups of cells or fluids into the device;
 (b) at least one enclosed channel in fluid communication with the loading compartment and wherein the enclosed channel allows for the passage of cells;
 (c) at least one movement track attractive to labelable zona anchor MEMS attached to the enclosed channel;
 (d) at least one removal compartment for the removal of cells or groups of cells; and
 (e) at least one circuit lead providing communication between at least one movement track and a controller unit.

In a specific embodiment, a multi-layer cell culture MEMS array further comprises at least one router element which resides on a movement track In another specific embodiment, the multi-layer cell culture MEMS array has at least one enclosed channel with movement track is in fluid communication with a culture manifold for the transport a cell or group of cells and fluid through the cell culture device.

Multi-Layer Culture Array Environmental Controllers and Instruments

The present invention provides for multi-layer culture array environmental controllers into which a multi-layer culture array is contained wherein the culture array environmental controller communicates with said single layer or multi-layer culture array by way of the input and export enclosed channels and wherein said culture array environmental controller regulates physical parameters within said multi-layer culture array, e.g., temperature.

As used herein, the term "multi-layer culture array environmental controller" refers to a mechanism whereby a multi-layer culture array may be selectively subjective to specific environmental conditions and whereby selective materials may be introduced into and removed from the multi-layer culture array.

Figure 8:
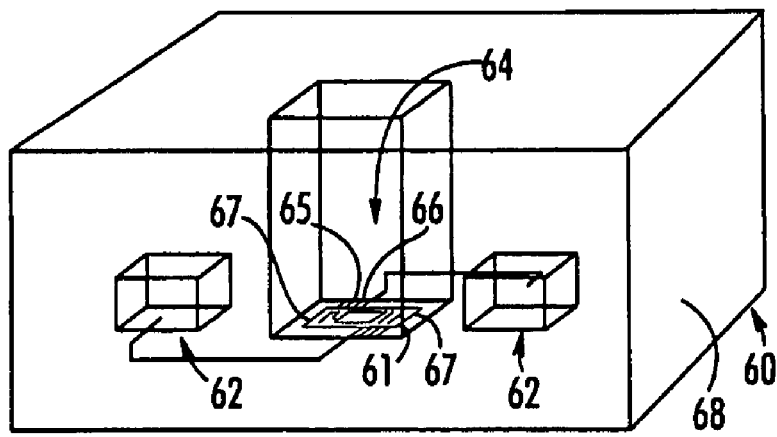
FIG. 8 is a perspective see-through view of an automated environmental instrument.

FIG. 8, shows a culture array environmental controller or instrument 60 for receiving one or more multi-layer culture MEMS arrays 64. The drawing shows a first holding reservoir 62, a second holding reservoir 63, an environmentally controlled docking domain 64 for receiving single layer or multi-layer arrays 64, input and output 65 leads 66 capable of communicating with single layer or multi-layer culture MEMS arrays, input and output port fluid handling means in communication with each reservoir 62,63 and the input and output leads 65, 66, circuit leads in communication between a controller CPU 68 and a culture MEMS devices or arrays 61.

As used herein, the term "fluid-handling means" refers to a series of fluid containing elements, e.g., tubing, which communicates between the environmentally controlled docking domain and another compartment within the multi-layer culture array environmental controller, e.g., a holding tank or reservoir.

As used herein, the term "holding reservoir" refers to a compartment within a multi-layer culture array environmental controller which is constructed so as to hold fluids and maintain them at desired physical parameters, e.g., temperature, pH. Further, the holding tank may be connected to the fluid-handing means such that a selectively permeable barrier lies between the holding tank and the single layer or multi-layer culture array. Yet further, the holding tank may be so constructed as to allow the input of materials separate from the opening for the connection to the fluid-handling means.

As used herein, the term "visual image detection device" refers to a means to collect image data from the visual image collection devices at the single layer or multi-layer culture array and either interpret it or output to an interpreting device.

As used herein, the term "multi-layer culture array environmental controller CPU" refers to a programmable data processor that is operable linked to integrated circuit elements on the single layer or multi-layer culture array. Further, said multi-layer culture array environmental controller CPU determines the temporal and spatial positioning of labelable zona anchor MEMS devices on said single layer or multi-layer culture array.

As used herein, the term "integrated circuit elements" refers to a circuit which provides signal transmission to the routing elements on a planar array of a single layer or multi-layer culture array.

As used herein, the term "environmentally controlled docking domain" may include a compartment within a multi-layer culture array environmental controller which accepts and secures a single layer or multi-layer culture array. Further, the environmentally controlled docking domain has a means by which it regulates the physical parameters within the single layer or multi-layer culture array such as temperature. Yet further, the environmentally controlled docking domain has a means for connecting the externally communicating input and export channels of a single layer or multi-layer culture array to a fluid-handling means within the multi-layer culture array environmental controller.

The present invention provides for a method of using said labelable zona anchoring MEMS device in conjunction with said single layer or multi-layer culture array and multi-layer culture array environmental controller wherein the labeled cells or group of cells, such as oocytes and/or embryos are attached to the are placed into a loading compartment of said single layer or multi-layer culture array which is in turn placed into a multi-layer culture array environmental controller which mediates the introduction, maintenance, and modulation of environmental conditions over time.

In another embodiment, the culture array environmental controller further comprises a fluid-handling means for communicating with single layer or multi-layer culture array input and export enclosed channels. In another embodiment, the fluid-handling means of the environmental controller connects a holding tank contained within the multi-layer culture array environmental controller to the input and export enclosed channels of the culture array. In another embodiment, the physical environment of the holding tank contained within the multi-layer culture array environmental controller can be variably maintained. In another embodiment, the holding tank contained within the multi-layer culture array environmental controller holds a fluid, (i.e., culture media) or a cell suspension, (i.e., capacitated sperm, cumulus cell suspension).

In another embodiment, the holding tank further comprises a selective barrier, (i.e., a filter), between the tank contents and the fluid handling means so as to prevent particulate materials from being passed into said fluid-handling means. In another embodiment, the holding tank with the selective barrier contains a cell culture thus providing to the single layer or multi-layer culture array a conditioned culture media without a cellular component.

In one embodiment, the culture array environmental controller further comprises a visual image detection device that communicates with the visual image collection devices, (i.e., fiber optic video camera leads) contained within the single layer or multi-layer culture array. In one embodiment, the culture array environmental controller further comprises a culture array environmental controller CPU whereby said multi-layer culture array environmental controller CPU programmably signals, by way of circuit elements, to the router elements on movement tracks of a single layer array or a multi-layer culture array such that the heading of labelable zona anchor MEMS devices or labeled cells moving on the movement tracks is changeable.

J. Microinjection MEMS Array

The introduction of small volumes of fluids, suspensions or materials containing dyes, proteins, DNA molecules, RNA molecules, viruses, as well as other compounds is important to a wide range of developing technologies. The introduction of DNAs and RNAs that modify and even become integrated into the genome of a target cell is important to biological studies, gene therapy, as well as the generation of transgenic cells and, in the case of the introduction of heritable genetic changes in the genome of an oocyte or embryo, trangenic animals.

While there are a great many methods for the introduction of small volumes of fluid into the cytoplasm of culture cells as well as cells in situ, there are a limited number of ways that the introduction of small volumes of fluid into oocytes or embryos can be effected. Currently, these reagents are introduced into oocytes and embryos by micromanipulation wherein miniature glass needles are usually manually forced into the cell and pressure is applied to push the injection fluid or suspension into the cell. A device that would facilitate the automation and standardization of this technique would offer significant advantages over the present state of the art.

Accordingly, the present invention provides for the introduction of fluids or suspensions into the cytoplasm or nucleus of a cell or group of cells such as but not limited to an oocyte or embryo, using a microinjection MEMS device array, that facilitates the injection of a small volume of fluid into the cytoplasm or nucleus of a cell or group of cells such as an oocyte or embryo. The present invention also provides for microinjection MEMS Device kits, methods of using the devices and kits and methods of making the devices.

The term "microinjection" refers to the process by which fluids, such as solutions (i.e., DNA, RNA, proteins, organic compounds), are injected into the interior (i.e., the cytoplasm, the nucleus) of cells (i.e., cells, oocytes, embryos) using needles manufactured from glass (i.e., borosilicate). These needles are actuated by way of micromanipulators that provide controllable (i.e., by hand, joystick/servo machinery) movement in all three planes (i.e., x, y, z). Additionally, fluids contained within the needle can be expelled by way of a pressure system (i.e., hydro, pneumatic) in communication with the needle.

In one embodiment, a microinjection MEMS device comprises:

(a) a silicon wafer comprising at least one well in fluid communication with a fluid transfer channel and wherein the well comprises at least one hollow protuberance; and (b) an input manifold in fluid communication with the fluid transfer channel.

In another embodiment, the microinjection MEMS device further comprises a pumping means.

In a preferred embodiment, a microinjection MEMS device for injecting a fluid, a suspension or a material into a cell or group of cells comprises:

(a) a first substrate comprising at least one well for holding the cell or group of cells and wherein the well comprises at least one hollow protuberance for penetrating the cell or group of cells and wherein the well is in fluid communication with a fluid transfer channel wherein the fluid transfer channels permits the fluid to enter the hollow protuberance and to then enter the cell; and (b) a second substrate comprising an input manifold in fluid communication with the fluid transfer channel wherein the input manifold allows for the input of the fluid, suspension or material into the hollow protuberances.

In a more specific embodiment, the invention provides a microinjection MEMS device wherein the well is cube-shaped.

In yet another embodiment, the microinjection MEMS device wherein the cube-shaped well is from about 50 µm to about 200 µm in length per side. In another specific embodiment, of the microinjection MEMS device, the well is conical-shaped.

In another specific embodiment, the microinjection MEMS device, the hollow protuberance is a needle, more specifically a microneedle. In yet another specific embodiment, the hollow protuberance is from about 0.01 µm to about 10 µm in diameter.

In one embodiment, the hollow protuberance may be so constructed as to act as an emittor. In particular, the hollow protuberance may act as a wave guide to conduct electromagnetic signals (e.g., pulses of light of any frequency). Additionally, the hollow protuberance can provide vibrational energy (e.g., sound waves, e.g., ultrasonic waves). The hollow protuberance acting as an emittor facilitates the piercing of the protuberance or microneedle into the cell with a minimal amount of damage to the cell.

In a particular embodiment, the microinjection MEMS device further comprises a coating. In more specific embodiments, the coating is a polypeptide, peptide or protein. In another specific embodiment polypeptide is polylysine.

The present invention also provides for a method of making a microinjection MEMS device comprising the steps of:

(a) etching a plurality of parallel channels on a first side of a plurality of silicon wafers in which the wafers each have a second unetched side;

(b) silicon fusion bonding the unetched side of a plurality of silicon wafers of step (a) to the etched side of a plurality of silicon wafers of step (a) such that the etched channels are in parallel to form a mega-laminate wherein the mega-laminate has a plurality of holes formed by the channels;

(c) cutting the mega-laminate at an angle perpendicular to the long axis of the etched channels thereby forming a slice of the mega-laminate having a top surface and a bottom surface wherein each surface exposes an end of the channel;

(d) silicon fusion bonding the bottom surface of the slice of the mega-laminate to the etched side of a channel-etched base-plate wafer;

(e) depositing a first mask on the top surface of the slice of the mega-laminate such that a region surrounding each channel end is free of mask;

(f) etching the mask to form a plurality of wells;

(g) depositing a second mask on the mega-laminate top surface such that a border forms around each channel end such that material around the channel is not etched;

(h) etching the second mask thereby forming a plurality of hollow protuberances within the wells.

In a specific embodiment, the method of making a microinjection MEMS device further comprises applying a coating to the mega-laminate top surface after step (h).

In yet another specific embodiment, the method of making a microinjection MEMS device, wherein the coating is a polypeptide, peptide or protein.

In a more specific embodiment, the polypeptide is polylysine.

The present invention also provides a method of making a channel-etched base-plate silicon wafer with a pump/valve comprising the steps of:

(a) etching a silicon wafer with a plurality of channels which are in fluid communication within input manifold reservoir;

(b) etching the silicon wafer of step (a) whereby a pump/valve is constructed in each channel; and (c) a circuit lead between the pump/valve and a controller is deposited.

In a specific embodiment, the method of making a channel-etched base-plate silicon wafer with a pump/valve comprises a piezoelectric pump/valve in step (b).

The present invention also provides for, a microinjection MEMS device kit comprising:

(a) at least one microinjection MEMS device; and (b) a centrifugal platter for applying a centripetal force to a cell or group of cells contained within a MEMS device comprises a circular disk having a plurality of ports for holding the MEMS device.

In a preferred embodiment, a microinjection MEMS device kit for injecting a fluid, a suspension or a material into a cell or group of cells comprising:

(a) a centrifugal platter for applying a centripetal force to a cell or group of cells contained within a MEMS device wherein the centrifugal platter comprises a circular disk, a plurality of ports for holding the MEMS devices and a securing means to secure the platter to a spinner or driving means; and at least one microinjection MEMS device.

In a specific embodiment, the microinjection MEMS device kit comprises the microinjection MEMS device permanently affixed to the centrifugal platter.

In another embodiment, the present invention provides the microinjection MEMS device kit wherein (a) the centrifugal platter comprises a plurality of grooves arranged in a concentric pattern and wherein each groove has an inner and outer edge;

(b) at least one microinjection MEMS device is bonded to the outer edge of a groove in an orientation such that the axis of each well of the microinjection MEMS device is horizontal to the plane of the centrifugal platter; and (c) the inner edge of the grooves forming divided compartments comprising a single well that restrict the movement of materials from one compartment containing a single well to another compartment.

The present invention also provides a method of using a microinjection MEMS device kit of comprising the steps of:

(a) filling the input manifold of at least one microinjection MEMS device resident on a centrifugal platter with a fluid;

(b) loading the fluid-filled wells of step (b) with at least one oocyte or embryo;

(c) placing the microinjection MEMS/centrifugal platter into a centrifuge;

(d) rotate said centrifugal platter thus applying a centripetal force on the microinjection MEMS/centrifugal platter.

In another embodiment, a method of using a microinjection MEMS device kit comprises the steps of:

(a) filling the grooves of the centrifugal platter with a fluid;

(b) loading the grooves of the centrifugal platter with at least one oocyte or embryo; and (c) applying a centripetal force to the kit whereby the oocyte or embryo makes contact with the hollow protuberance of the microinjection MEMS device and the hollow protuberance penetrates the surface of the oocyte or embryo.

In a more specific embodiment, a centripetal force on the microinjection MEMS device kit by rotating the kit using a spinner or driving means.

Another specific embodiment describes a method of using a microinjection MEMS device kit wherein, upon rotation of centrifugal platter, a volume of fluid is caused to enter the oocyte or embryo in the cell well through the hollow protuberance.

The present invention also provides a microinjection MEMS device comprising:

(a) a well for accepting one or more cells comprising a hollow protuberance;

(b) a fluid handling means in fluid communication with said hollow protuberance; and (c) a central fluid loading manifold.

In a specific embodiment, fluid handling means is a dynamic hydropressure column.

The present invention also provides for a microinjection MEMS array for injection of a fluid, a suspension or a material into a cell or group of cells comprising:

(a) a first substrate comprising at least one well for accepting a cell or group of cells and wherein the well comprises a hollow protuberance for penetrating the cell or group of cells;

(b) a second substrate comprising a fluid handling means in fluid communication with said hollow protuberance; and (c) a central loading manifold for loading a fluid into the array.

In a specific embodiment, in a microinjection MEMS array of claim the fluid handling means is a dynamic hydropressure column.

In another specific embodiment the device is embedded in a centrifugal platter.

The invention also provides for a method of using the microinjection MEMS array comprising:

(a) applying an inertial force to the device using a centripetal (angular) acceleration means brought about by rotation of centrifugal platter In yet another embodiment, a microinjection MEMS array for injecting a fluid, a suspension or a material into a cell or group of cells comprises:

(a) a central loading manifold for loading the fluid, suspension or material into the array;

(b) a plurality of wells for receiving cells;
(c) a hollow protuberance within each well for penetrating the cell and injecting the fluid, suspension or material; and
(d) a plurality of dynamic hydropressure columns in fluid communication with the central loading manifold and with the hollow protuberances wherein the dynamic hydropressure columns provide pressure for forcing the fluid, suspension or material through the hollow protuberance and into the cell.

In a more specific embodiment, the microinjection MEMS array further comprises at least one valve in the dynamic hydropressure column for modulating fluid flow.

In yet another specific embodiment, in a microinjection MEMS array, wherein each valve is in operable communication with a controller to control the fluid, suspension or material flowing into the cell.

The microinjection MEMS device further comprises at least one valve in the dynamic hydropressure column for modulating fluid flow.

Further, a microinjection MEMS device is provided wherein each valve is in operable communication with a controller to control the fluid, suspension or material flowing into the cell.

Additionally, a microinjection MEMS device is provided wherein the operable communication is mediated by circuits.

In another embodiment, a microinjection MEMS device wherein the hollow protuberance acts as an emittor More specifically, a microinjection MEMS device is provided wherein the hollow protuberance, acting as an emittor, emits pulses of light (e.g., any frequency). In yet another specific embodiment, a microinjection MEMS device is provided wherein the hollow protuberance, acting as an emittor, emits pulses of sound (e.g., ultrasonic waves).

Further, in other embodiments, a microinjection MEMS device is provided wherein the operable communication is mediated by electrical or optical circuits.

A method of using a microinjection MEMS device of comprising:
1. loading at least one cell or group of cells into an injection domain of the microinjection MEMS device;
2. applying a centripetal force to the microinjection MEMS device thereby causing penetration of the cell or group of cells by the hollow protuberance of the microinjection MEMS device; and deposition of a substance in the cell or group of cells from the hollow protuberance.

A method of using a microinjection MEMS device comprising
(a) loading at least one cell or group of cells into the injection domain of the microinjection MEMS device;
1. rotation of microinjection MEMS device whereby the cell is thrust upon hollow protuberance resident within injection domain;
2. simultaneous passive movement of fluid through dynamic hydropressure columns provides pressure to push fluid into cell; and
3. removal of cell from microinjection MEMS device.

In another embodiment, the method of using the microinjection MEMS further comprises a gating valve that, being activated by a controller by way of a circuit, provides for variable fluid flow from the dynamic hydropressure column into the cell.

In another embodiment, the hollow protuberance emits a pulse of energy (e.g., lights, sound) that provides a means for a focused disruption of the lipid bi-layer of the cell membrane of the oocyte or embryo.

A variety of methods of using the present invention of microinjection MEMS devices will be apparent to those skilled in the art.

In a preferred embodiment, a method of using a microinjection MEMS device involves the microinjection MEMS device being affixed to a means for applying centripetal forces to said microinjection MEMS. The invention further provides for a method of using a microinjection MEMS device comprising the microinjection MEMS device being affixed to a means for applying centripetal forces to said microinjection MEMS further comprising a well for receiving an oocyte or embryo communicating directly with a microinjection MEMS such that when a centripetal force is applied the oocyte or embryo contained within the well communicating with the microinjection MEMS, the oocyte or embryo is forced against the microinjection MEMS such that the hollow protuberance of the microinjection MEMS penetrates through the zona pellucida, through the oollema, and into the cytosolic or nucleoplasmic compartment of the oocyte or embryo.

Alternatively, as the oocyte or embryo is thrust upon the hollow protuberance, the hollow protuberance emits a pulse of energy (e.g., lights, sound), introducing a focused opening in the lipid bi-layer of the plasma membrane of the oocyte or embryo thus facilitating a tightly focused puncture of the membrane. This is important for cell viability.

In another preferred embodiment, the microinjection MEMS device of the present invention is permanently embedded in a substrate base. A substrate base (i.e., silicon wafer, plastic cartridge) includes, but is not limited to, a silicon wafer or plastic cartridge that comprises a well for receiving a microinjection MEMS device, upon fixation of which, a depression remains adjacent to the microinjection MEMS device. This remaining depression that is adjacent to the affixed microinjection MEMS device is for receiving an oocyte or embryo. The substrate base also comprises a lever adjacent to the remaining depression for thrusting the oocyte or embryo, being placed in the remaining depression, against the microinjection MEMS device. The substrate base also comprises a fluid handling and pumping means in fluid communication with the hollow protuberance of the microinjection MEMS device.

In a more specific embodiment, a microinjection MEMS device kit comprises (a) a microinjection MEMS device; and a base pumping substrate. The term "base pumping substrate" includes a substrate base (i.e., silicon wafer, plastic cartridge) that accepts a MEMS device, and comprises a fluid handling means in fluid communication with the hollow protuberance or needle of a microinjection MEMS device, a pumping member on the substrate base, and a lever that selectively pushes a oocyte or embryo against the MEMS device.

Figure 28:
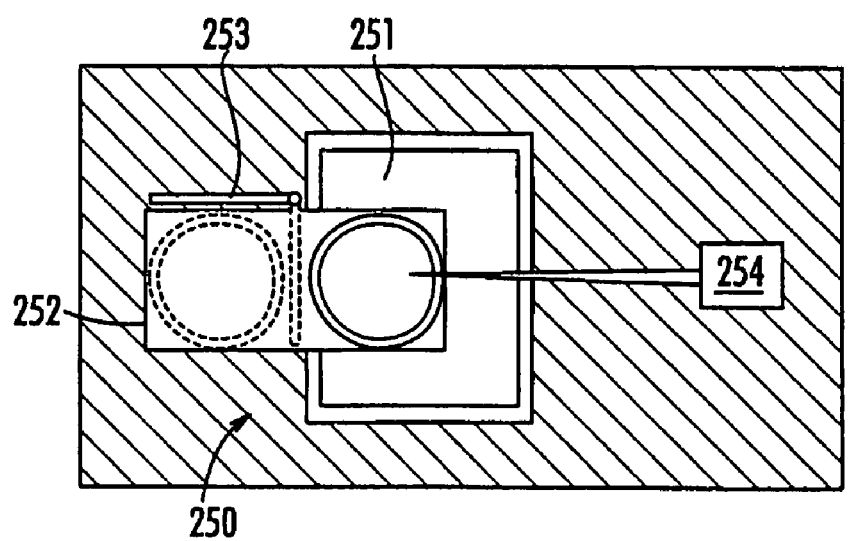
FIG. 28 is a top cross sectional view of a base pumping substrate.

FIG. 28 illustrates a base pumping substrate 250 with a MEMS device attached thereto 251 and the base pumping substrate comprises an input well 252, a lever 253, that swings between the input well 252 and the MEMS device regulating the movement of the cell.

The microinjection MEMS kit operates, for example, as follows: the kit being filled with fluid, the oocyte or embryo being loaded into the kit, the lever thrusting against the oocyte or embryo and thus trusting the oocyte or embryo against the microinjection MEMS hollow protuberance, upon the penetration of the oocyte or embryo by the hollow protuberance of the microinjection MEMS the pump pushes a a small volume of fluid through the fluid handling means and through the microinjection MEMS hollow protuberance and into the cytosol or nucleoplasm of the oocyte or embryo. In another embodiment, as the oocyte or embryo is being thrust against the hollow protuberance of the microinjection MEMS device the hollow protuberance emits a pulse of energy (e.g., light, sound) and provides a focused opening in the membrane lipid bi-layer, facilitating the movement of the hollow protuberance through the membrane.

The present invention further provides for the maintenance of a positive pressure in the microinjection MEMS.

If a centrifugal platter is being used to provide pressure to the fluid handling means then a positive pressure is present upon rotation of the kit. If a substrate base with a fluid pumping means is used to provide for injection then the pump of the substrate base provides the positive pressure. Positive pressure is applied to prevent back flush of oocyte or embryo cytosolic materials into the hollow protuberance. Neutral pressure would serve an analogous purpose.

The present invention also provides for a method of manufacturing a microinjection MEMS device wherein a silicon wafer is etched by silicon etchant/modifying technologies (e.g., deep silicon reactive ion etching, silicon surface micromachining, LIGA). Those of skill in the art of MEMS manufacturing will know of a variety of methods of making the MEMS microinjection devices of the present invention.

A preferred method of making the microinjection MEMS devices of the present invention are set forth in FIGS. 9-15.

Figure 9:
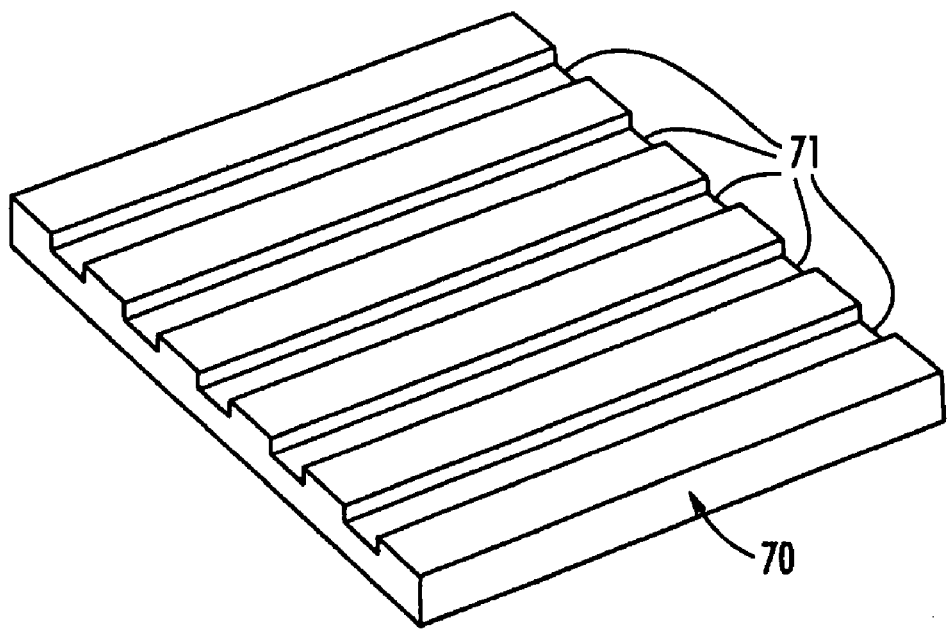
FIG. 9 is a perspective view of a channel etched plate of a microinjection MEMS device.

FIG. 9, shows a silicon wafer etched with channels 71 also called a "pre-hole" wafer.

Figure 10:
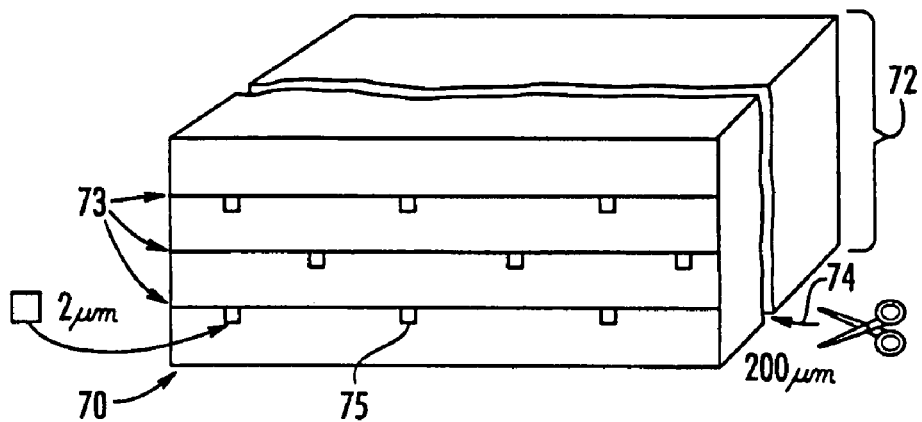
FIG. 10 is a perspective view of a mega-laminate of a microinjection MEMS device where the plane of the slicing action is indicated.

FIG. 10 shows a multi-laminate wafer 72. This structure is composed of more than one "pre-hole" wafer 70 of FIG. 9, bonded, (i.e., silicon fusion bonded forming sfb interfaces 73), such that channels 71 are sealed along the long axis forming holes 75. This figure also illustrates the cutting plane 4 where the multi-laminate wafer is cut forming a pre-needle wafer.

Figure 11:
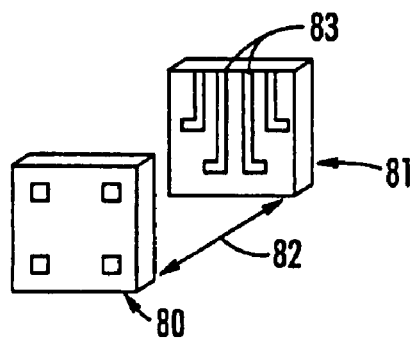
FIG. 11 are side views of a mega-laminate wafer being bonded to a channel etched plate of a microinjection MEMS device.

Referring to FIG. 11, there are shown two wafers, a pre-needle wafer 80, the result of cutting the multi-laminate wafer FIG. 10, and a channel-etched base-plate wafer 81 with fluid channels 83. These two wafers are bonded, (i.e., silicon fusion bonded), and form a sfb interface, (i.e., a silicon fusion) bonding interface (sfb interface) 82.

Figure 12:
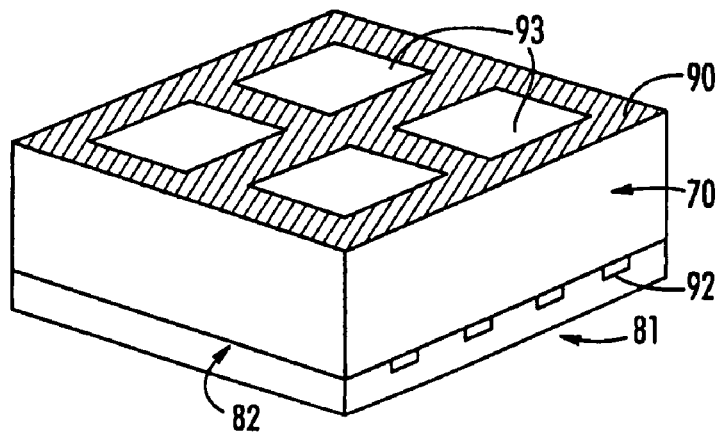
FIG. 12 is perspective view of the first mask (hatched area) of a microinjection MEMS.

FIG. 12, shows a pre-needle wafer fused to the channel-etched base-plate wafer of FIG. 8. A mask 80 is applied to the top surface of the pre-needle wafer 70 such that there are square unmasked regions 93. The input ports 1 formed when the pre-needle wafer 70 and the fluid channel wafer 81 were bonded at the sfb interface 82.

Figure 13:
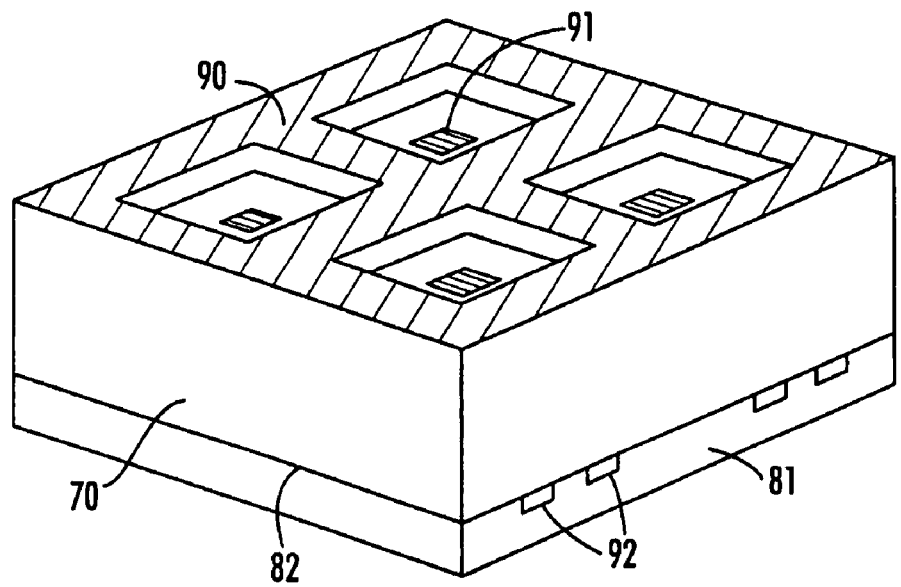
FIG. 13 is a perspective view of the masks for the fabrication (hatched area) of a microinjection MEMS.

FIG. 13, there is shown a pre-needle wafer fused to the channel-etched base-plate wafer of FIGS. 11 and 12. Two more masks 90 and 91 are applied to the surface of the pre-needle wafer 70 as shown. The first mask 90 maintains the initial upper height of the pre-needle wafer. The second mask 91 protects material surrounding the holes resident within the pre-needle wafer 70. the input ports 92 are shown which provide access to the fluid channels 83.

Figure 14:
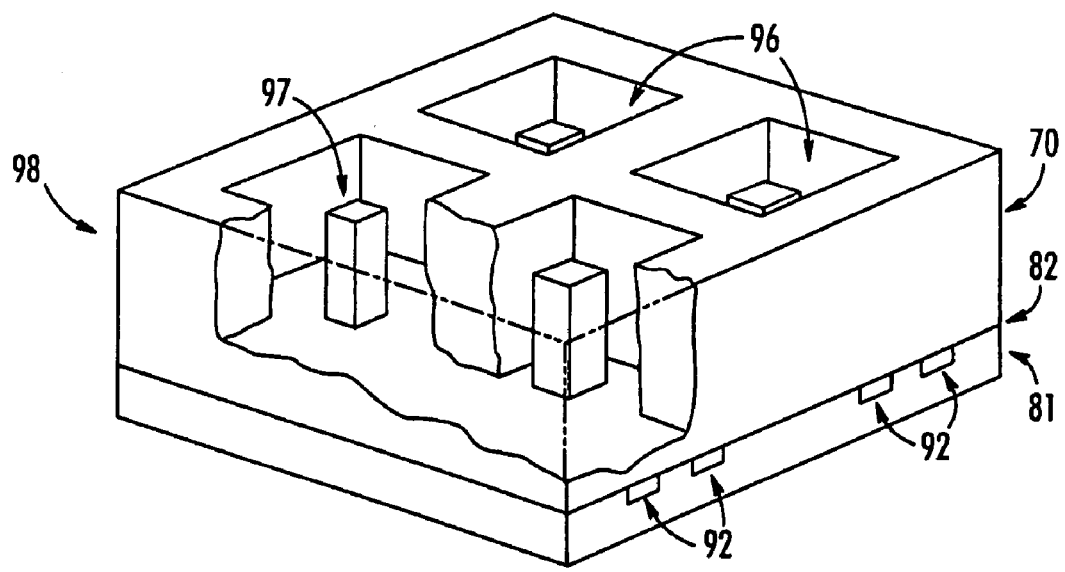
FIG. 14 is a perspective view of microinjection MEMS with a cross-sectional view to show interior detail of the cell wells.

FIG. 14 shows the pre-needle wafer to the channel-etched base-plate wafer of FIGS. 11, 12 and 13 after the final etch. Wells 96 are at their final depth and a hollow protuberance (or a microneedle) 97 is formed within each well 96 in the pre-needle wafer 70 forming a microneedle-wafer 98. Each hollow protuberance 97 is in communication with the fluid channels 83 of the channel wafer 81.

FIG. 15 shows one possible embodiment of a channel etched wafer 81. In this figure the channel etched wafer has a plurality of fluid channels 83 etched into the top surface in communication with an input manifold 100. Between the input manifold 100 and the distal portions of the etched channels 83 there can be a pump 101, (i.e., a piezoelectric pump) in the channel 82. Additionally, the pump may be actuated by circuits, or leads 102 i.e., deposited integrated circuits (not shown), communicate between said pump and a controller.

FIG. 16 shows a portion of microinjection MEMS device 110 and a centrifugal platter 111 with a microinjection MEMS device 110 resident on it thereby forming a kit. The microinjection MEMS device 110 is seen to be composed of a channel wafer 81, a microneedle wafer 98, a silicon fusion bonding interface 82, wells 96, microneedles 97, and input ports to fluid channels 92 in communication with the microneedles 97. Further, this figure illustrates how a microinjection MEMS 110 is placed on a centrifugal platter 111 that has cell loading regions 112 that correspond to each well 96 on the microinjection MEMS devices 110. Upon rotation of the centrifugal platter 111 a centripetal force 113 is generated in a perpendicular direction out from the center of the centrifugal platter 111.

FIG. 17, shows an embodiment of a microinjection MEMS array. There is a central loading manifold 120 wherein injectant material is loaded, cell loading regions 121, dynamic hydropressure columns 122, valves on dynamic hydropressure columns 123, microinjection needles 124. Upon rotation of this array, fluids in the central loading manifold 120 will migrate into and through the dynamic hydropressure columns 122, through the microinjection needles 124 and into the cells 125. The direction of the fluid movement is pointed out by arrows.

FIG. 18 shows a single microinjection MEMS unit of the array shown in FIG. 17. This unit comprises a dynamic hydropressure column 123, a valve 123, a circuit lead 127 that actuates the valve 123, a controller 128 to which the circuit 127 lead communicates, a well 126, a hollow protuberance or microinjection needle 124, and a cell 125 to be injected. Upon rotation of the microinjection MEMS array of which this unit is a part of, a force, the centripetal force 129, is exerted on the fluid in the dynamic hydropressure column 122, forcing fluid into the cell 125.

An alternative method of making the microinjection MEMS devices of the present invention is the modification of a substrate base (i.e., silicon wafer, plastic, metallic oxide or other etchable and depositable material) using etching and deposition modification (i.e., LIGA, DRIE, silicon fusion bonding, laser etching, laser mediated and directed substrate polymeritation) such that desired structures are formed on and in the substrate base. In a preferred embodiment, the method of making the microinjection MEMS devices of the present further comprises the formation of the following structures: a central loading manifold, cell wells with a hollow protuberance, dynamic hydropressure columns in communication between the central loading manifold and the hollow protuberance resident in the cell well and cell loading region. This method further comprises a gate present on the dynamic hydropressure column to provide for variable fluid flow, and a circuit lead in communication with the gate and a controller.

This method further comprises the deposition of circuit leads in communication with the hollow protuberance providing transmission of current and data for the facilitation of hollow protuberance function as an emittor (e.g., light, sound pulses). These circuit leads communicate with a controller.

Another alternate method of making the microinjection MEMS devices of the present invention is substantially similar to the method described immediately above wherein the structures formed are: a cell loading region, an injection fluid loading region, cell well with a hollow protuberance in fluid communication with a fluid handling means that is in fluid communication with the injection fluid loading region and a pump situated on the fluid handling means between the hollow protuberance and the injection fluid loading region.

ICSI MEMS

The introduction of small volumes of fluid containing dyes, proteins, DNA molecules, RNA molecules, viruses, sperm cells, as well as other compounds is important to a wide range of developing technologies.

While there are a great many methods for the introduction of small volumes of fluid into the cytoplasm of culture cells or cells in situ, there are a limited number of effective methods for introducting sperm cells and small volumes of fluid into individual cells or groups of cells such as oocytes or embryos. Devices and methods to facilitate the automation and standardization of ICSI techniques would offer significant advantages over the present state of the art.

Male factor infertility, where sperm are incapable of penetrating the zona pellucida and oollemma of an oocyte in such a way that fertilization occurs, has been ameliorated only recently by the advent of the use of a technique called Intra-Cytoplasmic Sperm Injection (ICSI). ICSI involves the micromanipulation of both the oocyte and sperm such that an oocyte is immobilized, a micropipette is used to sever the tail of a candidate sperm, the micropipette is used to pick up the severed sperm head, and the micropipette is used to inject the sperm head into either the perivitelline space (the space between the zona pellucida and the oollemma) or directly into the cytoplasm of an unfertilized oocyte. By this means, motility-impaired sperm have given rise to successful pregnancies. This technique represents a significant investment in highly specialized equipment, extensive training, and scarce gamete resources. Further, pregnancy outcomes are highly dependent on the skill of each individual performing the ICSI. A device that would facilitate the automation and standardization of this technique would offer significant advantages over the present state of the art.

The term "Intracytoplasmic Sperm Injection" or "ICSI" refers to the process by which a capacitated sperm, usually with the tail removed, is injected, using needles and handling system similar to those described for microinjection, into the interior of an oocyte thereby fertilizing the oocyte and potentially forming an embryo.

The present invention provides for ICSI MEMS devices and kits, that facilitate the injection of a sperm into the cytoplasm of a cell such as an oocyte. The present invention also provides for methods of using ICSI MEMS devices and methods of making the devices.

In one embodiment, a IntraCytoplasmic Sperm Injection (ICSI) MEMS device comprises:
  (a) at least one well for accepting cells wherein the well comprises a hollow protuberance;
  (b) a sperm handling manifold;
  (c) at least one fluid handling means in fluid communication between the hollow protuberance and the sperm loading manifold; and
  (d) a sperm guillotine in communication with the fluid handling means.

In a more particular embodiment of the ICSI MEMS device, the fluid handling means is a dynamic hydropressure column.

In another embodiment, the ICSI MEMS device further comprises at least one gating valve also called a guillotine gate (hereinafter referred to as a "gate"). In a specific embodiment, each gate is in operable communication with a controller. In yet another specific embodiment, the operable communication is mediated by circuits, and more specifically, the operable communication is mediated by Electro-optical circuits.

In another preferred embodiment, a IntraCytoplasmic Sperm Injection (ICSI) MEMS array for injecting a sperm into a cell comprises:
  (a) a substrate comprising at least one well for accepting cells wherein the well comprises a hollow protuberance for penetrating the cell to inject the sperm;
  (b) a sperm handling manifold for loading the sperm into the array;
  (c) at least one fluid handling means in fluid communication between the hollow protuberance and the sperm loading manifold for delivering the sperm to the array; and
  (d) a sperm guillotine in communication with the fluid handling means wherein the sperm guillotine severs the tail from the sperm.

In a specific embodiment, in the ICSI MEMS array of, the fluid handling means is a dynamic hydropressure column.

In yet another specific, an ICSI MEMS array kit comprises at least one ICSI MEMS array affixed to a centrifugal platter for applying a centripetal force to a cell or group of cells contained within a MEMS device wherein the centrifugal platter comprises a circular disk, a plurality of ports for holding the MEMS devices and a securing means to secure the platter to a spinner or driving means.

In another embodiment, the ICSI MEMS array further comprising;
  (a) at least one valve residing in the dynamic hydropressure column for regulating the flow of the fluid, suspension or material; and
  (b) a sperm guillotine for severing the tail from the sperm.

More particularly, each valve of the array is in operable communication with a controller.

More particularly, the sperm guillotine for severing the tail from the head of a sperm comprises:
  (a) an enclosed sperm channel for containing a sperm having a head and a tail; (b) a first guillotine gate capable of sliding through a first end of the enclosed channel and capable of halting the forward movement of the sperm; for
  (c) a second guillotine gate capable of sliding through a second end of the enclosed channel and capable of severing the tail from the sperm
  (d) a controller for controlling the sliding motion of the guillotine gates; and
  (e) a circuit lead communicating between each gate and the controller, wherein the circuit lead enables the controller to direct the movement of each gate.

Figure 20A:
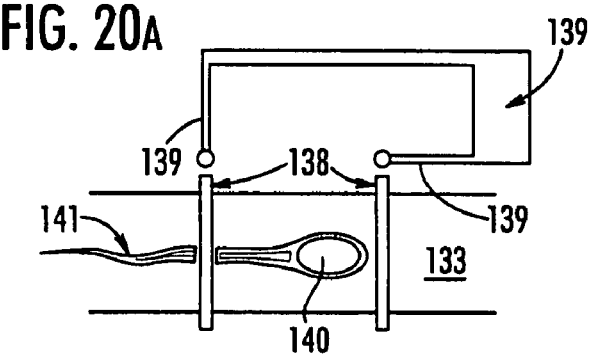
FIG. 20A is a representation of a bimorphic sperm guillotine gating mechanism.
Figure 20B:
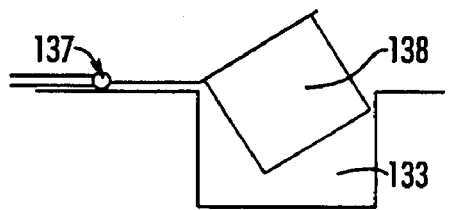
FIG. 20B is a side cross-sectional view of the ISCI MEMS channel and bimorph guillotine/gate.

Further, the present invention provides a method of making a sperm guillotine comprising the steps of: (a) depositing a first mask that inscribes a channel and at least one guillotine gate;
  (a) etching of the first mask to form the channel and the guillotine gates;
  depositing circuit leads between each gate and a controller FIG. 20A shows two views of a sperm guillotine. The top view shows a sperm channel 133, a first and a second guillotine gate 138, circuit lead 139 communicating between guillotine gate 138 and controller 139, illustrating how a sperm head 140 is separated from the sperm tail 141. FIG. 20B shows a side cut-away view illustrating the position of the guillotine gate 138 in the sperm channel 133. The circuit lead 139 is shown in communication with the guillotine gate 138 and the controller.

The operation of the gate is as follows: the first gate opens while the second gate remains closed, a sperm swims into the guillotine (the size of the guillotine, being on the order of approximately 1 micron wide and the gates being approximately 5 microns long, allows for a single sperm to engage the guillotine and the span between the first gate and second gate equals approximately the length of the head, ensuring that the tail will be cut with very little remaining behind the sperm head), the first gate shuts closed, severing the tail, the second gate opens. If centrifugal force is being used then the head will continue in the dynamic hydropressure column to the hollow protuberance. If a substrate base is being used then the pumping means facilitates the movement of the sperm head into the hollow protuberance. The gates, being bimorphic, respond to controlled inputs (e.g., heat, electrical current) by changing their conformation, closing or opening.

In a specific embodiment, the ICSI MEMS device further comprises a coating to the mega-laminate after the final etching. The coating is to prevent the cells from adhering or sticking to the elements of the device. Preferably, the coating is a polypeptide, and more preferably, the polypeptide is poly-lysine.

The present invention also provides for an ICSI MEMS array or kit comprising at least one ICSI MEMS device affixed to a centrifugal platter. In a more specific embodiment, the ICSI MEMS device is permanently affixed to the centrifugal platter.

Figure 19:
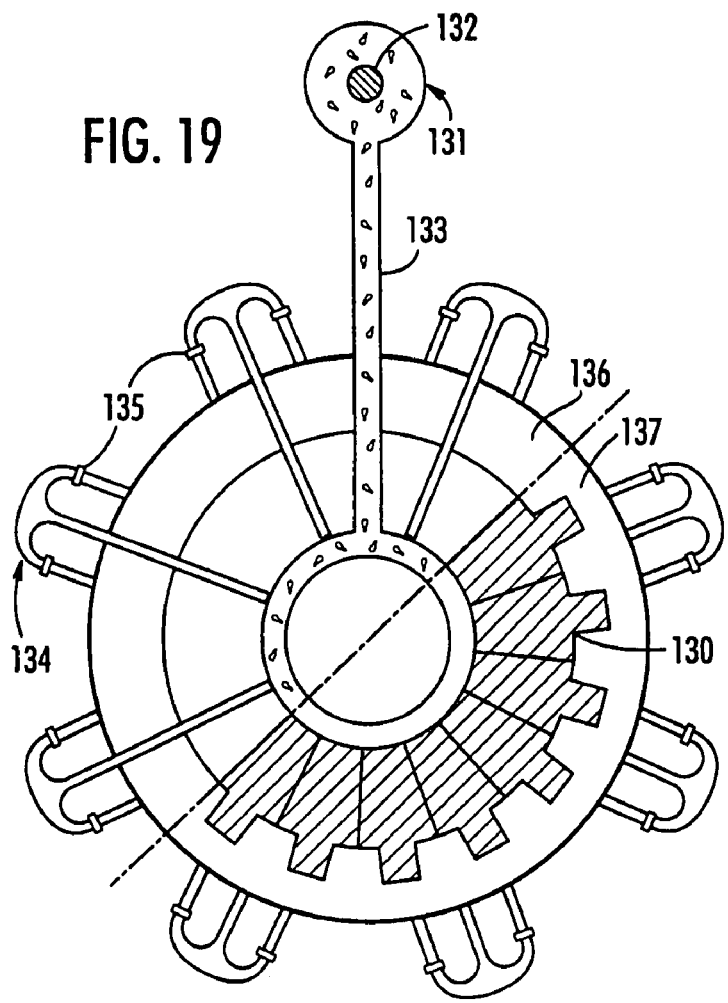
FIG. 19 is a cut-away view of an ICSI MEMS device.

FIG. 19 shows a preferred embodiment of an IntraCytoplasmic Sperm Injection (ICSI) MEMS array. This ICSI MEMS array comprises ICSI devices affixed to a centrifugal platter comprising a cell loading region 130, a sperm loading bay 131, and an opening in the sperm loading bay 131, a sealed or enclosed sperm channel 133 in fluid communication between the sperm loading bay 131 and the dynamic hydropressure columns 134, sperm guillotines 135 resident on each dynamic hydropressure column 134, microinjection needle 136, and well 137

In another embodiment, an ICSI MEMS device kit comprises an ICSI MEMS device permanently fixed onto the surface of a centrifugal platter and wherein:
  (a) the centrifugal platter having a plurality of grooves arranged in a concentric pattern on the centrifugal platter;
  (b) the ICSI MEMS device is bonded to the outer edge of said groove in an orientation such that the long axis of the ICSI MEMS device is horizontal to the plane of the centrifugal platter and directed towards the center of said platter; and
  (c) the inner surface of the grooves forming divided chambers which restrict the movement of materials from one compartment containing a single ICSI MEMS device to another such compartment.

In yet another embodiment, a method using an ICSI MEMS device comprises the steps of:
  (a) loading a fluid in the fluid handling means; loading sperm into the sperm loading manifold; loading a fluid into the wells;
  (b) loading at least one cell into each well;
  (c) applying an inertial force to the ICSI MEMS device by way of centripetal acceleration brought about by rotation of the centrifugal platter;
  (d) removing the distal portion of the sperm tail from the sperm using the sperm guillotine;
  (e) providing a variable fluid flow from the dynamic hydropressure column into the cell by operating a gating valve controlled by a circuit.
  a) and forcing the sperm head and fluid through dynamic hydropressure columns provides pressure to push sperm head and fluid into the cell.

Additionally, upon the oocyte or embryo being thrust upon the ICSI MEMS device, the ICSI MEMS device hollow protuberance, being in circuit lead communication with a controller, provides a pulse of energy (e.g., light, sound). The emission facilitates a focused opening in the lipid bi-layer of the oocyte or embryo plasma membrane for hollow protuberance penetration.

In one embodiment, the present invention provides for an ICSI MEMS device kit wherein
  (a) the centrifugal platter comprises a plurality of grooves arranged in a concentric pattern and wherein each groove has an inner and outer edge;
  (b) at least one ICSI MEMS device is bonded to the outer edge of a groove in an orientation such that the axis of each well of the ICSI MEMS device is horizontal to the plane of the compact cassette; and
  (c) the inner edge of the grooves forming divided compartments comprising a single well which restrict the movement of materials from one compartment containing a containing a single well to another compartment.

In a more specific embodiment, a method of using an ICSI MEMS device kit of comprises the steps of:
  (a) filling the input manifold of at least one ICSI MEMS device with a fluid;
    loading the fluid-filled wells of step (b) with at least one oocyte or embryo;
  (b) placing the ICSI MEMS/centrifugal platter into a centrifuge; and
  (c) applying a centripetal force on the ICSI MEMS/centrifugal platter.

In another specific embodiment, a method of using an ICSI MEMS device kit comprises the steps of:
  (a) filling the grooves of the centrifugal platter with a fluid;
  (b) loading the grooves of the centrifugal platter with at least one oocyte or embryo;
  (c) applying a centripetal force to the kit whereby the oocyte or embryo makes contact with the pertuberance of the ICSI MEMS device and the pertuberance penetrates the surface of the oocyte or embryo; and
  (d) severing the sperm head from the tail by sperm guillotine and positioning the sperm head near tip of hollow protuberance.
  depositing one sperm head in the oocyte or embryo. The present invention also provides for methods of making ICSI MEMS devices as described in Section A supra.

In one embodiment, a method of making an ICSI MEMS device comprises;
  (a) etching a plurality of channels in parallel on a silicon wafer;
  (b) bonding of said first wafer to the unetched side of a second identically made etched wafer such that all etched channels are in parallel;
  (c) repeat step (b) until desired number of wafers have been fused to form a mega-laminate;
  (d) said mega-laminate is cut at an angle perpendicular to the axis of said etched channels;
  (e) the slice of mega-laminate formed in (d) is bonded to the etched side of a channel-etched base-plate wafer;
  (f) a first mask is deposited on the surface of mega-laminate, the side not being bonded to the channel-etched base-plate wafer, such that a square region surrounding each square center void region is free of mask;
  (g) said mega-laminate surface with mask of (f) being etched such that the mega-laminate wafer material is removed to form a plurality of wells in the mega-laminate wafer;

(h) a mask is deposited on the surface of said mega-laminate which is not bonded to the channel-etched base-plate wafer such that the mask forms a border surrounding each well in the mega-laminate;

(i) said mega-laminate surface with the mask of (h) is etched such that the mega-laminate wafer material is removed to a depth wherein material remains above the channel-etched base-plate wafer, forming a plurality of hollow protuberances of a certain height and width.

In a specific embodiment, the method of making an ICSI MEMS device further comprises applying a coating to the mega-laminate after the final etching. Preferably, the coating is a polypeptide, and more preferably, the polypeptide is poly-lysine.

The present invention provides for a method of using an ICSI MEMS device. The invention further provides for a method of using an ICSI MEMS device comprising the ICSI MEMS device being affixed to a means for applying centripetal forces to said ICSI MEMS device. The invention further provides for a method of using an ICSI MEMS device comprising the ICSI MEMS device being affixed to a means for applying centripetal forces to said an ICSI MEMS device further comprising a well for receiving an oocyte communicating directly with an ICSI MEMS device such that when a centripetal force is applied the oocyte contained within the well communicating with the ICSI MEMS device is forced against the ICSI MEMS device such that the ICSI MEMS device hollow protuberance penetrates through the zona pellucida, through the oollema, and into the cytosolic compartment of the oocyte.

The invention further provides that upon the penetration of the oocyte by the ICSI MEMS device, a sperm, having been decapitated, travels through the ICSI MEMS device and into the cytosolic compartment of the oocyte. The present invention further provides for the maintenance of a positive pressure in the ICSI MEMS device.

The present invention provides for a method of manufacture of an ICSI MEMS device wherein a silicon wafer is modified by silicon etchant/modifying technologies (e.g., deep silicon reactive ion etching, silicon surface micromachining, LIGA).

After alternative method of making the ICSI MEMS devices of the present invention is substantially similar to the method described immediately above wherein the structures formed are: sperm bay, enclosed channel in fluid communication between the sperm loading bay and the central manifold that is in turn in fluid communication with the dynamic hydropressure column, sperm guillotine/gating element on each dynamic hydropressure column and also in fluid communication with the hollow protuberance in the cell well, and a cell loading region.

Alternatively, the sperm guillotine can be located between the sperm loading bay and the central manifold and a gating element on each dynamic hydropressure column to allow only one sperm to enter or oocyte.

In another embodiment, the present invention provides for an ICSI MEMS device kit for the injection of a sperm into a cell comprising:

(a) a pumping/sperm guillotine base providing support and a pump; and (b) at least one ICSI MEMS device affixed to the base.

Yet another method of making an ICSI MEMS is substantially similar to that method of making a microinjection MEMS device as recited above with the following modifications: the hollow protuberance is at least 1.5 µm in width and as wide as 7.5 µm; a sperm guillotine/gate element is constructed in the fluid handling means between a sperm loading bay and the hollow protuberance.

Zona Coring MEMS

Infertility can arise from a great many different factors, one of which is the hardening of the zona pellucida of the oocyte in some women. While the developing embryo is normally capable of moving through and out of the zona pellucida after a certain number of divisions (hatching), it is the case that, with a hardened zona pellucida, the embryo is trapped and can not escape, leading to a failure to implant and a failure of pregnancy. To eleviate this condition a technique known as "assisted hatching" has been developed in which a portion of the surface of the zona pellucida is eroded to such an extent that the developing embryo can hatch. This technique represents a significant investment in highly specialized equipment, extensive training, and scarce gamete resources. Further, pregnancy outcomes are highly dependent on the skill of each individual performing the assisted hatching. A device which would facilitate the automation and standardization of this technique would offer significant advantages over the present state of the art.

The present invention further provides for zona coring MEMS devices and kits that remove a small portion of the zona pellucida and thus facilitate assisted hatching of an embryo.

In one embodiment, a zona coring MEMS device comprises a silicon wafer comprising a plurality of wells wherein each well comprises at least one coring member. A coring member is for creating the holes or cores in the zona.

The present invention also provide for a zona coring MEMS device kit comprising: (a) at least one zona coring MEMS device of claim 1; and (b) a centrifugal platter having an outer edge and a plurality of grooves, the grooves having an inner and outer surface, arranged in a concentric pattern on the surface of the centrifugal platter; wherein the zona coring MEMS device is attached to the outer edge of the centrifugal platter in an orientation such that the long axis of each of the cell wells of the zona coring MEMS device is horizontal to plane of the centrifugal platter and the inner surface of the grooves forming divided chambers, the chamber containing a single cell well, which restrict the movement of materials from chamber to another such chamber.

In a particular embodiment, a zona coring MEMS device for forming one or more cores in the zona pellucida of a cell comprising a substrate wherein the substrate comprises a plurality of wells and wherein each well comprises coring member In another embodiment, a zona coring MEMS device kit for forming one or more cores in the zona pellucida of a cell comprises:

(a) a centrifugal platter having an outer edge and a plurality of grooves, the grooves having an inner and outer surface, arranged in a concentric pattern on the surface of the centrifugal platter wherein the centrifugal platter is for applying a centrifugal force to the; and (b) at least one zona coring MEMS device of claim 1.

The present invention also provides for a method of using the zona coring MEMS device kit comprising the steps of:

1. filling the grooves of the centrifugal platter with a fluid;
2. loading the fluid in the grooves of the centrifugal platter with at least one oocyte or embryo;
(c) applying centripetal forces to the kit such that the oocyte or embryo makes contact with the coring member of the zona coring MEMS device and the coring member penetrates the zona of the oocyte or embryo forming at least one zona fragment; and (d) cessation of centripetal force;

In another embodiment, the method of using a zona coring MEMS device comprises the zona coring MEMS device being affixed to a centrifugal platter and applying centripetal force to said zona coring MEMS device. To use the zona coring MEMS device a centripetal force is applied to the oocyte or embryo contained within the well the device thereby communicating with the zona coring MEMS device, the embryo is forced against the zona coring MEMS device such that the coring means penetrates and attaches onto the zona pellucida of the oocyte or embryo and creates an opening in the zona.

The invention further provides that upon the penetration of the zona pellucida of the oocyte or embryo by the zona coring MEMS device and upon the termination of the centripetal force, the portion of the zona pellucida penetrated by and attached to by the coring means remains attached to the zona coring MEMS device upon removal of the oocyte or embryo from the well.

The present invention provides for a method of making a zona coring MEMS device wherein a silicon wafer is modified by silicon etchant/modifying technologies (i.e., deep silicon reactive ion etching, silicon surface micromachining, LIGA). A variety of methods of making MEMS structure known to those skilled in the art. We describe below preferred methods of making the zona coring devices.

In other embodiments, a method of using the zona coring MEMS device kit comprises the steps of:
(a) filling the grooves of the centrifugal platter with a fluid;
(b) loading the fluid in the grooves of the centrifugal platter with at least one oocyte or embryo; and
(c) applying centripetal forces to the kit such that the oocyte or embryo makes contact with the coring member of the zona coring MEMS device and the coring member penetrates the zona of the oocyte or embryo thereby forming a core;

The present invention also provides for a method of making a zona coring MEMS device comprising the steps of:
(a) applying a first mask layer to a silicon wafer such that a plurality of wells are inscribed;
(b) etching the first mask applied in step (a) to form the plurality of wells;
(c) applying a second mask to the substrate within each etched well such that a coring member is inscribed within the well; and
(d) etching the second mask applied in step (c) to form a coring member.

In a preferred embodiment, a method of making a zona coring MEMS device comprises the steps of:
(a) applying a first mask to a silicon wafer such that a plurality of wells are inscribed;
(b) etching the first mask applied in step (a) to form a well;
(c) applying a second mask to the silicon wafer within each etched cell wells such that a coring member is inscribed within the well; and
(d) etching the second mask applied in step (c) to form a coring member.

Figure 21A:
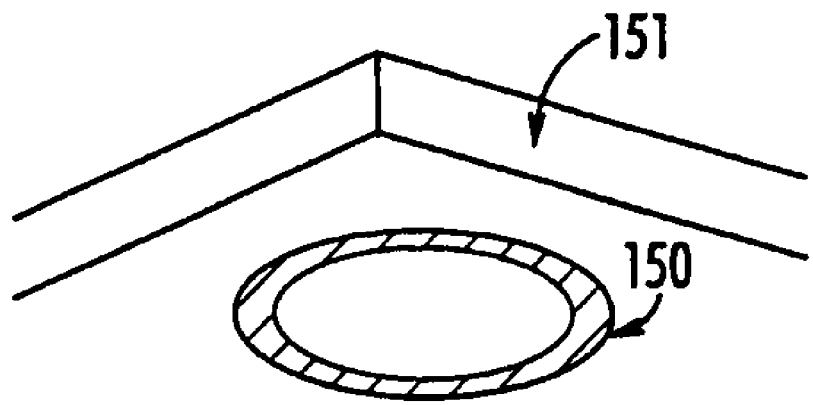
FIG. 21A is a perspective view of the first mask of a zona coring MEMS device in the cell well.
Figure 21B:
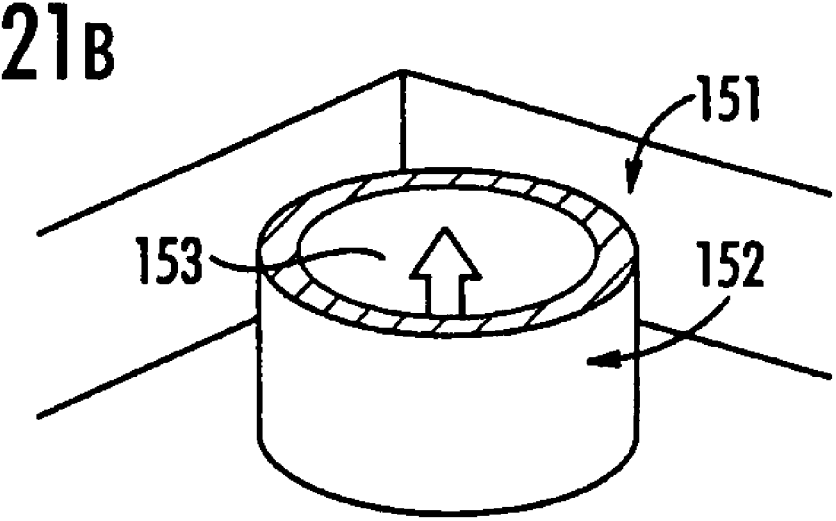
FIG. 21B is a perspective view of a cell well of a zona coring MEMS device showing the zona coring MEMS structure and barbed penetrating member.

A method of making the zona coring MEMS device is illustrated in FIGS. 21A and B. FIG. 21A shows a first mask 150 being applied to form a zona coring MEMS device and FIG. 21B shows the results of etching said mask. In FIG. 21A within a well 151 a mask 150 is deposited to protect a circular structure from etching. FIG. 21B shows that within a well 151 the coring structure 152 within which there is a coring member 153 such as a barbed coring member.

Enucleation MEMS

The technique of nuclear transfer, also known as cloning, requires the enucleation or removal of the genetic material from the donor oocyte. Enucleation is commonly performed using a micropipette by placing the micropipette in the cytoplasm of an oocyte in a region containing the genetic material or nucleus and removing it through the micropipette. In most species is it is difficult to locate the genetic material or nucleus because the cytoplasm may be relatively opaque or the nuclear membrane may be relatively translucent.

Current methods of enucleation are not optimal for removing the genetic material with great efficiency and often the removal of excess cytoplasm is unavoidable. This technique represents a significant investment in highly specialized equipment, extensive training, and scarce gamete resources. Further, enucleation efficiencies are highly dependent on the skill of each individual performing the enucleation. A device that would facilitate the automation and standardization of this technique would offer significant advantages over the present state of the art.

The term "enucleation" refers to the process by which the nuclear material of an oocyte or early embryo is removed using needles and handling system similar to those described for microinjection. Removal of the nucleus creates a recipient cell or cytoplast for the transplant of a donor cell or nucleus that occurs during nuclear transfer.

The present invention further provides enucleation MEMS devices and kits that are useful in the removal of the genetic material or nucleus, thereby facilitating enucleation of an oocyte or embryo. Further, the present invention provides methods of using the enucleation MEMS devices and kits. Lastly, the present invention provide for methods of making enucleation MEMS devices.

In one embodiment, an enucleation MEMS device for removing the nucleus from a cell or group of cells comprises a substrate comprising a plurality of wells for holding a cell or group of cells to be enucleated, wherein the wells comprise;
(i) an enucleation penetration member for penetrating a cell to isolate the nucleus from the cell; and
(ii) an enucleation pit below the enucleation penetration member for receiving the nucleus.

In another embodiment, an enucleation MEMS device further comprises:
a) a slidable shutter adjacent to the union between the enucleation penetration member and the enucleation pit for severing a portion of the cell containing the nucleus; and
(b) a controller in communication with the slideable shutter through a circuit lead.

Another embodiment of the present invention provides for an enucleation MEMS device kit comprises:
(a) at least one enucleation MEMS device attached to a top surface of
(b) a centrifugal platter for applying a centripetal force to a cell or group of cells contained within a MEMS device and wherein the centrifugal platter comprises a circular disk, a plurality of ports for holding the MEMS devices, and a securing means for attaching to a spinner or driving means.

In a specific embodiment, the enucleation MEMS device is permanently affixed to the centrifugal platter.

In a specific embodiment, the enucleation/nuclear transfer MEMS device the hollow protuberance is an emittor. Additionally, the device encompasses when the enucleation penetration member is an emittor.

In another embodiment, the enucleation/nuclear transfer MEMS device kit comprises:
  (a) a base substrate comprising an input well for depositing a cell, a lever element for controlling the cell apposition and a micropump for handling fluids; and
  (b) an enucleation/nuclear transfer MEMS device.

In another embodiment, an enucleation MEMS device for enucleating a cell comprising:
  (a) a base substrate comprising;
    (i) an input well to introduce a cell;
    (ii) a lever to control the motion of the cell; and
    (iii) a pump for applying a force to extrude a portion of the cell; and
  b) an enucleation MEMS device.

The present invention also provides for a method of making an enucleation MEMS device comprises the steps of:
  (a) depositing a first mask on the top surface of a substrate inscribing a square shape;
  (b) etching the first mask to form a plurality of wells;
  (c) depositing a second mask in the wells of step (b) such that an enucleation penetration member is inscribed at the bottom of each well;
  (d) etching the second mask (g) to form the enucleation penetration member;
  (e) applying a third mask within each well adjacent to the enucleation penetration member such that an enucleation pit is inscribed;
  (f) etching mask (i) to form the enucleation pit;
  (g) applying a fourth mask such that a slidable shutter is inscribed;
  (h) etching mask (k) to form the slideable shutter; and
  (i) depositing a circuit lead to provide communication between the shutter and a controller.

In a particular embodiment the enucleation MEMS device kit comprises:
  (a) a centrifugal platter comprises a plurality of grooves arranged in a concentric pattern and wherein each groove has an inner and outer edge;
  (b) at least one enucleation MEMS device is bonded to the outer edge of a groove in an orientation such that the axis of each well of the enucleation MEMS device is horizontal to the plane of the centrifugal platter; and
  (c) the inner edge of the grooves forming divided compartments comprising a single well that restricts the movement of materials from one compartment containing a single well to another compartment.

The present invention also provides a method of using the enucleation MEMS device kit comprising:
  (a) filling the grooves of the centrifugal platter with a fluid;
  (b) loading the fluid within the grooves of the centrifugal platter with at least one oocyte or embryo;
  (c) rotating the kit such that centripetal forces are applied to the centrifugal platter such that the oocyte or embryo are thrust against the wall of the cell well such that the enucleation penetration member of the enucleation MEMS device penetrates the surface of the oocyte or embryo; and
  (d) a portion of the cell contents containing the nucleus are extruded out of oocyte or embryo into the enucleation pit.

In a specific embodiment, a method of using the enucleation MEMS device kit comprises the steps of:
  (a) filling the grooves of the centrifugal platter with a fluid;
  (b) loading the fluid in the grooves of the centrifugal platter with at least one oocyte or embryo;
  (c) applying centripetal forces to the centrifugal platter by rotating the kit such that the oocyte or embryo are thrust against the wall of the cell well such that the enucleation penetration member of the enucleation MEMS device penetrates the surface of the oocyte or embryo;
  (d) extruding cell contents out of oocyte or embryo into the enucleation pit; and
  (e) severing a remnant of cell that has extruded into the extrusion pit using a slideable shutter.

In a more specific embodiment, the enucleation MEMS device further comprises a slideable shutter element at the union between the base of the enucleation penetration member and the enucleation pit.

Alternatively, an embodiment of the invention provides an enucleation MEMS device array comprising: a plurality of cell wells wherein each cell well contains an enucleation penetration member, each cell well is in fluid communication with an evacuation siphon, and a compressible substance is contained within the evacuation siphon.

In a more specific embodiment, an enucleation MEMS device further comprises a slidable shutter member between each enucleation penetration member and each evacuation siphon. The present invention also provides for an alternative method of using the enucleation MEMS device comprising:
  (a) filling an input well with a fluid;
  (b) loading the input well with an oocyte or embryo; and
  (c) applying a centrifugal force by rotating the enucleation MEMS device.

The present invention also provides for an enucleation MEMS device kit comprising:
  (a) at least one enucleation MEMS device; and
  (b) a centrifugal platter for applying a centripetal force to a cell or group of cells contained within a MEMS device and wherein the centrifugal platter comprises a circular disk having a plurality of ports for holding the MEMS devices, and a securing means for securing the platter to a spinner or driving means. In another embodiment, an enculeation MEMS device kit comprises:
  (a) at least one enucleation MEMS device attached to a top surface of
  (b) a substrate base wherein the substrate base comprises a lever for applying a force to the oocyte or embryo thrusting it against the enucleation MEMS device and a fluid handling means with pump in fluid communication with the enucleation pit and thus providing suction to the enucleation pit.

The present invention provides for a method of using an enucleation MEMS device. The invention further provides for a method of using an enucleation MEMS device comprising an enucleation MEMS device being affixed to a means for applying centripetal forces to said enucleation MEMS device. The invention further provides for a method of using an enucleation MEMS device comprising the enucleation MEMS device being affixed to a means for applying centripetal forces to said enucleation MEMS device further comprising a well for receiving an oocyte or embryo communicating directly with an enucleation MEMS device such that when a centripetal force is applied the oocyte or embryo contained within the well communicating with the enucleation MEMS device, the oocyte or embryo is forced against the enucleation penetration member of the enucleation MEMS device such that the enucleation penetration member of the enucleation MEMS device penetrates the zona pellucida and the oollemma of the oocyte or embryo.

The invention further provides that upon the penetration of the zona pellucia and oollemma of the oocyte or embryo by the enucleation penetration member of the enucleation MEMS device the centripetal force facilitates the migration of the genetic material through the opening in the oolllemma and the zona pellucida and into the enucleation pit of the enucleation MEMS device. The invention further provides that upon the termination of the centripetal force the genetic material, having migrated into the enucleation pit of the enucleation MEMS device, remains in the enucleation pit of the enucleation MEMS device upon removal of the oocyte from the pit. Further, the invention provides for an enucleation guillotine or enucleation slideable shutter that facilitates the severance of any connection between the genetic material in the enucleation pit and the oocyte or embryo. The present invention provides for a method of manufacture of an enucleation MEMS device wherein a silicon wafer is modified by silicon etchant/modifying technologies (e.g., deep silicon reactive ion etching, silicon surface micromachining, LIGA). Methods of making MEMS devices are set forth in particular in Section A Supra.

Figure 22A:
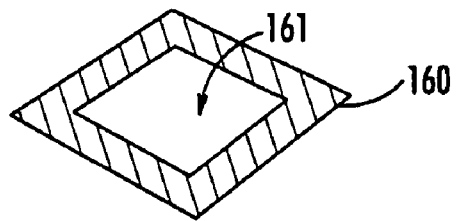
FIGS. 22A-E are representations of a series of masks (hatched area) for the manufacture of an enucleation MEMS device.
Figure 22B:
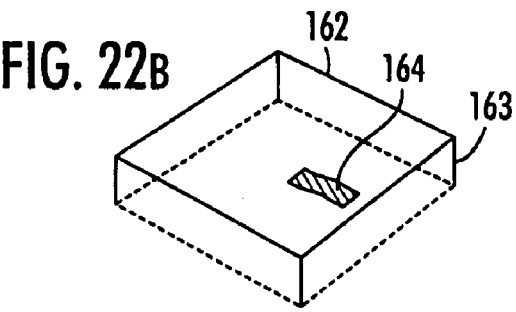
Figure 22C:
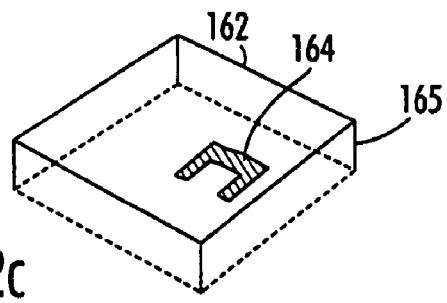
Figure 22D:
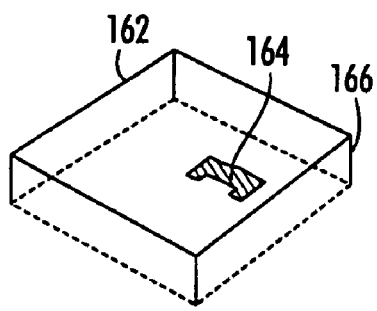
Figure 22E:
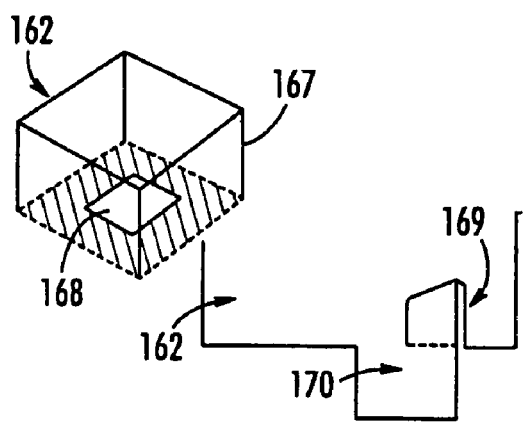

FIGS. 22A-E show a series of masks and etches that give rise to an individual MEMS device of an enucleation MEMS array. In FIG. 22A a first mask 160, is deposited on the surface of a wafer such that a square shape is inscribed 161. The first mask is etched and a well 162 is formed. A second mask 163 is deposited to begin formation of the enucleation penetration member 164. The second mask 163 is etched a third mask 165 is deposited and etched, a fourth mask is deposited and etched, and a fifth mask 167 protects formed enucleation penetration member and allows a central square to be etched such that an enucleation pit 168 is formed. FIG. 22E illustrates a side-view of the cell well 162 showing the enucleation pit 170, and the enucleation penetration member 169.

Figure 23:
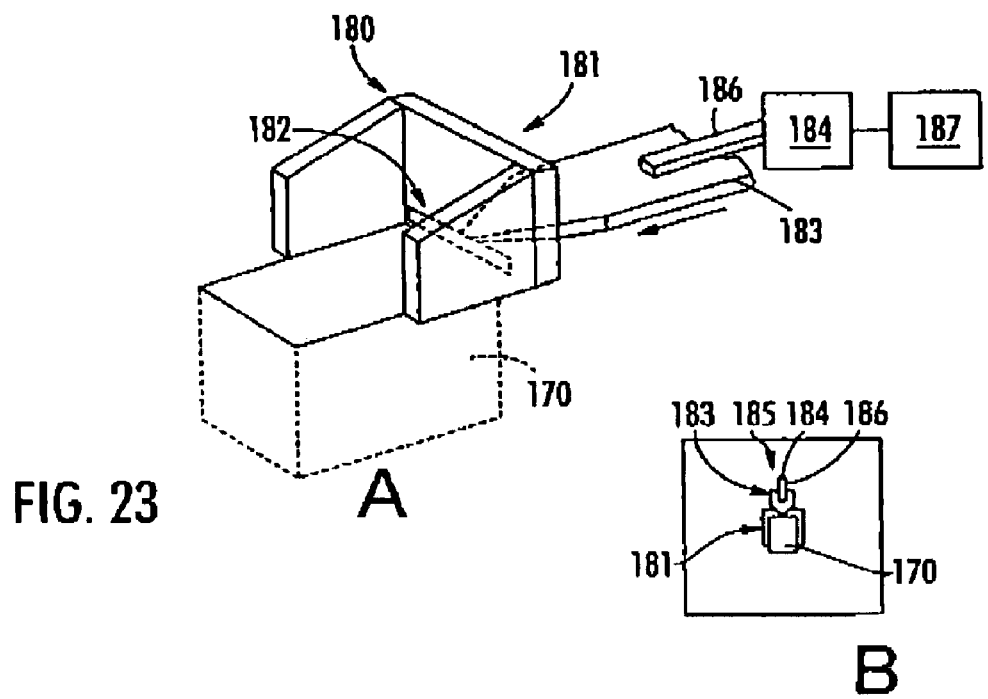
FIG. 23A is a side and cross-sectional view and 23B is a top view of an enucleation guillotine MEMS coupled to an enucleation MEMS device.

FIGS. 23A and B show a perspective and top view of an enucleation guillotine 180. In the union between the enucleation penetration member 181 and the enucleation pit 170 of an enucleation MEMS device there resides a slideable shutter door 182, and adjacent to the enucleation shutter door 182 is a slideable shutter 183 with a plane of movement illustrated by an arrow. This slideable shutter 183 is actuated by a controller 184 in communication with the shutter 183 by way of a circuit lead 185. the slideable shutter 183 is operated via a sliding means 186 activated by a gear assembly 187.

The present invention provides for a method of manufacture an enucleation MEMS device wherein a silicon wafer is modified by silicon etchant/modifying technologies (e.g., deep silicon reactive ion etching, silicon surface micromachining, LIGA). See Section A above.

A method of making an enucleation MEMS device comprising the modification of a substrate (i.e., silicon wafer, plastic, metallic oxide, other etchable and depositable substrate material) such that the etching and deposition of material on the substrate (i.e., LIGA, DRIE, silicon fusion bonding, laser etching, laser mediated and directed polymerization of substrate). Using these and other art-known MEMS fabrication methodologies the substrate is modified to form a central loading manifold, cell wells, evacuation siphon that is continuous with the enucleation penetration member containing in its end distal to the enucleation penetration member a compressible substance, an enucleation penetration member, and an enucleation guillotine or slideable shutter at the union between the enucleation penetration member and the portion of the evacuation siphon proximal to the enucleation penetration member.

In one embodiment, a method of making an enucleation MEMS device comprising the steps:
(a) etching a plurality of parallel channels on a first side of a plurality of silicon wafers in which the wafers each have a second unetched side;
(b) silicon fusion bonding the unetched side of a plurality of silicon wafers of step (a) to the etched side of a plurality of silicon wafers of step (a) such that the etched channels are in parallel to form a mega-laminate wherein the mega-laminate has a plurality of channels;
(c) cutting the mega-laminate at an angle perpendicular to the long axis of the etched channels thereby forming a slice of the mega-laminate having a top surface and a bottom surface wherein each surface exposes an end of the channel;
(d) silicon fusion bonding the bottom surface of the slice of the mega-laminate to the etched side of a channel-etched base-plate wafer;
(e) depositing a first mask on the top surface of the slice of the mega-laminate such that a region surrounding each channel end is free of mask;
(f) etching the mask to form a plurality of wells
(g) depositing a second mask in the wells of step (f) such that an enucleation penetration member is inscribed at the bottom of each well;
(h) etching the second mask (g);
(i) applying a third mask within each well adjacent to the enucleation penetration member such that an enucleation pit is inscribed;
(j) etching mask (i);
(k) applying a fourth mask such that a slidable shutter is inscribed;
(l) etching mask (k) and
(m) depositing a circuit lead in operable communication between the pump/valve and a controller In a specific embodiment, the method of making an enucleation MEMS device further comprises the step of applying a coating to the mega-laminate top surface after step (h). In more specific embodiments, the coating is a polypeptide, peptide or protein. In yet a more preferred embodiment, the polypeptide is polylysine.

In another embodiment, the method of making an enucleation MEMS device utilizes a method of making a channel-etched base-plate silicon wafer with a pump comprising the steps of:
(a) etching a silicon wafer with a plurality of channels which are in fluid communication with an input manifold reservoir;
(b) etching the silicon wafer of step (a) whereby a pump/valve is constructed in each channel; and
(c) depositing a circuit lead in operable communication between the pump/valve and a controller.

In a specific embodiment, the method of making a channel-etched base-plate silicon wafer with a pump further comprises attaching a piezoelectric pump/valve to the channels.

In one embodiment, the enucleation penetration member may be so constructed as to act as an emitter. In particular, the enucleation penetration member may act as a wave guide to conduct electromagnetic signals (e.g., pulses of light of any frequency). Additionally, the enucleation penetration member can provide vibrational energy (e.g., sound waves, e.g., ultrasonic waves).

N. Enucleation/Nuclear Transfer MEMS

As discussed in Section M, supra, the technique of nuclear transfer, also known as cloning, requires the removal of the genetic material or nucleus from the donor oocytes and the introduction of the donor nucleus into the recipient enucleated cell.

The term "nuclear transfer" refers to the process whereby a cell or nucleus of a cell is transplanted, using needles and the handling system similar to those described for microinjection, into an oocyte from which the nucleus has been removed (i.e., a recipient cell or cytoplast). This process gives rise to an embryo that carries the donor nuclei's genetic information.

Further, the introduction of a donor nucleus into the cytoplasm of the recipient cell requires either the introduction of a donor cell into the perivitelline space with a subsequent electropulse facilitating the fusion of the donor cell with the oocyte or the direct injection of either a donor cell or a donor nucleus. These techniques represent a significant investment in highly specialized equipment, extensive training, and scarce gamete resources. Further, enucleation as well as nuclear transfer efficiencies are highly dependent on the skill of each individual performing the procedures. A device that would facilitate the automation and standardization of these technique would offer significant advantages over the present state of the art.

The present invention provides for the enucleation/nuclear MEMS devices and kits for the removal of the genetic material of an oocyte or embryo, facilitating enucleation, as well as the simultaneous or subsequent injection of a donor cell or donor nucleus into the cytoplasm of the recipient oocyte or embryo. The present invention also provides for methods of using the enucleation/nuclear transfer MEMS devices and kits and methods of making same.

Figure 24A:
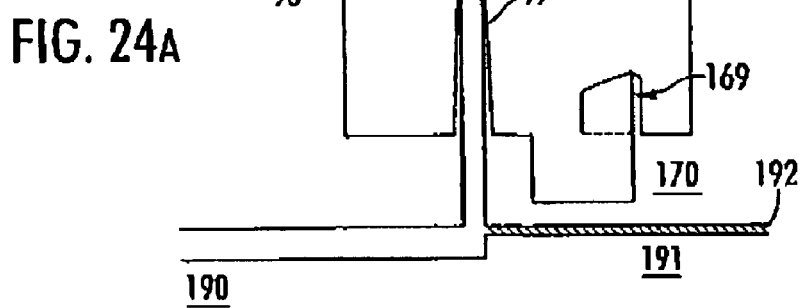
FIG. 24A is a side view of an enucleation/nuclear transfer MEMS device.
Figure 24B:
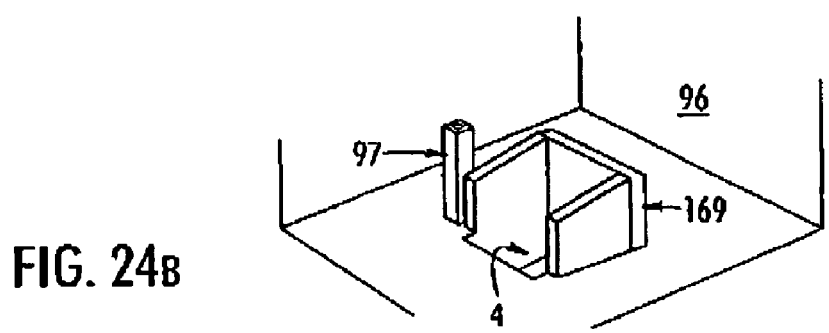
FIG. 24B is perspective view of an enucleation/nuclear transfer MEMS device.

FIGS. 24A and B illustrate specific embodiments of the present invention in a side cross-sectional view and perspective view a well of an enculeation/nuclear transfer MEMS device. FIG. 24A shows a well 96 with a microneedle or hollow protuberance 97 in fluid communication with a donor nucleus/cell injection channel 190, an enucleation pit 170, and an enucleation penetration member 169. Additionally, the position of the channel plate 191 and the silicon fusion bonded (sfb) interface 192 is shown. FIG. 24B shows the well 96 comprising the microneedle 97 or hollow protuberance, the enucleation penetration member 169, and the enucleation pit 170.

Figure 25A:
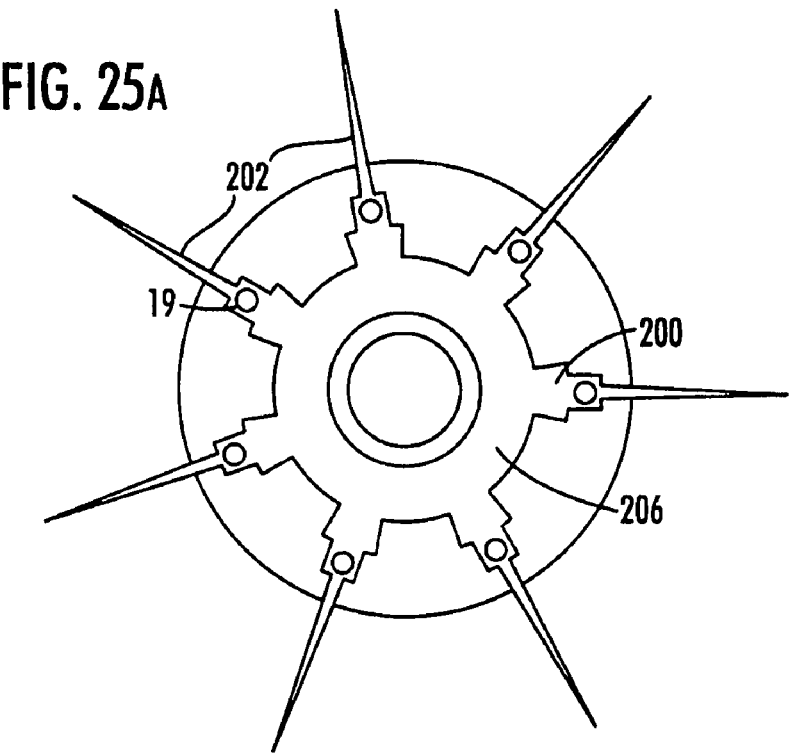
FIG. 25A is a top cut-away view of an enucleation MEMS device unit.
Figure 25B:
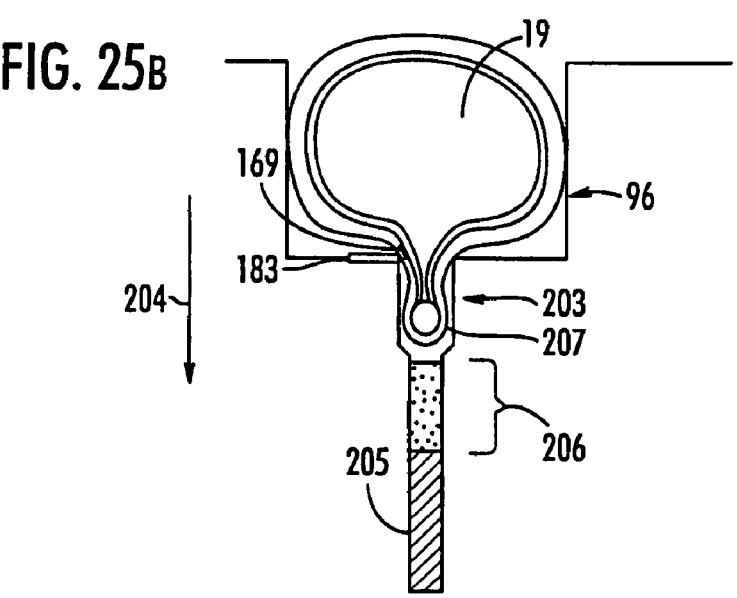
FIG. 25B is a side cross sectional view of a cell well of an encleation MEMS device.

FIGS. 25A-B show an enucleation/nuclear transfer MEMS array with a detailed inset view of an enucleation/nuclear transfer MEMS device. FIG. 25A shows a central loading manifold 206, a cell 19 in an input well 200 that is continuous with an enucleation/nuclear transfer MEMS unit 201 that has evacuation siphons 202. FIG. 25B shows a well 96, an enucleation siphon proximal portion 203 that receives an extruded portion of the cell 207 upon rotation of the array (arrow 204 points out direction of force generated upon rotation). The evacuation siphon distal portion 205 is filled with a compressible substance 206 that, upon rotation of the array pulls a partial vacuum at the proximal portion 203 such that the extrusion of the cell 19 is facilitated. A slideable enucleation shutter 183 below the enucleation penetration member 181 facilitates completion of the removal of the extruded portion of the cell 19.

Figure 26A:
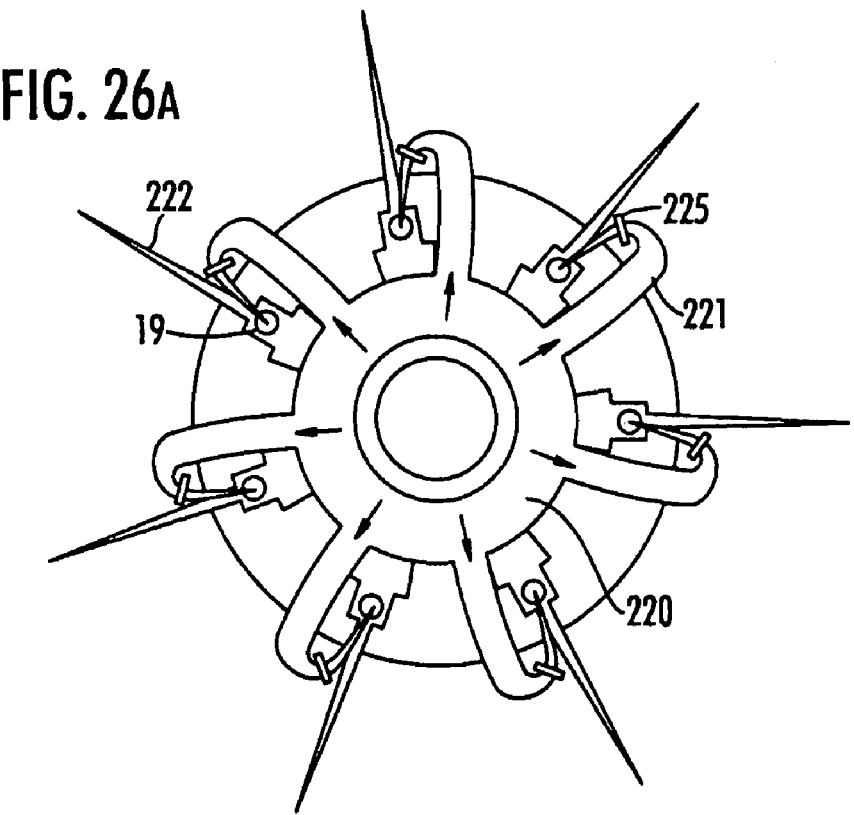
FIG. 26A is a cross-sectional view of one unit of an array of enucleation/nuclear transfer syphon.
Figure 26B:
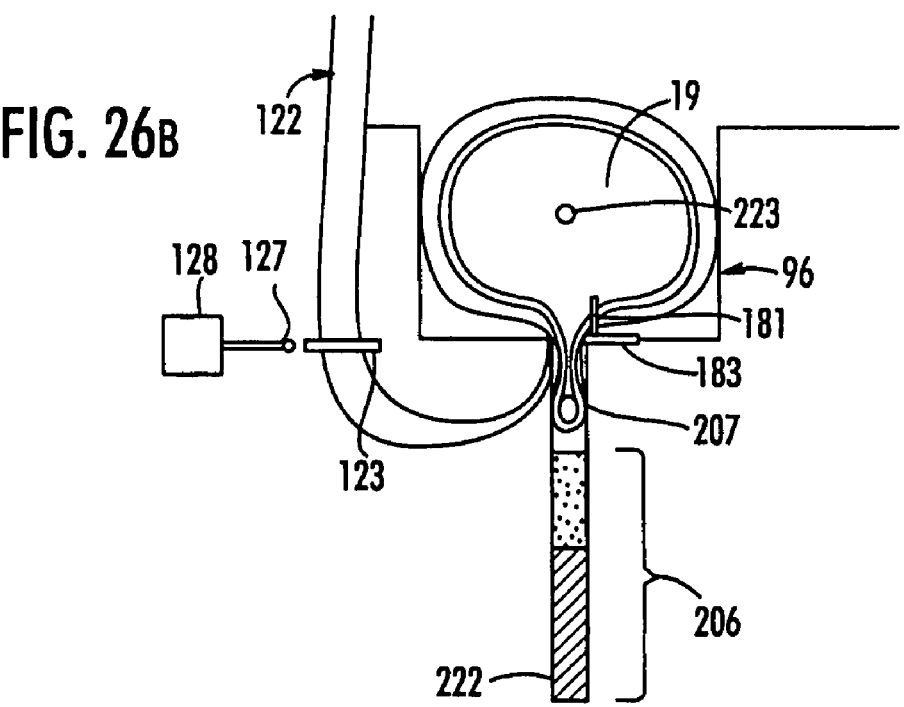
FIG. 26B is a side cross-sectional view of a cell well of an enucleation/nuclear transfer unit of a MEMS device.

FIG. 26A is another view one an enucleation/nuclear transfer MEMS device of an encleation/nuclear transfer MEMS array a central loading manifold 220 that is in fluid communication with the dynamic hydropressure column 221 with a gating element 225 that injects a donor nucleus or donor cell into the cell 19 and the extraction siphon 222 facilitates enucleation. FIG. 26B is a side cross-sectional view of an enucleation/nuclear transfer MEMS unit showing a cell 19 with its zona 223 in a well 96, an enucleation penetration member 181, a slideable enucleation shutter 183, an evacuation siphon 222 that has a compressible substance 206 that compresses upon rotation of the array, in part facilitating the extrusion of an extruded portion of a cell with a nucleus 207 into the enucleation siphon 222. The donor nucleus or donor cell 223 is simultaneously brought from the central loading manifold 220 (in FIG. 26A) through the dynamic hydropressure column 122, past a regulating valve 123, being actuated by a controller 128 in communication with the valve 123 by way of a lead 127, then injected through the hollow protuberance or microneedle 124 into the cell 19.

In one embodiment, an enucleation/nuclear transfer MEMS device for the enucleation and transfer of a donor nucleus or donor cell comprises a substrate comprising:
  (a) a central loading manifold for the loading of a cell or group of cells into the device;
  (b) at least one well for holding a cell during the enucleation process, wherein the well comprises:
    (i) a hollow protuberance in the well for penetrating the cell to introduce a donor nucleus;
    (ii) an enucleation penetration member for penetrating a cell to facilitate the removal of a cell nucleus;
    (iii) an enucleation evacuation siphon to provide suction to remove the nucleus from the cell forming an enucleated cell; and
  (c) a dynamic hydropressure column for providing a pressurized fluid to introduce the donor nucleus through the hollow protuberance into the enucleated cell.

In another embodiment, an enucleation/nuclear transfer MEMS device further comprises a gate on the dynamic hydropressure column for the modulation of fluid handling and allowance of a single donor nucleus or donor cell to pass through to the hollow protuberance for injection into the cytoplasm of the enucleated cell, such as an oocyte or embryo.

In another embodiment, an enucleation/nuclear transfer MEMS device further comprises a slideable shutter that operates at the union between the enucleation penetration member and the enucleation siphon.

The present invention also provides for a method of using enucleation/nuclear transfer MEMS device described above comprising the steps of:
  a) filling the enucleation/nuclear transfer MEMS device central loading manifold with a fluid;
  b) loading a donor nucleus or donor cell into the central loading manifold;
  c) loading the well with an oocyte or embryo; and
  d) applying a force to the enucleation/nuclear transfer MEMS device to facilitate the enucleation of the oocyte or embryo and the introduction of a donor nucleus or donor cell into the enucleated oocyte or embryo.

The present invention provides for a method of using an enucleation/nuclear transfer MEMS device comprising the enucleation/nuclear transfer MEMS device being affixed to a means for applying centripetal forces to said enucleation/nuclear transfer MEMS device. The invention further provides for a method of using an enucleation/nuclear transfer MEMS device comprising the enucleation/nuclear transfer MEMS device being affixed to a means for applying centripetal forces to said enucleation/nuclear transfer MEMS device further comprising a well for receiving an oocyte or embryo communicating directly with an enucleation/nuclear transfer MEMS device such that when a centripetal force is applied the oocyte or embryo contained within the well communicating with the enucleation/nuclear transfer MEMS device, is forced against the enucleation/nuclear transfer MEMS device such that the enucleation penetration member of the enucleation/nuclear transfer MEMS device penetrates the zona pellucida and the oollemma of the oocyte or embryo.

The invention further provides that upon the penetration of the zona pellucia and oollemma of the oocyte or embryo by the enucleation penetration member of the enucleation/nuclear transfer MEMS device, the centripetal force facilitates the migration of the genetic material through the opening in the oollemma and the zona pellucida and into the enucleation pit of the enucleation/nuclear transfer MEMS device while a donor nucleus or donor cell travels through the hollow protuberance of the enucleation/nuclear transfer MEMS device such that the donor nucleus or donor cell is injected into the cytoplasm of the enucleated oocyte or embryo. The invention further provides that upon the termination of the centripetal force the genetic material, having migrated into the enucleation well or evacuation siphon of the enucleation/nuclear transfer MEMS device, remains in the enucleation well or evacuation siphon of the enucleation/nuclear transfer MEMS device upon removal of the oocyte or embryo from the pit. The present invention further provides for the maintenance of a positive pressure in the microinjection means of the enucleation/nuclear transfer MEMS device. Further, the invention provides for an enucleation guillotine or enucleation slideable shutter element that facilitates the severance of any connection between the genetic material in the enucleation pit and the enucleated oocyte or embryo.

The present invention further provides for enucleation/nuclear transfer MEMS device kits comprising at least one enucleation/nuclear transfer MEMS device attached to a centrifugal platter to provide support and facilitate applying a centripetal force to the device.

In one embodiment, the enucleation penetration member may be so constructed as to act as an emitter. In particular, the enucleation penetration member may act as a wave guide to conduct electromagnetic signals (e.g., pulses of light of any frequency). Additionally, the enucleation penetration member can provide vibrational energy (e.g., sound waves, e.g., ultrasonic waves).

In another embodiment, the hollow protuberance may be so constructed as to act as an emitter. In particular, the hollow protuberance may act as a wave guide to conduct electromagnetic signals (e.g., pulses of light of any frequency). Additionally, the hollow protuberance can provide vibrational energy (e.g., sound waves, e.g., ultrasonic waves).

In a more specific embodiment, of the enucleation/nuclear transfer MEMS device kit, the enucleation/nuclear transfer MEMS device is permanently affixed to the centrifugal platter.

Alternatively, the present invention provides for enucleation/nuclear transfer MEMS device kits comprising at least one enucleation/nuclear transfer MEMS device attached to a substrate base to provide support and facilitate applying a force to the device.

Alternatively, the enucleation/nuclear transfer MEMS device of the present invention may be affixed to a substrate base as described previously for MEMS devices of the present invention wherein cell apposition to the enucleation/nuclear transfer MEMS device is mediated by a lever element and fluid handling by micropumps. Both the micropumps and the lever elements are actuated by a controller by way of circuit leads in communication between the micropumps, the lever elements and the controller.

In yet another more specific embodiment, the present invention provides for an enucleation/nuclear transfer MEMS device kit wherein (a) the centrifugal platter comprises a plurality of grooves arranged in a concentric pattern and wherein each groove has an inner and outer edge;

(b) at least one enucleation/nuclear transfer MEMS device is bonded to the outer edge of a groove in an orientation such that the axis of each well of the enucleation/nuclear transfer MEMS device is horizontal to the plane of the centrifugal platter; and (c) the inner edge of the grooves forming divided compartments comprising a single well which restrict the movement of materials from one compartment containing a containing a single well to another compartment.

The present invention also provides for a method of using the enucleation/nuclear transfer MEMS device kits comprising the steps of:
1. filling the input manifold of at least one enucleation/nuclear transfer MEMS device with a fluid;
2. loading the fluid-filled wells of step (b) with at least one oocyte or embryo;
3. rotating the kit and thus applying a centripetal force on the enucleation/nuclear transfer MEMS/centrifugal platter.

In another embodiment, a method of using an enucleation/nuclear transfer MEMS device kit comprises the steps of:
(a) loading donor nuclei or donor cells into the central loading manifold;
(b) filling the grooves of the centrifugal platter with a fluid;
(c) loading the grooves of the centrifugal platter with at least one oocyte or embryo;
(d) applying a centripetal force to the kit whereby the oocyte or embryo makes contact with the hollow protuberance of the enucleation/nuclear transfer MEMS device and the enucleation penetration member and thereby facilitating enucleation and nuclear transfer.

The present invention provides for a method of manufacture an enucleation/nuclear transfer MEMS device wherein a silicon wafer is modified by silicon etchant/modifying technologies (e.g., deep silicon reactive ion etching, silicon surface micromachining, LIGA).

A method of making an enucleation/nuclear transfer MEMS device comprising the modification of a substrate (i.e., silicon wafer, plastic, metallic oxide, other etchable and depositable substrate material) such that the etching and deposition of material on the substrate (i.e., LIGA, DRIE, silicon fusion bonding, laser etching, laser mediated and directed polymerization of substrate). Using these and other art-known MEMS fabrication methodologies the substrate is modified to form a central loading manifold, cell wells, dynamic hydropressure columns in fluid communication between the central loading manifold and the hollow protuberances in the cell wells, evacuation siphon that is continuous with the base of the enucleation penetration member containing in its end distal to the cell well a compressible substance, an enucleation penetration member, an enucleation guillotine or slideable shutter at the union between the enucleation penetration member and the portion of the evacuation siphon proximal to the enucleation penetration member. Further, this method of making may include a gate element on the dynamic hydropressure column that facilitate precise fluid control temporally and volumetrically, and allows a single donor nucleus or donor cell to pass through the hollow protuberance and into the enucleated oocyte or embryo.

In one embodiment, a method of making an enucleation/nuclear transfer MEMS device comprising the steps:
(a) etching a plurality of parallel channels on a first side of a plurality of silicon wafers in which the wafers each have a second unetched side;
(b) silicon fusion bonding the unetched side of a plurality of silicon wafers of step (a) to the etched side of a plurality of silicon wafers of step (a) such that the etched channels are in parallel to form a mega-laminate wherein the mega-laminate has a plurality of channels;
(c) cutting the mega-laminate at an angle perpendicular to the long axis of the etched channels thereby forming a slice of the mega-laminate having a top surface and a bottom surface wherein each surface exposes an end of the channel;

(d) silicon fusion bonding the bottom surface of the slice of the mega-laminate to the etched side of a channel-etched base-plate wafer;

(e) depositing a first mask on the top surface of the slice of the mega-laminate such that a region surrounding each channel end is free of mask;

(f) etching the mask to form a plurality of wells (g) depositing a second mask in the wells of step (f) such that an enucleation penetration member is inscribed at the bottom of each well;

(h) etching the second mask (g);

(i) applying a third mask within each well adjacent to the enucleation penetration member such that an enucleation pit is inscribed;

(j) etching mask (i);

(k) applying a fourth mask such that a slideable shutter is inscribed;

(l) etching mask (k) and (m) depositing a circuit lead in operable communication between the slideable shutter and a controller In a specific embodiment, the method of making an enucleation/nuclear transfer MEMS device further comprises the step of applying a coating to the mega-laminate top surface after step (h). The coating is to prevent the cells from adhering or sticking to the elements of the devices. In more specific embodiments, the coating is a polypeptide, peptide or protein. In yet a more preferred embodiment, the polypeptide is polylysine.

In another embodiment, the method of making an enucleation/nuclear transfer MEMS device utilizes a method of making a channel-etched base-plate silicon wafer with a pump comprising the steps of:

(a) etching a silicon wafer with a plurality of channels which are in fluid communication with an input manifold reservoir;

(b) etching the silicon wafer of step (a) whereby a pump/valve is constructed in each channel; and (c) depositing a circuit lead in operable communication between the pump/valve and a controller.

In a specific embodiment, the method of making a channel-etched base-plate silicon wafer with a pump further comprises attaching a piezoelectric pump/valve to the channels.

O. Cytoplasmic Transfer MEMS Array

The present invention provides cytoplasmic transfer MEMS devices, methods of using same and methods of making same.

A cytoplasmic transfer MEMS device facilitates the automated extraction of an aliquot of cytoplasm from a donor oocyte or embryo and the injection of that cytoplasmic aliquot into a recipient oocyte or embryo. This cytoplasmic transfer MEMS device can be fabricated in arrays of more than one cytoplasmic transfer MEMS device and as such can provide for the transfer of cytoplasm from many pairs of donor/recipient oocytes or embryos simultaneously. Cytoplasmic transfer is utilized in human Assisted Reproduction to ameliorate cytoplasmic insufficiencies in some patient oocytes or embryos.

In one embodiment, the present invention provides for a cytoplasmic transfer MEMS device for the transfer of cytoplasm from one cell to another comprising:

(a) a cytoplasmic transfer MEMS device comprising a substrate comprising:
(i) at least one first well wherein each first well compromises a hollow protuberance;
(ii) at least one second well wherein each second well compromises a hollow protuberance;
(iii) an extraction siphon in fluid communication with the hollow protuberance in the first well and with the hollow protuberance in the second well;
(iv) a supplemental input channel in fluid communication with the extraction siphon; and (b) a centrifugal platter for applying a centripetal force to a cell or group of cells contained within a MEMS device and comprises a circular disk having a plurality of ports for holding the MEMS device.

In another embodiment, a cytoplasmic transfer MEMS device further comprises:

a) a first valve on the extraction siphon proximal to first input well;
b) a supplemental input channel located between the first and second valves for providing fluid flow once the first gate closes and the second gate opens; and
c) a second valve on the extraction siphon distal to the supplemental input channel.

In yet another embodiment, the cytoplasmic transfer MEMS device has a supplemental input channel that enters the extraction siphon between the first valve and the second valve. Upon operation of the cytoplasmic transfer MEMS device a portion of the cytoplasm of the donor oocyte or embryo enters the extraction siphon, passes the open first valve, then the first valve closes. Isolating the cytoplasmic aliquot. Then fluid flow through the supplemental input channel, in fluid communication with the cell well, and the opening of the second gates allows the cytoplasmic aliquot to travel to and through the hollow protuberance in the second cell well and into the cytoplasm of the recipient oocyte or embryo.

Figure 27:
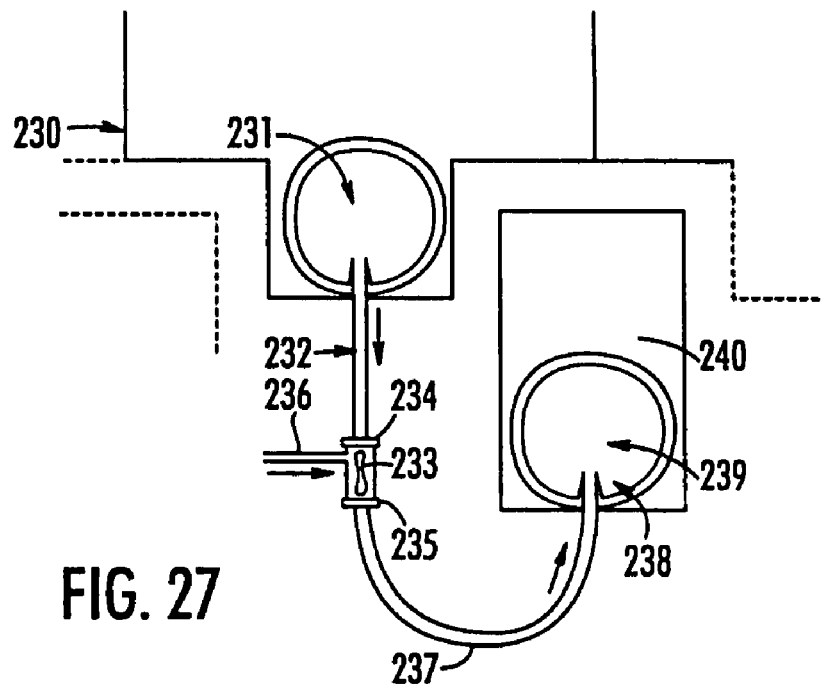
FIG. 27 is a side cross-sectional view of a single unit of a cytoplasmic transfer transfer MEMS device.

The present invention also provides a method of using a cytoplasmic transfer MEMS device comprising:

a) loading a fluid in the extraction siphon;
b) loading a cytoplasmic donor oocyte or embryo in the first well;
c) loading a recipient oocyte or embryo in the second well; and
d) applying a force to the cytoplasmic transfer MEMS device by rotating the array. FIG. 27 shows a preferred embodiment of a single cytoplasmic transfer MEMS device. A first well 230, receives a cytoplasmic donor oocyte or embryo 231 whereby upon application of a force and or suction to the cytoplasmic transfer MEMS device a cytoplasmic aliquot 232 is extruded into the extraction siphon—proximal portion 233 to the first gate 234 where upon the first gate 234 closes, the cytoplasmic aliquot 232, finding a second gate 235 closed, is stopped momentarily. Upon opening of the second gate 235 fluid from the supplemental input channel 236 the cytoplasmic aliquot 233 proceed through the extraction siphon—distal portion 237, through a hollow protuberance 12 and into a recipient oocyte or embryo 239 having been loaded into a second well 240.

The present invention provides for a method for making a cytoplasmic transfer MEMS device wherein a substrate (i.e., silicon wafer, plastic, metallic oxide, other etchable and depositable substrate material) is modified by art known methods of MEMS fabrication (i.e., LIGA, DRIE, silicon fusion bonding, laser etching, laser mediated and directed polymerization of substrate surface). These modification are applied to the substrate such that certain structures are formed and in particular for the cytoplasmic transfer MEMS device an extraction siphon, a first cell well with a hollow protuberance in fluid communication with the extraction siphon, a first gate, a supplemental input fluid handling means in fluid communication with the cell well, second gate are formed in the substrate, and a second cell well with a hollow protuberance in communication with the extraction siphon. These structures may be built or embedded on a spinnable platter, a centrifugal platter, for the ability to provide centripetal to the cytoplasmic transfer MEMS device.

Alternatively, these structures may be built in or affixed to a substrate base that provides fluid handling by way of micropumps and cell apposition to the cytoplasmic transfer MEMS device by way of a lever element. Further, the micropumps and lever elements are in communication with a controller by way of circuit leads.

The following examples are presented for purposes of illustration only and are not intended to limit the scope of the invention in any way.

EXAMPLES

The following protocols and experimental methods and materials are employed in the Examples that follow.

Superovulation

Mice (i.e., RB Swiss, (CBA*C57BL6/J)fl) are given 5 i.u./ml Pregnant Mares Serum Gonadotrophin (PMSG) interperitoneally (i.p.). At 46 to 48 hours post injection a second injection is i.p. administered providing 5 i.u./ml Human Chorionic Gonadotrophin (hCG) in Phosphate Buffered Saline (PBS). If mating is desired, females are placed with males immediately.

Blastocyst Flush

The uterus is removed from 3.5 day pregnant mice and placed into sterile PBS. Using a sterile fine forceps the mesometrium is trimmed and the ovaries, oviducts, the uterotubal junction, and the cervical bifurcation are dissected from both of the uterine horns. The uterine horn is flushed using a syringe of DMEM (Dulbecco's Modification of Eagle's Medium (Mod.) 1X (DMEM) with L-Glutamine, 4.5 g/L Glucose and Sodium Pyruvate; Fisher Scientific cat. #MT10013CM) with HEPES with a blunt-ended 23 gauze needle. Using sterile forceps, a uterine horn is picked up at one end and the blunt-ended needle is inserted just inside the open end of the horn. The syringe plunger is pushed and the horn is flushed with DMEM with HEPES medium into a sterile plastic dish. The horn is then flushed from other end. The remaining uterine horn is flushed in the same manner. Flushed blastocysts are now present in the sterile plastic dish. Using a transfer pipette blastocysts are collected and transferred into small drops of culture medium under an overlayment of sterile inert culture medium-equilibrated oil. Dishes with drops are incubated at 37° C. with 5% $CO_2$.

Blastocyst Transfer

Assay for Developmental Fitness of Manipulated Cells

Blastocyst transfer is performed 24 hours after aggregation when the morulae have become expanded blastocysts and on the same day as manipulation. Using Rompun/Ketavet at 0.02 ml/g body weight provide i.p. anesthesia to animals. To the shaved sterilized abdomen, an incision is made and the uterine horns exteriorized. A transfer pipette loaded with embryos and DMEM is inserted into the end of a uterine horn and the contents are expelled into the horn. After transfer of embryos into second horn the uterus is replaced into the body cavity, the wound is sealed with clips, and the animal allowed to recover. Offspring will be born approximately 16 days after transfer.

One-Cell Transfer into Pseudopregnant Recipient Female Mouse

After checking for cell fitness (i.e., cytoplasmic condensation, causing the cellular material to become less glossy and darker in color as the cytoplasm shrinks away from the Zona Pellucida pellucida, indicating a damaged cell) cells are transferred into a pseudopregnant recipient female mouse as before. Offspring will be born approximately 19-21 days after transfer.

Oocyte and Morula Harvest

After superovulation for oocytes and at 2.5 days p.c. (post coitus) for morulae, these cells are present in the oviducts. After animal sacrifice the oviducts are removed to sterile PBS. Oviducts are flushed with flushed into culture medium and morulae are collected, placed in drops of culture under oil, and incubated at 37° C. with 5% $CO_2$

Post Manipulation Viability Assays

Oocytes or embryos are placed in vital stain and then live-mounted onto slides. A microscope is used to determine if the vital stain has penetrated the cell membrane indicating cell injury.

Oocytes are placed in maturation culture and their ability to mature to the various checkpoints of oocyte maturation (Meiosis I, Meiosis II) is determined. Additionally, depending on stage of oocyte at time of manipulation and the type of manipulation, the oocyte in vitro fertilized to determine fitness for fertilization.

If further early embryonic development is to be assayed the fertilized embryos are replaced to in vitro culture and extent of development can be determined. If offspring are desired for the determination of effect of manipulation on oocytes or embryos the embryos must be transferred into a recipient animal and allowed to gestate.

Immunocytochemistry

Methanol Fixation

Cells are extracted in Microtubule Stabilizing Buffer (MTSB; 80 mM PIPES pH 6.8, 1 mM MgCl2, 4 mM EGTA)+ 0.5% TX-100 for 30 seconds. Cells then are fixed in −20° C. methanol for 1-2.5 minutes, rinsed in TBS 0.15 M NaCl, 0.02 M Tris-Cl pH 7.4), permeabilized in TBS-0.5% TX for 10 minutes, rinsed in TBS-0.1% Triton X, and stored in blocking medium.

Immunofluorescence

Primary antibody diluted in blocking medium is added to the cells for 1-3 hours. The cells are washed in TBS-0.1% TX and then secondary antibody is added to the cells for one hour. The cells are then washed in TBS-0.1% TX. If another primary antibody is to be used it can either be added when the first primary antibody was used or after the first secondary antibody is added and washed. For nuclear staining the cells are incubated in 1-10 ug/ml DAPI or Hoescht in blocking medium for 10 minutes. The cells are washed in TBS-0.1% TX and rinsed in TBS. The cells are then mounted on a slide with mounting medium (0.5% p-phenylenediamine (Free Base; Sigma) in 20 mM Tris, pH 8.8, 90% glycerol) and a coverslip is sealed over top with acrylic.

Example

Use of the Cell Labeling MEMS Device and the Labelable Zona Anchor MEMS Device

Operation of the Cell Labeling and Labelable Zona Anchor MEMS Devices

The cell labeling MEMS device kit (with the centrifugal platter) is placed onto a spinning device. Cell wells are filled with loading fluid (i.e., PBS/PVA, M199 media). The labelable zona anchor MEMS device is spun at 5 g for 10 seconds to purge bubbles. Oocytes or embryos are placed into cell wells by mouth pipette, robotic pipette, or other manner. Spinner is rotated at 5 g for 10 seconds and stop. Remove cells to incubated environment. (Alternatively, CPU controller on spinner provides a ramp up to 5 g then ramp down, 10 seconds duration).

Alternatively, the labelable zona anchor MEMS device can be situated on a substrate base that facilitates close opposition of the oocyte or embryo with the active domain of the labelable zona anchor MEMS device by way of a lever element. The lever element is actuated by a controller being in communication with these elements by way of circuit leads.

Determination of Labelable Zona Anchor MEMS Device being Embedded in Oocyte or Embryo Zona Pellucida Cells are observed by microscope to determine rates of successful attachment of labelable zona anchor MEMS device to the Zona Pellucida.

Determination of Effect of Labelable Zona Anchor MEMS Device on Oocyte and Embryo Viability, Developmental Progression and Cytoskeleton Cells are assayed for immediate effect of manipulation on cell viability (vital staining) as well as for developmental fitness (either early embryonic development or ability to produce offspring in recipient animal). Further, cells are processed for immunofluorescence to visualize microtubule and actin networks to determine effect of manipulation on the cytoskeleton.

Operation of Labelable Zona Anchor MEMS Device Platform

Cells that have labelable zona anchor MEMS device embedded in their Zona Pellucidas are exposed to a labelable zona anchor MEMS device platform that is in an labelable zona anchor MEMS device attractive state (i.e., the labelable zona anchor MEMS device channels of the platform are magnetized and thus attractive to magent-attractive labelable zona anchor MEMS devices). The labelable zona anchor MEMS device platform is observed under a microscope to determine whether labelable zona anchor MEMS device/cell conjugates have attracted to the labelable zona anchor MEMS device platform. The labelable zona anchor MEMS device platform with attached cells is then attached to a labelable zona anchor MEMS device platform holder and the holder is also loaded with culture media. Observation of ability of labelable zona anchor MEMS device/cells to remain attached to the labelable zona anchor MEMS device platform is made while the labelable zona anchor MEMS device platform is situated within the holder. The labelable zona anchor MEMS device platform/holder assembly is transported to a receiving docking domain (i.e., automatic multi-compartment multi-modal incubation device) and the platform is docked to the receiving docking domain (i.e., automatic multi-compartment multi-modal incubation device). Further observations for the determination of ability of labelable zona anchor MEMS device/cells to remain attached to the labelable zona anchor MEMS device platform are made at this time. Additionally, the platform holder with the extended handle in FIG. 5c is docked to a platform that holds labelable zona anchor MEMS device/cell conjugates. This labelable zona anchor MEMS device platform/holder is then used to insert the platform into the interior of an animal uterus (i.e., cow, goat, pig) and then the selectively magnetic platform is provided with input that instructs it to cease magnetic attraction to the labelable zona anchor MEMS device/cell conjugates. This procedure is monitored by ultrasound to provide proper positioning of the labelable zona anchor MEMS device platform/holder within the uterus. Upon removal of the labelable zona anchor MEMS device platform/holder from the animal the platform is observed for any remaining labelable zona anchor MEMS device/cell conjugates. When embryos have been used in this procedure, the animal is observed for pregnancy and delivery of young.

Example

The Zona Coring MEMS Device

Operation of Zona Coring MEMS Device

The Zona coring MEMS device kit with the centrifugal platter is placed onto a spinning device. Cell wells are filled with loading fluid (i.e., PBS/PVA, M199 media). The Zona Pellucida coring MEMS device is spin at high speed (i.e., 5 g, 6 g, 7 g) for 10 seconds to purge bubbles. Oocytes or embryos are placed into cell wells by mouth pipette, robotic pipette, or other manner. Spinner is rotated at high speed (i.e., 5 g, 6 g, 7 g) for 10 seconds and stop. Cells are removed to incubated environment. (Alternatively, CPU controller on spinner provides a ramp up to desired speed then ramp down).

Alternatively, the zona coring MEMS device can be situated on a substrate base that facilitates close opposition of the oocyte or embryo with the active domain of the zona coring MEMS device by way of a lever element. The lever element is actuated by a controller being in communication with these elements by way of circuit leads.

Determination of Successful Operation of the Zona Pellucida Coring MEMS Device

Oocytes or embryos that have undergone manipulation by the Zona Pellucida coring MEMS device are observed live under a microscope to determine whether a section of the Zona Pellucida, having been resected by the zona coring MEMS device, is not present.

Determination of Effect of Zona Coring MEMS Device on Oocyte or Embryo Viability and Developmental Fitness Cells are assayed for immediate effect of manipulation on cell viability (vital staining) as well as for developmental fitness (either early embryonic development or ability to produce offspring in recipient animal). In particular, embryos that have undergone this procedure are cultured to observe if the embryo is able to hatch through the hole in the zona as formed by the Zona coring MEMS device. Further, cells are processed for immunofluorescence to visualize microtubule and actin networks to determine effect of manipulation on the cytoskeleton.

Example

The Microinjection MEMS Device

Preparation of Fluids to be Injected

All fluids to be injected must be ultra-pure and preferably centrifuged (i.e., 5 g, 6 g, 7 g) prior to loading into the microinjection MEMS device.

Preparation of DNA for Injection

Recombinant plasmid is purified by CsCl gradient (see Molecular Cloning: A laboratory manual, $2^{nd}$ ed. Sambrook, et al. 1990). Release insert with restriction enzymes. The insert is separated from the vector on an agarose gel run in Tris/Acetate/EDTA buffer. Insert is eluted from excised gel slice. Fragment is recovered by ethanol precipitation and then passed over an ion exchange column (e.g. Schleicher & Shuell Elutip columns). DNA is Ethanol-precipitated and resolubilized in injection buffer (10 mM Tris/0.1 mM EDTA pH 7.5, using Milli-Q $H_2O$). DNA concentration is determined. DNA concentration is adjusted to 1-5 ng/µl with injection buffer.

Operation of Microinjection MEMS Device

The microinjection MEMS device/centrifugal platter cartridge is placed onto a spinning device. The central loading manifold is filled with loading fluid (i.e., PBS/PVA, M199 media, fluorescent dye, visible dye). The microinjection MEMS device is spun at 5 g for 10 seconds to purge bubbles and to load fluids throughout the dynamic hydropressure columns and hollow protuberances. Oocytes or embryos are placed into cell wells by mouth pipette, robotic pipette, or other manner. Spinner is rotated at 5 g for 10 seconds and stopped. Alternatively, the spinner is rotated at a lower speed (i.e., 1 g, 2 g, 3 g; providing for pronuclear positioning) for 5 seconds, pulsed at a higher speed (i.e., 5 g, 6 g, 7 g, providing needle penetration and injection of fluid into cell) and then stopped. Cells are removed to incubated environment. (Alternatively, CPU controller on spinner provides a ramp up to desired speed then ramp down).

Alternatively, the microinjection MEMS device can be situated on a substrate base that facilitates fluid movements through micropumping means and the oocyte or embryo can be brought into close opposition with the active domain of the microinjection MEMS device by way of a lever element. Both the micropumping means and the lever element are actuated by a controller being in communication with these elements by way of circuit leads.

Determination of Successful Operation of the Microinjection MEMS Device

Cells injected by the microinjection MEMS device loaded with fluorescent dye are observed by fluorescence microscopy to determine the deposition of fluorescent dye into the cytoplasmic compartment of the cell. Where the injection is pronuclear in manner fluorescence microscopy to determine the deposition of fluorescent dye into the nuclear compartment of the cell.

Cells injected by the microinjection MEMS device loaded with a reporter DNA construct (i.e., P-gal, luciferase) are processed to determine gene expression as per instructions by reporter DNA construct manufacturer.

Determination of Effect of Microinjection MEMS Device on Oocyte or Embryo Viability and Developmental Fitness Cells are assayed for immediate effect of manipulation on cell viability (vital staining) as well as for developmental fitness (either early embryonic development or ability to produce offspring in recipient animal). Further, cells are processed for immunofluorescence to visualize microtubule and actin networks to determine effect of manipulation on the cytoskeleton.

Cells injected by the microinjection MEMS device loaded with an expression DNA construct (i.e., gene of interest) are processed to determine gene expression as per instructions by expression DNA construct manufacturer.

Further, to determine efficacy of genes injected with the microinjection MEMS device, embryos modified with this device are transferred to recipient animals and allowed to gestate to appropriate stage of development or to birth.

Example

The IntraCytoplasmic Sperm Injection (ICSI) MEMS Device

Preparation of Sperm for Injection into Cells

Sperm washing removes non-competent cells and prostaglandins. Sperm are washed with Ham's F (HF)-10 medium to remove the seminal plasma, centrifuged (200×g, 300×g, 400×g) for a short time (5 minute, 6 minutes, 7 minutes) and resuspended in less than a milliliter of HF-10 medium.

The swim-up assay provides for the selection of non-pathologic morphology and motility. Washed semen is incubated at 37° C. for 1 hour in HF-10 medium. The uppermost fraction of tissue culture medium is collected, centrifuged, and resuspended in a smaller volume of HF-10 medium.

Operation of ICSI MEMS Device

The ICSI MEMS device/centrifugal platter cartridge is placed onto a spinning device. The cell loading region and the sperm loading bay is filled with loading fluid (i.e., Ham's F-10 Medium, PBS/PVA, M199 media, fluorescent dye, visible dye). The ICSI MEMS device is spun at high speed (i.e., 4×g, 5×g, 6×g) for 10 seconds to purge bubbles and to load fluids throughout the cell loading region, sperm loading bay, dynamic hydropressure columns and hollow protuberances. The sperm loading bay is seeded with an aliquot of concentrated, washed and capacitated sperm. Sperm are allowed to diffuse throughout the sperm loading bay and dynamic hydropressure columns. Oocytes are placed into cell wells by mouth pipette, robotic pipette, or other manner. Spinner is rotated at low speed (i.e., 2×g, 3×g, 4×g) for a short period (i.e., 8 seconds, 9 seconds, 10 seconds), simultaneously the sperm guillotine(s) are operated to isolate a single sperm per dynamic hydropressure column, sever it's tail and allow it to pass into the dynamic hydropressure column proximal to the hollow protuberances. After operation of sperm guillotine(s) the speed of rotation is ramped up to high speed (i.e., 5×g, 6×g, 7×g) for a short time (2 seconds, 3 seconds, 4 seconds)

and rotation is terminated. Cells are removed to incubated environment. (Alternatively, CPU controller on spinner provides a ramp up to desired speed then ramp down).

Alternatively, the ICSI MEMS MEMS device can be situated on a substrate base that facilitates fluid movements through micropumping means and the oocyte or embryo can be brought into close opposition with the active domain of the ICSI MEMS MEMS device by way of a lever element. Both the micropumping means and the lever element are actuated by a controller being in communication with these elements by way of circuit leads.

Determination of Successful Operation of the ICSI MEMS Device

Success of this procedure is measured by the presence of a single sperm in the cytoplasm of the oocyte. After operation of the ICSI MEMS device cells are removed to an organ culture dish and observed under a microscope for the presence of sperm.

Determination of Effect of ICSI MEMS Device on Oocyte or Embryo Viability and Developmental Fitness Embryos generated by the above method are tested for their ability to progress through early embryonic development. Embryos are collected at successive days and observed by microscope for cell division, morula formation and blastocyst development.

Example

The Enucleation MEMS Device

Operation of the Enucleation MEMS Device

The enucleation MEMS device/centrifugal platter cartridge is placed onto a spinning device. The central loading manifold is filled with loading fluid (i.e., Ham's F-10 Medium, PBS/PVA, M199 media, fluorescent dye, visible dye). The enucleation MEMS device is spun at high speed (i.e., 4×g, 5×g, 6×g) for 10 seconds to purge bubbles and to load fluids throughout the cell loading region. Oocytes or embryos are placed into cell wells by mouth pipette, robotic pipette, or other manner. Spinner is rotated at low speed (i.e., 2×g, 3×g, 4×g) for a short period (i.e., 8 seconds, 9 seconds, 10 seconds), bringing the cells into contact with the enucleation penetration member. The speed of rotation is ramped up to high speed (i.e., 5×g, 6×g, 7×g) for a longer period of time (5 seconds, 10 seconds, 15 seconds) to allow penetration of oocytes or embryos by the enucleation penetration member, to allow the extrusion of cell cytoplasm and nucleus, allow the severance of any cell remnant by the slideable shutter at the base of the enucleation penetration member, and then rotation is terminated. Cells are removed to incubated environment. (Alternatively, CPU controller on spinner provides a ramp up to desired speed then ramp down).

Alternatively, the enucleation MEMS device can be situated on a substrate base that facilitates fluid movements through micropumping means and the oocyte or embryo can be brought into close opposition with the active domain of the enucleation MEMS device by way of a lever element. Both the micropumping means and the lever element are actuated by a controller being in communication with these elements by way of circuit leads.

Determination of Successful Operation of the Enucleation MEMS Device

Success operation of the enucleation MEMS device is determined by the removal of the nuclear material of the oocyte or embryo in such a way that the cell is not irreparably damaged (i.e., lysis, extensive loss of cytoplasm). The condition of the oocyte or embryo after manipulation by the enucleation MEMS device is assayed by visual inspection under a microscope.

Determination of Effect of Enucleation MEMS Device on Oocyte or Embryo Viability and Developmental Fitness Further determination of oocyte or embryo quality after manipulation by the enucleation MEMS device includes: the culture of the cells for 24 hours post manipulation to determine stability of cell quality, and the further deposition of a donor nucleus or cell in the cytoplasm to determine the ability of the enucleated oocyte or embryo to support development of the cloned embryo.

Example

The Enucleation/Nuclear Transfer MEMS Device

Preparation of Cells to Serve as Donor Cells

Desirable culture cells (i.e., founder cells, transgenic culture cells, first generation cloned embryonic stem cells, adult somatic cells, primary culture of adult somatic cells, long term culture of adult somatic cells) being of any stage of the cell cycle (i.e., G1, G2, S, Mitosis, Meiosis, and quiescent) are washed with PBS, PBS/EGTA and then Trypsin/EDTA 0.25% to detach cells from substrate. Trypsin is neutralized by washing several times with centrifuge/wash steps in culture medium (i.e., HF-10, M199, M19, DMEM) and the cells are dispersed into a single cell suspension Operation of Enucleation/Nuclear Transfer MEMS Device The enucleation/nuclear transfer MEMS device/centrifugal platter cartridge is placed onto a spinning device. The central loading manifold is filled with loading fluid (i.e., Ham's F-10 Medium, PBS/PVA, M199 media, fluorescent dye, visible dye) and donor nuclei or donor cells. The enucleation/nuclear transfer MEMS device is spun at high speed (i.e., 4×g, 5×g, 6×g) for 10 seconds to purge bubbles and to load fluids and donor nuclei or donor cells throughout the cell loading region. Oocytes or embryos are placed into cell wells by mouth pipette, robotic pipette, or other manner. Spinner is rotated at low speed (i.e., 2×g, 3×g, 4×g) for a short period (i.e., 8 seconds, 9 seconds, 10 seconds), bringing the cells into contact with the enucleation penetration member and for nuclear migration to commence. The speed of rotation is ramped up to high speed (i.e., 5×g, 6×g, 7×g) for a longer period of time (5 seconds, 10 seconds, 15 seconds) to allow penetration of oocytes or embryos by the enucleation penetration member, to allow the extrusion of cell cytoplasm and nucleus, allow the severance of any cell remnant by the slideable shutter at the base of the enucleation penetration member, to allow the injection of a donor cell or donor nucleus into the cytoplasm of the enucleated oocyte or embryo, and then rotation is terminated. Cells are removed to incubated environment. (Alternatively, CPU controller on spinner provides a ramp up to desired speed then ramp down).

Alternatively, the enucleation/nuclear transfer MEMS device can be situated on a substrate base that facilitates fluid movements through micropumping means and the oocyte or embryo can be brought into close opposition with the active domain of the enucleation/nuclear transfer MEMS device by way of a lever element. Both the micropumping means and the lever element are actuated by a controller being in communication with these elements by way of circuit leads.

Determination of Successful Operation of the Enucleation/Nuclear Transfer MEMS Device Success operation of the enucleation/nuclear transfer MEMS device is determined by the removal of the nuclear material of the oocyte or embryo in such a way that the cell is not irreparably damaged (i.e., lysis, extensive loss of cytoplasm) and the deposition of one donor nucleus or donor cell into the cytoplasm of the enucleated oocyte or embryo. The condition of the oocyte or embryo (i.e., presence of a donor nucleus or donor cell) after manipulation by the enucleation MEMS device is assayed by visual inspection under a microscope.

Determination of Effect of Enucleation/Nuclear Transfer MEMS Device on Oocyte or Embryo Viability and Developmental Fitness The determination of oocyte or embryo quality after manipulation by the enucleation/nuclear transfer MEMS device includes: the culture of the reconstructed embryos post manipulation to determine stability of cell quality, the ability of the embryo to proceed through early embryonic development to the blastocyst stage, and then the determination of the ability of the reconstructed embryo to proceed through gestation to live birth after being transferred into a recipient animal.

Example

The Cytoplasmic Transfer MEMS Device

Operation of Cytoplasmic Transfer MEMS Device

The cytoplasmic transfer MEMS device kit with a centrifugal platter is placed onto a spinning device. The cell wells are filled with loading fluid (i.e., Ham's F-10 Medium, PBS/PVA, M199 media). The cytoplasmic transfer MEMS device, with both gating elements open, is spun at high speed (i.e., 4×g, 5×g, 6×g) for 10 seconds to purge bubbles and to load fluids throughout the cell loading region, extraction siphons, and supplemental input channel (being in fluid communication with the fluids in the cell wells). Oocytes or embryos are placed into cell wells by mouth pipette, robotic pipette, or other manner. Spinner is rotated at low speed (i.e., 2×g, 3×g, 4×g) for a short period (i.e., 8 seconds, 9 seconds, 10 seconds), bringing the oocyte or embryo into contact with the hollow protuberance. The speed of rotation is ramped up to high speed (i.e., 5×g, 6×g, 7×g) for a longer period of time (5 seconds, 10 seconds, 15 seconds) to allow penetration of oocyte or embryo by the hollow protuberance, to allow the extraction of an aliquot of cytoplasm from the cytoplasmic donor cell, to allow the cytoplasm aliquot to travel through the extraction siphon to the first gate, pass through the first gate, the closing of the first gate (being in communication with a controller by way of a circuit lead), the opening of the second gate allowing the cytoplasm aliqout and supplemental input fluid to flow through distal portion of the extraction siphon, through the hollow protuberance of the cell well containing the host oocyte or embryo into the host oocyte or embryo cytoplasm, and then rotation is terminated. Cells are removed to incubated environment. (Alternatively, CPU controller on spinner provides a ramp up to desired speed then ramp down).

Alternatively, the cytoplasmic transfer MEMS device can be situated on a substrate base that facilitates fluid movements through micropumping means and the oocyte or embryo can be brought into close opposition with the active domain of the cytoplasmic transfer MEMS device by way of a lever element. Both the micropumping means and the lever element are actuated by a controller being in communication with these elements by way of circuit leads.

Determination of Successful Operation of the Cytoplasmic Transfer MEMS Device

Successful operation of the cytoplasmic transfer MEMS device is determined by the removal of a portion of cytoplasmic material from a cytoplasmic donor oocyte or embryo and the deposition of this portion into the cytoplasm of the host oocyte or embryo. The determination of this success requires the visualization of the donor cytoplasm in the host cytoplasm and can be mediated by the labeling of the donor cytoplasm (i.e., cell being injected with a dye, cytoplasmic specific antibodies) prior to manipulation by the cytoplasmic transfer MEMS device. Additionally, it needs to be determined whether nuclear material from the donor oocyte or embryo is transferred with the cytoplasmic portion. This can be determined by the labeling of the DNA of the donor oocyte or embryo (i.e., ethidium bromide, anti-histone antibodies) prior to manipulation by the cytoplasmic transfer MEMS device. Additionally, it needs to be determined if the host oocyte or embryo has been irreparably damaged (i.e., lysis, extensive loss of cytoplasm) by this process. Microscopic examination for lysis or other hallmarks of cell death is performed.

Determination of Effect of Cytoplasmic Transfer MEMS Device on Oocyte or Embryo Viability and Developmental Fitness The determination of oocyte or embryo quality after manipulation by the cytoplasmic transfer MEMS device includes: the culture of the oocytes or embryos post manipulation to determine stability of cell quality, the ability of the oocyte to proceed through fertilization, and the ability of the embryo to proceed through early embryonic development to the blastocyst stage, and then the determination of the ability of the reconstructed embryo to proceed through gestation to live birth after being transferred into a recipient animal.

Example

The In Vitro Culture Device

Operation of In Vitro Culture Device

After having been placed in an environmental controlling instrument of the present invention, the single layer or multi-layer in vitro culture device is loaded with fluids (i.e., culture media), any bubbles being purged by gentle pressure being applied to the system through the loading/removal compartments or through the input and output enclosed channels. Oocytes or embryos, having been attached to labelable zona anchor MEMS devices that are attractive to the movement tracks of the in vitro culture device, are added to the loading compartment (i.e., by mouth pipette, by robotic means, by other cell handling means). The environmental controlling instrument CPU is provided with the desired culture conditions, time, and amendment parameters. The environmental controlling instrument CPU actuates the travel of the cells on the movement tracks through out the single or multi-layer in vitro culture device, provides culture amendments (i.e., change in sera concentration, change in hormone composition or concentration, change in temperature, change in pH, addition of co-culture conditioned medium, addition of sperm for IVF), provides for the observation of physical parameters within the in vitro culture device as well as for visual inspection of the oocytes or embryos as they pass the visual inspection devices of the environmental controlling instrument, provides for labeleable zona anchor MEMS device telemetry, namely the collection of information (i.e., specific physical parameters encountered by any single oocyte or embryo) from the labeleable zona anchor MEMS device resident on the oocyte or embryo, and provides for the positioning of the oocyte or embryo in a removal compartment for removal from device.

Determination of Successful Operation of the In Vitro Culture Device

Successful operation of the in vitro culture device is measured by determining the ability of the in vitro culture device to handle the oocytes or embryos in such a way that damage does not occur (i.e., the in vitro culture device does: not clog with cells; does not provide adverse physical conditions). Additionally, the oocytes or embryos are observed to determine if the in vitro culture device was able to provide the appropriate culture conditions. For example, if IVF of oocytes was desired the result must be that an acceptable number of oocytes have been inseminated, if oocyte maturation was desired then the result must be that and acceptable number of oocytes have been cultured to the stage desired such as the Meiosis II block, if in vitro culture of embryos was desired then an acceptable number of embryos must reach the stage of early embryonic development desired such as the blastocyst stage.

Although the invention described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All references and patents cited within are hereby incorporated by reference in their entirety.

What is claimed is:

1. An enucleation MEMS device for enucleating a cell comprising:
   (a) a first substrate comprising at least one well for holding a cell wherein the well comprises;
     (i) an enucleation penetration member to penetrate the cell to access the nucleus, wherein the enucleation penetration member is an emittor operatively connected to a source of electromagnetic signals or vibrational energy; and
     (ii) an enucleation pit, wherein the pit is capable of holding a nucleus isolated from the cell.

2. An enucleation/nuclear transfer MEMS device kit comprising:
   (a) an enucleation/nuclear transfer MEMS device of claim 1; and
   (b) a second substrate comprising an input well for depositing a cell, a lever element for controlling the cell apposition and a micropump for handling fluids.

3. A method of using the enucleation MEMS device of claim 1 comprising the steps of:
   (a) filling the well with a fluid;
   (b) loading the well with an oocyte or embryo;
   (c) applying a centripetal force to the enucleation MEMS device thereby causing the cell to be forced against the enucleation penetration member and forcing a portion of the cell containing the nucleus into the enucleation pit.

4. The enucleation MEMS device of claim 1 wherein the emittor conducts electromagnetic signals.

5. The enucleation MEMS device of claim 1 wherein the emitter conducts vibrational energy.

6. An enucleation MEMS device kit for enucleating a cell comprising:
   (a) at least one enucleation MEMS device for enucleating a cell, the enucleation MEMS device comprising a substrate, the substrate comprising at least one well for holding a cell wherein the well comprises;
     (i) an enucleation penetration member to penetrate the cell to access the nucleus; and
     (ii) an enucleation pit, wherein the pit is capable of holding a nucleus isolated from the cell; and
   (b) a centrifugal platter for supporting at least one MEMS device and for applying a centripetal force to a cell or group of cells contained within the MEMS device wherein the centrifugal disk comprises a plurality of ports for affixing the MEMS devices and a securing means for securing the centrifugal disk to a spinner or driving means.

7. The enucleation MEMS device kit of claim 6 wherein
   (a) the centrifugal platter comprises a plurality of grooves arranged in a concentric pattern and wherein each groove has an inner and outer edge;
   (b) at least one enucleation MEMS device is bonded to the outer edge of a groove in an orientation such that the axis of each well of the enucleation MEMS device is horizontal to the plane of the centrifugal platter; and
   (c) the inner edge of the grooves forming divided compartments comprising a single well which restrict the movement of materials from one compartment containing a single well to another compartment.

8. A method of using the enucleation MEMS device kit of claim 6 comprising the steps of:
   (a) filling the grooves of the centrifugal platter with a fluid;
   (b) loading the fluid within the grooves of the centrifugal platter with at least one oocyte or embryo;
   (c) rotating the kit such that centripetal forces are applied to the centrifugal platter such that the oocyte or embryo are thrust against the wall of the well such that the enucleation penetration member of the enucleation MEMS device penetrates the surface of the oocyte or embryo and
   (d) extruding the cell contents out of the oocyte or embryo containing a nucleus into the enculeation pit forming a cell extrusion; and
   (e) severing any remnant of the cell extrusion in enucleation pit with a slideable shutter.

9. A method of using the enucleation MEMS device kit of claim 6 comprising the steps of:
   (a) filling a plurality of grooves of the centrifugal platter with a fluid;
   (b) loading the fluid in the grooves of the centrifugal platter with at least one oocyte or embryo;
   (c) applying centripetal forces to the kit such that the oocyte or embryo makes contact with the enucleation MEMS device and penetrates the surface of the oocyte or embryo;
   (d) extruding a portion of the oocyte or embryo contents into the enucleation pit to isolate the nucleus; and
   (e) severing any remnant of cell extruded into enucleation pit using a slideable shutter.

10. The enucleation MEMS device kit of claim 6 wherein the enucleation MEMS devices are permanently attached to the centripetal platter.

11. An enucleation MEMS device for enucleating a cell comprising:
  (a) a base substrate comprising;
    (i) an input well to introduce a cell;
    (ii) a lever to control the motion of the cell; and
    (iii) a pump for applying a force to extrude a portion of the cell; and
  (b) an enucleation MEMS device.

12. A method of making an enucleation/nuclear transfer MEMS device comprising the steps of:
  (a) depositing a first mask on the top surface of a substrate inscribing a square shape;
  (b) etching the first mask to form a plurality of wells;
  (c) depositing a second mask in the wells of step (b) such that an enucleation penetration member is inscribed at the bottom of each well;
  (d) etching the second mask to form the enucleation penetration member;
  (e) applying a third mask within each well adjacent to the enucleation penetration member such that an enucleation pit is inscribed;
  (f) etching the third mask to form the enucleation pit;
  (g) applying a fourth mask such that a slidable shutter is inscribed;
  (h) etching the fourth mask to form the slideable shutter; and
  (i) depositing a circuit lead to provide communication between the shutter and a controller.

13. An enucleation/nuclear transfer MEMS array for the enucleation and transfer of a donor nucleus or donor cell comprising:
  (a) a central loading manifold for the loading of a donor nucleus or donor cell into the device;
  (b) at least one well for holding an oocyte or embryo during the enucleation process, wherein the well comprises:
    (i) a hollow protuberance in the well for penetrating the oocyte or embryo to introduce a donor nucleus or donor cell;
    (ii) an enucleation penetration member for penetrating an oocyte or embryo to facilitate the removal of a cell nucleus;
    (iii) an enucleation evacuation siphon to provide suction to remove the nucleus from the oocyte or embryo forming an enucleated oocyte or embryo; and
  (c) a dynamic hydropressure column for providing a pressurized fluid to introduce the donor nucleus or donor cell through the hollow protuberance into the enucleated oocyte or embryo.

14. A method of using enucleation/nuclear transfer MEMS array of claim 13 comprising the steps of:
  (a) loading a donor nuclei or donor cells into central loading manifold;
  (b) filling the well with a fluid;
  (c) loading the well with an oocyte or an embryo; and
  (d) rotating the enucleation/nuclear transfer MEMS array device.

15. A method of making an enucleation/nuclear transfer MEMS device comprising the steps of:
  (a) etching a plurality of parallel channels on a first side of a plurality of silicon wafers in which the wafers each have a second unetched side;
  (b) silicon fusion bonding the unetched side of a plurality of silicon wafers of step (a) to the etched side of a plurality of silicon wafers of step (a) such that the etched channels are in parallel to form a mega-laminate wherein the mega-laminate has a plurality of channels;
  (c) cutting the mega-laminate at an angle perpendicular to the long axis of the etched channels thereby forming a slice of the mega-laminate having a top surface and a bottom surface wherein each surface exposes an end of the channel;
  (d) silicon fusion bonding the bottom surface of the slice of the mega-laminate to the etched side of a channel-etched base-plate wafer;
  (e) depositing a first mask on the top surface of the slice of the mega-laminate such that a region surrounding each channel end is free of mask;
  (f) etching the mask to form a plurality of wells;
  (g) depositing a second mask in the wells of step (f) such that an enucleation penetration member is inscribed at the bottom of each well;
  (h) etching the second mask to form the enucleation penetration member;
  (i) applying a third mask within each well adjacent to the enucleation penetration member such that an enucleation pit is inscribed;
  (j) etching the third mask to form the enucleation pit;
  (k) applying a fourth mask such that a slidable shutter is inscribed;
  (l) etching the fourth mask to form a slideable shutter; and
  (m) depositing a circuit lead to provide communication between the slideable shutter and the controller.

16. The method of making an enucleation/nuclear transfer MEMS device of claim 15 further comprising applying a coating to the mega-laminate top surface after step (h).

17. The method of making an enucleation/nuclear transfer MEMS device of claim 16 wherein the coating is a polypeptide, peptide or protein.

18. The method of making an enucleation/nuclear transfer MEMS device of claim 17 wherein the polypeptide is polylysine.

19. An enucleation/nuclear transfer MEMS device kit for enucleating a cell comprising:
  (a) a centrifugal platter for providing support for at least one MEMS device and for applying a centripetal force to a cell or group of cells contained within the MEMS device wherein the centrifugal disk comprises a plurality of ports for affixing the MEMS device and a securing means for securing the centrifugal disk to a spinner or driving means; and
  (b) at least one enucleation/nuclear transfer MEMS device comprising a substrate comprising at least one well for holding a cell wherein the well comprises;
    (i) an enucleation penetration member to penetrate the cell to access the nucleus; and
    (ii) an enucleation pit for isolating the nucleus from the cell.

20. The enucleation/nuclear transfer MEMS device kit of claim 19 wherein the enucleation/nuclear transfer MEMS device is permanently affixed to the centrifugal platter.

21. The enucleation/nuclear transfer MEMS device kit of claim 19 wherein
  (a) the centrifugal platter comprises a plurality of grooves arranged in a concentric pattern and wherein each groove has an inner and outer edge;
  (b) at least one enucleation/nuclear transfer MEMS device is bonded to the outer edge of a groove in an orientation such that the axis of each well of the enucleation/nuclear transfer MEMS device is horizontal to the plane of the centrifugal platter; and
  (c) the inner edge of the grooves forming divided compartments comprising a single well which restrict the movement of materials from one compartment containing a containing a single well to another compartment.

22. A method of using the enucleation/nuclear transfer MEMS device kit of claim 19 comprising the steps of:
(a) filling a plurality of input wells of at least one enucleation/nuclear transfer MEMS device with a fluid;
(b) loading the fluid-filled wells of step (b) with at least one oocyte or embryo; and
(c) rotating the kit and thus applying a centripetal force on the enucleation/nuclear transfer MEMS/centrifugal platter.

23. A method of using an enucleation/nuclear transfer MEMS device kit of claim 21 comprising the steps of:
(a) loading donor nuclei or cells into the central loading manifold;
(b) filling the grooves of the centrifugal platter with a fluid;
(c) loading the grooves of the centrifugal platter with at least one oocyte or embryo;
(d) applying a centripetal force to the kit whereby the oocyte or embryo makes contact with the pertuberance of the enucleation/nuclear transfer MEMS device and the pertuberance penetrates the surface of the oocyte or embryo; and
(e) removal of oocyte or embryo from the kit.

24. A centrifugal platter for supporting MEMS devices and for applying a centripetal force to a cell or group of cells contained within a MEMS device facilitating migration of the cells onto the enucleation region of the MEMS device wherein the centrifugal platter comprises a circular disc, a plurality of ports capable of affixing the MEMS devices, and a temporary securing means capable of attaching to a spinner or driving means, wherein the centrifugal platter is readily connected to or detachable from the spinner or driving means.

25. A Cytoplasmic Transfer MEMS array for the transfer of cytoplasm from one cell to another comprising:
(a) a cytoplasmic transfer MEMS device comprising a substrate comprising:
(i) at least one first well wherein each first well compromises a hollow protuberance;
(ii) at least one second well wherein each second well compromises a hollow protuberance;
(iii) an extraction siphon in fluid communication with the hollow protuberance in the first well and with the hollow protuberance in the second well;
(iv) a supplemental input channel in fluid communication with the extraction siphon; and
(b) a centrifugal platter having a top and a bottom surface wherein the cytoplasmic transfer MEMS device is attached to the top surface.

26. A Cytoplasmic Transfer MEMS array comprising:
(a) a cytoplasmic transfer MEMS device comprising a substrate comprising:
(i) at least one first well wherein each first well compromises a hollow protuberance;
(ii) at least one second well wherein each second well compromises a hollow protuberance;
(iii) an extraction siphon in fluid communication with the hollow protuberance in the at least one first well and with the hollow protuberance in the at least one second well;
(iv) a supplemental input channel in fluid communication with the extraction siphon; and
(b) a centrifugal platter for applying a centripetal force to a cell or group of cells contained within a MEMS device, the centrifugal platter comprising a circular disk having a plurality of ports for holding the MEMS device.

27. A method of using a Cytoplasmic Transfer MEMS array of claim 26 comprising:
(a) loading fluid in the extraction siphon;
(b) loading a cytoplasmic donor oocyte or embryo in the first well;
(c) loading a recipient oocyte or embryo in the second well; and
(d) applying a force to the Cytoplasmic Transfer MEMS device by rotating the Cytoplasmic Transfer MEMS array on a spinner or driving means.

28. A multi-layer cell culture MEMS array for culturing a cell or groups of cells, comprising a multi-laminate planar layer comprising:
(a) at least one loading compartment for loading cells or groups of cells or fluids into the array;
(b) at least one enclosed channel in fluid communication with the loading compartment and wherein the enclosed channel allows for the passage of cells;
(c) at least one movement track attractive to labelable zona anchor MEMS attached to the enclosed channel;
(d) at least one removal compartment for the removal of cells or groups of cells; and
(e) at least one circuit lead providing communication between at least one movement track and a controller unit.

29. A multi-layer cell culture MEMS array of claim 28 further comprising at least one router element which resides on a movement track.

30. The multi-layer cell culture MEMS array of claim 29 wherein at least one enclosed channel with movement track is in fluid communication with a culture manifold for the transport of a cell or group of cells and fluid through the multi-layer cell culture MEMS array.

31. A single-layer MEMS culture array for culturing cells or a group of cells comprising:
(a) at least one loading compartment for loading cells or groups of cells or fluids into the device;
(b) at least one enclosed channel in fluid communication with the loading compartment and wherein the enclosed channel allows for the passage of cells;
(c) at least one movement track attractive to labelable zona anchor MEMS attached to the enclosed channel;
(d) at least one removal compartment for the removal of cells or groups of cells; and
(e) at least one circuit lead providing communication between at least one movement track and a controller unit.

32. A single layer cell culture MEMS array of claim 31 further comprising at least one router element which resides on a movement track.

33. The single layer cell culture MEMS array of claim 31 wherein at least one enclosed channel with movement track is in fluid communication with a culture manifold for the transport a cell or group of cells and fluid through the cell culture device.

34. An enucleation MEMS device for enucleating a cell comprising:
(a) a substrate comprising at least one well for holding a cell wherein the well comprises;
(i) an enucleation penetration member to penetrate the cell to access the nucleus;
(ii) an enucleation pit, wherein the pit is capable of holding a nucleus isolated from the cell;

(b) a slidable shutter adjacent to the union between the enucleation penetration member and the enucleation pit for severing a portion of the cell containing the nucleus; and (c) a controller in communication with the slideable shutter through a circuit lead to control the movement of the slideable shutter.

* * * * *